US012251459B2

(12) United States Patent
Boppana et al.

(10) Patent No.: US 12,251,459 B2
(45) Date of Patent: *Mar. 18, 2025

(54) COMPOSITIONS, FORMULATIONS, AND METHODS FOR HAIR TREATMENT

(71) Applicant: Oddity Labs, LLC, New York, NY (US)

(72) Inventors: Avinash Boppana, Boston, MA (US); Kongyu Zhang, Boston, MA (US); Evan Zhao, Woburn, MA (US); Connor Wilson Coley, Cambridge, MA (US); Enzo Corey Benfanti, Somerville, MA (US); Elizabeth Lee, San Diego, CA (US); Erin Horgan, Marblehead, MA (US); Tiffany Hua, Princeton, NJ (US); Amy Le, Quincy, MA (US)

(73) Assignees: Oddity Labs, LLC, New York, NY (US); Seung Hyeon Ko

( * ) Notice: Subject to any disclaimer, the term of this patent is extended or adjusted under 35 U.S.C. 154(b) by 0 days.

This patent is subject to a terminal disclaimer.

(21) Appl. No.: 18/092,517

(22) Filed: Jan. 3, 2023

(65) Prior Publication Data

US 2024/0225979 A1 Jul. 11, 2024

Related U.S. Application Data

(60) Provisional application No. 63/379,180, filed on Oct. 12, 2022.

(51) Int. Cl.
*A61Q 5/00* (2006.01)
*A61K 8/49* (2006.01)
*A61K 31/4196* (2006.01)
*A61K 31/495* (2006.01)
*A61Q 7/00* (2006.01)

(52) U.S. Cl.
CPC .......... *A61K 8/496* (2013.01); *A61K 31/4196* (2013.01); *A61K 31/495* (2013.01); *A61Q 5/00* (2013.01)

(58) Field of Classification Search
CPC ...... A61K 8/496; A61K 31/4196; A61K 8/49; A61Q 5/00; A61Q 7/00
See application file for complete search history.

(56) References Cited

U.S. PATENT DOCUMENTS

| | | | |
|---|---|---|---|
| 11,052,059 B2 | 7/2021 | Schmidt | |
| 2006/0019956 A1 | 1/2006 | Green | |
| 2007/0213321 A1* | 9/2007 | Chong | C07D 277/70 514/217.12 |
| 2016/0256440 A1* | 9/2016 | Short | A61K 31/506 |
| 2020/0354338 A1 | 11/2020 | Jin et al. | |
| 2023/0122670 A1* | 4/2023 | Boppana | A61K 31/415 514/181 |

FOREIGN PATENT DOCUMENTS

| | | |
|---|---|---|
| WO | WO-03072099 A1 | 9/2003 |
| WO | WO-2009031709 A1 | 3/2009 |
| WO | WO-2013049591 A2 | 4/2013 |
| WO | WO-2023018694 A1 | 2/2023 |

OTHER PUBLICATIONS

Weyand, Angela C., and Jordan A. Shavit. "Agent specific effects of anticoagulant induced alopecia." Research and practice in thrombosis and haemostasis 1.1 (2017): 90-92. (Year: 2017).*
Zhu, Peng, et al. "Novel AI-2 quorum sensing inhibitors in Vibrio harveyi identified through structure-based virtual screening." Bioorganic & medicinal chemistry letters 22.20 (2012): 6413-6417. (Year: 2012).*
Ni, Nanting, et al. "Identification of boronic acids as antagonists of bacterial quorum sensing in Vibrio harveyi." Biochemical and biophysical research communications 369.2 (2008): 590-594. (Year: 2008).*
Turovskiy, Yevgeniy, and Michael L. Chikindas. "Autoinducer-2 bioassay is a qualitative, not quantitative method influenced by glucose." Journal of microbiological methods 66.3 (2006): 497-503. (Year: 2006).*
Anan, et al. Protease-activated receptor-1 (thrombin receptor) is expressed in mesenchymal portions of human hair follicle. J Invest Dermatol. Oct. 2003;121(4):669-673. doi: 10.1046/j.1523-1747. 2003.12490.x.
Co-pending U.S. Appl. No. 17/818,563, inventors Boppana; Avinash et al., filed on Aug. 9, 2022.
Dolzhenko, et al. Synthesis and biological activity of 1, 3, 5-triazino [1, 2-a] benzimidazol-2-amines. Pharmaceutical Chemistry Journal 41.9 (2007): 470-473.
International search report with written opinion dated Jan. 13, 2023 for PCT/US2022/039800.
Kohra, et al. Synthesis of pyrimidine derivatives by the reaction of ketene dithioacetals with amides. Journal of Heterocyclic Chemistry, (1988). 25: 959-968. https://doi.org/10.1002/jhet.5570250349.
Kreher, et al. Herstellungsverfahren für 2-aryl-2H-isoindole. Manufacturing process for 2-Aryl-2H-isoindoles (English Title). Chemiker-Zeitung, 111. Jahrgang (1987) Nr. 5 (English Abstract).
Madsen, et al. Evaluation of water-soluble hemisuccinate esters of hydrocortisone and prednisolone; plasma 17-hydroxycorticosteroid concentrations following intravenous administration. Ama J Dis Child. Jan. 1959;97(1):66-71. doi: 10.1001/archpedi.1959. 02070010068005.

(Continued)

*Primary Examiner* — Abigail Vanhorn
(74) *Attorney, Agent, or Firm* — WILSON SONSINI GOODRICH & ROSATI

(57) ABSTRACT

Compositions and formulations for hair treatment are provided herein. Methods for hair treatment, such as methods for preventing or treating hair loss or hair thinning, are also provided herein. The methods and formulations may promote hair growth, hair restoration or hair thickening, or increase hair density or hair growth rate.

12 Claims, 15 Drawing Sheets

(56) References Cited

OTHER PUBLICATIONS

Martin, et al. Cyansäureester. 31. Umsetzungen von 2-Guanidino-benzimidazol mit elektrophilen Reagentien. Cyanic Acid Esters. 31. Reactions of 2-Guanidino-benzimidazole with Electrophilic Compounds (English title). Journal für Praktische Chemie. Jan. 1981, vol. 323 (Issue 2) p. 303-310 (Machine Translation paragraphs 1-2).
"Pubchem CID 135418902", Create date: Jan. 15, 2019 (Jan. 15, 2019).
Ryabova, et al. Synthesis and study of some properties of 1-aryl-2-oxo-1,2,3,6-tetrahydro[1,4]diazepino[6,5-b]indole 4-oxides. Russian Chemical Bulletin. vol. 52:1386-1398 (2003).
Soliman, et al. Synthesis and biological activity of dihydroimidazole and 3,4-dihydrobenzo[4,5]imidazo[1,2-a][1,3,5]triazins. Eur J Med Chem. Jan. 2012;47(1):138-142. doi: 10.1016/j.ejmech.2011.10.034. Epub Oct. 25, 2011.
PCT/US2024/010025 Invitation to Pay Additional Fees dated Mar. 18, 2024.
AKos Consulting & Solutions. PubChem No. 104825510. Retrieved May 23, 2024, from: https://pubchem.ncbi.nlm.nih.gov/substance/104825510. pp. 1-5. (2019).
AKos Consulting & Solutions. PubChem No. 105188766. Retrieved May 23, 2024, from: https://pubchem.ncbi.nlm.nih.gov/substance/105188766. pp. 1-5. (2019).
AKos Consulting & Solutions. PubChem No. 124423208. Retrieved May 23, 2024, from: https://pubchem.ncbi.nlm.nih.gov/substance/124423208. pp. 1-5. (2019).
Co-pending U.S. Appl. No. 18/092,517, inventors Boppanna; Avinash et al., filed on Jan. 3, 2023.
Co-pending U.S. Appl. No. 18/528,113, inventors Boppana; Avinash et al., filed on Dec. 4, 2023.
Paus, Ralf. Therapeutic strategies for treating hair loss. Drug Discovery Today: Therapeutic Strategies 3.1: 101-110. (2006).
PCT/US2022/039800 International Preliminary Report on Patentability dated Feb. 13, 2024.
PCT/US2023/082287 International Search Report dated Apr. 23, 2024.
PCT/US2023/082287 Invitation to Pay Additional Fees dated Feb. 13, 2024.
PCT/US2024/010025 International Search Report and Written Opinion dated May 23, 2024.
PubChem. National Center for Biotechnology Information. PubChem Compound Database, U.S. National Library of Medicine, Jan. 21, 2019, pubchem.ncbi.nlm.nih.gov/compund1360615. pp. 1-9.

* cited by examiner

COMPOSITIONS, FORMULATIONS, AND METHODS FOR HAIR TREATMENT

CROSS REFERENCE

This application claims the benefit of U.S. Provisional Patent Application No. 63/379,180, filed Oct. 12, 2022, which is incorporated by reference herein in its entirety.

SUMMARY

Hair loss or thinning is a common problem which is, for example, naturally occurring or chemically promoted through the long-term use of certain chemicals (e.g., commercial products or therapeutic drugs). Often such hair loss or thinning is accompanied by lack of hair re-growth which causes partial or full baldness. While hair loss is often thought of as a man's problem, at least a third of women will experience thinning hair at some point in their lives.

The disclosure provides compositions, formulations, methods, and kits for preventing or treating hair loss or hair thinning (whether or not a diagnosis of hair loss or hair thinning has been made). The composition comprises a compound having a structure of Formula (I), (II), (III), (IV), (V), (VI), (VII$_A$), (VII$_B$), or (VIII). The method comprises administering to a subject in need thereof a composition comprising a compound having a structure of a compound disclosed herein.

Provides herein is a composition for treating hair loss or hair thinning comprising a compound having a structure of Formula (VII$_B$):

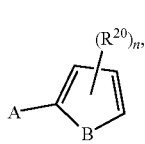

Formula (VII$_B$)

or a pharmaceutically or cosmetically acceptable salt thereof, wherein:
A is selected from a triazole, wherein the triazole is optionally substituted with one or more $R^{10}$;
B is selected from O, NH, S;
n is selected from 0, 1, 2, and 3;
each $R^{10}$ is independently selected at each occurrence from halogen, $C_{1-6}$ alkyl, $C_{2-6}$ alkenyl, and $C_{2-6}$ alkynyl, $-OR^{11}$, $-SR^{11}$, $-NO_2$, $=O$, $=NH$, $-CN$, $-C(O)R^{11}$, $-C(O)OR^{11}$, $-OC(O)R^{11}$, $-OC(O)N(R^{11})_2$, $-NR^{11}S(O)_2R^{11}$, $-C(O)N(R^{11})_2$, $-N(R^{11})C(O)R^{11}$, $-N(R^{11})C(O)N(R^{11})_2$, $-N(R^{11})C(O)OR^{11}$, $-S(O)_2(R^{11})$, $-S(O)_2N(R^{11})_2$, $C_{1-10}$ alkyl, $C_3$-$C_{12}$ carbocycle and 5- to 12-membered heterocycle;
each $R^{11}$ is independently selected at each occurrence from hydrogen; $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents selected from $=O$, and phenyl, wherein the phenyl is optionally substituted with one or more substituents independently selected from $-C(O)R^{12}$, and $-S(O)_2(R^{12})$;
each $R^{12}$ is independently selected at each occurrence from hydrogen, halogen, $-NHC_{1-10}$ alkyl, $-N(C_{1-10}$ alkyl$)_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle;
each $R^{20}$ is independently selected from halogen, $-OH$, $-CN$, $-NO_2$, $-NH_2$, $-NHC_{1-10}$ alkyl, $-N(C_{1-10}$ alkyl$)_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle; and
wherein a weight % of the compound in the composition has at least about 0.0001% to at most about 10% by weight relative to the total weight of the composition.

Provides herein is a composition for treating hair loss or hair thinning comprising a compound having a structure of Formula (VII$_B$):

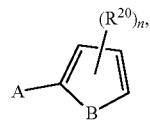

Formula (VII$_B$)

or a pharmaceutically or cosmetically acceptable salt thereof, wherein:
A is selected from a triazole, wherein the triazole is optionally substituted with one or more $R^{10}$;
B is selected from O, NH, S;
n is selected from 0, 1, 2, and 3;
each $R^{10}$ is independently selected at each occurrence from halogen, $C_{1-6}$ alkyl, $C_{2-6}$ alkenyl, and $C_{2-6}$ alkynyl, $-OR^{11}$, $-SR^{11}$, $-NO_2$, $=O$, $=NH$, $-CN$, $-C(O)R^{11}$, $-C(O)OR^{11}$, $-OC(O)R^{11}$, $-OC(O)N(R^{11})_2$, $-NR^{11}S(O)_2R^{11}$, $-C(O)N(R^{11})_2$, $-N(R^{11})C(O)R^{11}$, $-N(R^{11})C(O)N(R^{11})_2$, $-N(R^{11})C(O)OR^{11}$, $-S(O)_2(R^{11})$, $-S(O)_2N(R^{11})_2$, $C_{1-10}$ alkyl, $C_3$-$C_{12}$ carbocycle and 5- to 12-membered heterocycle;
each $R^{11}$ is independently selected at each occurrence from hydrogen; $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents selected from $=O$, and phenyl, wherein the phenyl is optionally substituted with one or more substituents independently selected from $-C(O)R^{12}$, and $-S(O)_2(R^{12})$;
each $R^{12}$ is independently selected at each occurrence from hydrogen, halogen, $-NHC_{1-10}$ alkyl, $-N(C_{1-10}$ alkyl$)_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle;
each $R^{20}$ is independently selected from halogen, $-OH$, $-CN$, $-NO_2$, $-NH_2$, $-NHC_{1-10}$ alkyl, $-N(C_{1-10}$ alkyl$)_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle.

In some embodiments, the compound of Formula (VII$_B$) is represented by

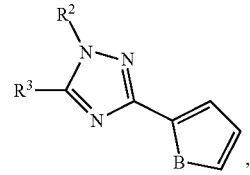

Formula (VII$_B$-A)

or a pharmaceutically or cosmetically acceptable salt thereof, wherein;

B is selected from oxygen and sulfur;
$R^2$ is $-S(O)_2(R^{11})$;
$R^3$ is $-SR^{11}$;
wherein each $R^{11}$ is selected from $C_{1-6}$ alkyl.
In some embodiments, the compound of Formula (VII$_B$) is represented by

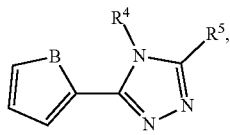

Formula (VII$_B$-B)

or a pharmaceutically or cosmetically acceptable salt thereof, wherein;
B is selected from oxygen and sulfur;
$R^4$ is $C_{1-6}$ alkyl;
$R^5$ is $-SR^{11}$; and
wherein $R^{11}$ is selected from $C_{1-6}$ alkyl, wherein $C_{1-6}$ alkyl is optionally substituted with one or more substituents selected from =O, and phenyl, wherein the phenyl is optionally substituted with one or more substituents independently selected from $-S(O)_2(R^{12})$, and wherein $R^{12}$ is a 5-membered heterocycle.
In some embodiments, the compound of Formula (VII$_B$) is represented by

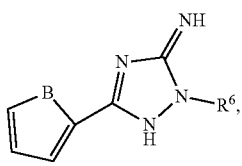

Formula (VII$_B$-C)

or a pharmaceutically or cosmetically acceptable salt thereof, wherein;
B is selected from oxygen and sulfur;
$R^6$ is $-S(O)_2(R^{11})$; and
wherein $R^{11}$ is selected from $C_{1-6}$ alkyl.
In some embodiments, the triazole is selected from

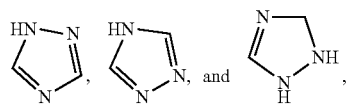

each of which is optionally substituted with one or more $R^{10}$.
In some embodiments, B is oxygen.
In some embodiments, $R^{10}$ is selected from $C_{1-6}$ alkyl, $-SR^{11}$, =NH, and $-S(O)_2(R^{11})$.
In some embodiments, $R^{11}$ is selected from $C_{1-2}$ alkyl, and

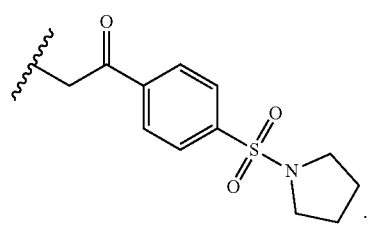 [SMILES: *CC(=O)c1ccc(S(=O)(=O)N2CCCC2)cc1]

In some embodiments, n is 0. In some embodiments, $R^4$ is $C_2$ alkyl.
In some embodiments, the compound is selected from:

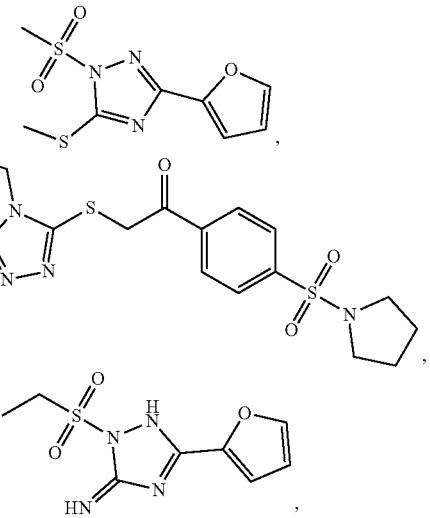

or a pharmaceutically or cosmetically acceptable salt thereof.
In some embodiments, the weight % of the compound in the composition ranges from about 0.01% to about 2.0%.
In some embodiments, the composition is a pharmaceutical composition or a cosmetic composition.
In some embodiments, the hair loss is selected from androgenic alopecia, alopecia areata, androgenetic alopecia, gynecologic alopecia, postpartum alopecia, seborrheic alopecia, non-rigid alopecia, senile alopecia, chemotherapy-induced alopecia, radiation-induced alopecia, male-pattern baldness, female-pattern baldness, cicatricial alopecia, alopecia areata telogen effluvium, traction alopecia, anagen effluvium, and combinations thereof.
In some embodiments, the hair is scalp hair, eyelash hair, eyebrow hair, facial hair, or combinations thereof.
Provided herein also is a composition for treating hair loss or hair thinning comprising a compound having a compound having a structure of Formula (VII$_A$):

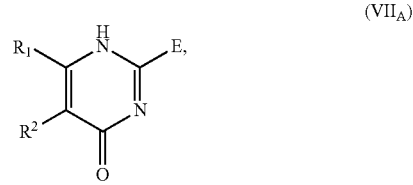

(VII$_A$)

or a pharmaceutically or cosmetically acceptable salt thereof, wherein:
E is selected from hydrogen, $C_5$-$C_8$ aryl, and heteroaryl;
$R^1$ is selected from hydrogen, $C_{1-6}$ alkyl, $C_{1-6}$ haloalkyl, $-S-C_{1-6}$ alkyl, $-S-C_{1-6}$ haloalkyl, $-S(O)(O)R^a$;
wherein $R^a$ is selected from hydrogen, $C_{1-6}$ alkyl, and $C_{1-6}$ haloalkyl; and
$R^2$ is selected from $-C(O)OH$, $-C(O)O-R^c$, and $-C(O)O-C_{1-6}$ haloalkyl,
wherein a weight % of the compound in the composition is at least about 0.0001% to at most about 10% by weight relative to the total weight of the composition.

In some embodiments, E is $C_5$-$C_8$ aryl.
In some embodiments, E is phenyl.
In some embodiments, $R^1$ is —S(O)(O)$CH_3$.
In some embodiments, $R^2$ is —C(O)O$CH_3$.
In some embodiments, the compound of Formula (VII$_A$) is

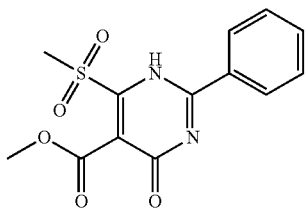 [SMILES: COC(=O)c1c(S(C)(=O)=O)[nH]c(-c2ccccc2)nc1=O]

or a pharmaceutically or cosmetically acceptable salt thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4B shows representative plots showing change in HLA-DR expression. Expression of CD80 (FIG. 4C), PDL-1 (FIG. 4D), and CD141 (FIG. 4E) was quantified via mean fluorescence intensity (MFI) following dosing with various example compounds. Data represents mean±s.d. and representative of at least 2 experimental replicates.

DETAILED DESCRIPTION OF THE INVENTION

Figure 1:
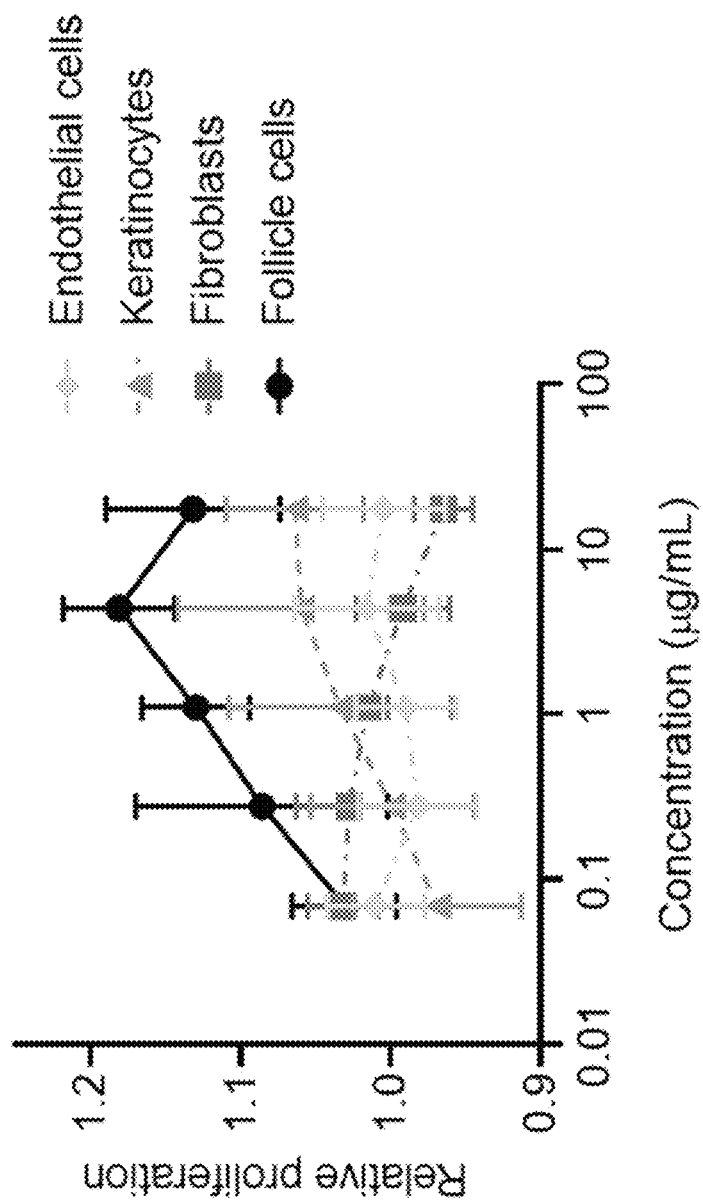
FIG. 1 shows the dose response curves from compound VII-3, in accordance with one or more embodiments of the present disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In certain aspects, the disclosure provides methods for preventing or treating hair loss or hair thinning. In some instances, the hair loss or hair thinning has not been diagnosed. In some instances, the hair loss or hair thinning has been diagnosed.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

The term "$C_{x-y}$" or "$C_x$-$C_y$," when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

The term "aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

The term "cycloalkyl" refers to a saturated ring in which each atom of the ring is carbon. Cycloalkyl may include monocyclic and polycyclic rings such as 3- to 10-membered monocyclic rings. 5- to 12-membered bicyclic rings, spiro bicycles, and 5- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl.

The term "halo" or, alternatively, "halogen" or "halide," means fluoro, chloro, bromo or iodo. In some embodiments, halo is fluoro, chloro, or bromo.

The term "haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally further substituted as described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, 5- to 12-membered spiro bicycles, and 5- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicylic rings e.g., 5 to 12-membered spiro bicycles.

"Heteroaryl" or "aromatic heterocycle" refers to a radical derived from a heteroaromatic ring radical that comprises one to eleven carbon atoms and at least one heteroatom wherein each heteroatom may be selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, pyran, thiophene, isoxazole, benzimidazole, benzthiazole, and imidazopyridine. An "X-membered heteroaryl" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^{bb}$—OR$^{aa}$, —R$^{bb}$—OC(O)—R$^{aa}$, —R$^{bb}$—OC(O)—OR$^{aa}$, —R$^{bb}$—OC(O)—N(R$^{aa}$)$_2$, —R$^{bb}$—N(R$^{aa}$)$_2$, —R$^{bb}$—C(O)R$^{aa}$, —R$^{bb}$—C(O)OR$^{aa}$, —R$^{bb}$—C(O)N(R$^{aa}$)$_2$, —R$^{bb}$—O—R$^{cc}$—C(O)N(R$^{aa}$)$_2$, —R$^{bb}$—N(R$^{aa}$)C(O)OR$^{aa}$, —R$^{bb}$—N(R$^{aa}$)C(O)R$^{aa}$, —R$^{bb}$—N(R$^{aa}$)S(O)$_t$R$^{aa}$ (where t is 1 or 2), —R$^{bb}$—S(O)$_t$R$^{aa}$ (where t is 1 or 2), —R$^{bb}$—S(O)$_t$OR$^{aa}$ (where t is 1 or 2), and —R$^{bb}$—S(O)$_t$N(R$^{aa}$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (—O), thioxo (=S), cyano (—CN), nitro (—NO$_2$), imino (=N—H), oximo (=N—OH), hydrazine (=N—NH$_2$), —R$^{bb}$—OR$^{aa}$, —R$^{bb}$—OC(O)—R$^{aa}$, —R$^{bb}$—OC(O)—OR$^{aa}$, —R$^{bb}$—OC(O)—N(R$^{aa}$)$_2$, —R$^{bb}$—N(R$^{aa}$)$_2$, —R$^{bb}$—C(O)R$^{aa}$, —R$^{bb}$—C(O)OR$^{aa}$, —R$^{bb}$—C(O)N(R$^{aa}$)$_2$, —R$^{bb}$—O—R$^{cc}$C(O)N(R$^{aa}$)$_2$, —R$^{bb}$—N(R$^{aa}$)C(O)OR$^{aa}$, —R$^{bb}$—N(R$^{aa}$)C(O)R$^{aa}$, —R$^{bb}$—N(R$^{aa}$)S(O)$_t$R$^{aa}$ (where t is 1 or 2), —R$^{bb}$—S(O)$_t$R$^{aa}$ (where t is 1 or 2), —R$^{bb}$—S(O)$_t$OR$^{aa}$ (where t is 1 or 2) and —R$^{bb}$—S(O)$_t$N(R$^{aa}$)$_2$ (where t is 1 or 2); wherein each R$^{aa}$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^{aa}$, valence permitting, may be optionally substituted with alkyl, alkenyl, alkynyl, halogen, haloalkyl, haloalkenyl, haloalkynyl, oxo (—O), thioxo (=S), cyano (—CN), nitro (—NO$_2$), imino (=N—H), oximo (=N—OH), hydrazine (=N—NH$_2$), —R$^{bb}$—OR$^{aa}$, —R$^{bb}$—OC(O)—R$^{aa}$, —R$^{bb}$—OC(O)—OR$^{aa}$, —R$^{bb}$—OC(O)—N(R$^{aa}$)$_2$, —R$^{bb}$—N(R$^{aa}$)$_2$, —R$^{bb}$—C(O)R$^{aa}$, —R$^{bb}$—C(O)OR$^{aa}$, —R$^{bb}$—C(O)N(R$^{aa}$)$_2$, —R$^{bb}$—O—R$^{cc}$—C(O)N(R$^{aa}$)$_2$, —R$^{bb}$—N(R$^{aa}$)C(O)OR$^{aa}$, —R$^{bb}$—N(R$^{aa}$)C(O)R$^{aa}$, —R$^{bb}$—N(R$^{aa}$)S(O)$_t$R$^{aa}$ (where t is 1 or 2), —R$^{bb}$—S(O)$_t$R$^{aa}$ (where t is 1 or 2), —R$^{bb}$—S(O)$_t$OR$^{aa}$ (where t is 1 or 2) and —R$^{bb}$—S(O)$_t$N(R$^{aa}$)$_2$ (where t is 1 or 2); and wherein each R$^{bb}$ is independently selected from a direct bond or a straight or branched alkylene, alkenylene, or alkynylene chain, and each R$^{cc}$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The term "exemplary" as used herein means "serving as an example, instance, or illustration." Any embodiment described herein as "exemplary" is not to be construed as preferred or advantageous over other embodiments.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soy bean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the term "cosmetically acceptable salt" means any salt that is cosmetically tolerated if used appropriately for a cosmetic treatment especially if used on or applied to humans and/or mammals. In certain embodiments, these salts include, but are not restricted to the salts used to form base addition salts, either inorganic, such as for example and in a non-limiting sense, lithium, sodium, potassium, calcium, magnesium or aluminium, among others, or organic such as for example and in a non-limiting sense, ethylamine, diethylamine, ethylenediamine, ethanolamine, diethanolamine, arginine, lysine, histidine, or piperazine among others, or acid addition salts, either organic, such as for example and in a non-limiting sense, acetate, citrate, lactate, malonate, maleate, tartrate, fumarate, benzoate, aspartate, glutamate, succinate, oleate, trifluoroacetate, oxalate, pamoate or gluconate among others, or inorganic, such as for example and in a non-limiting sense, chloride, sulfate, borate, or carbonate among others.

A "cosmetically effective amount" as used herein refers to the amount of a compound sufficient to improve the outward physical appearance of a subject. It is to be understood that a "cosmetically effective" amount can vary from subject to subject, due to numerous factors including for example age, weight, general condition of the subject, the condition being treated, the severity of the condition being treated, and the judgment of the prescribing physician.

The phrase "cosmetically acceptable excipient" or "cosmetically acceptable carrier" as used herein comprises as a pharmaceutical cream base, an oil-in-water emulsion, a water-in-oil emulsion, a gel, or the like. The skilled artisan will understand that the appropriate carriers typically will contain ingredients, such as those typically found in the cosmetic and cosmeceutical fields: oils, waxes or other standard fatty substances, or conventional gelling agents and/or thickeners; emulsifiers; moisturizing agents; emollients; sunscreens; hydrophilic or lipophilic active agents; agents for combatting free radicals; preservatives; basifying or acidifying agents; fragrances; surfactants; fillers; natural products or extracts of natural product, such as aloe or green tea extract; vitamins; or coloring materials.

The term "in vivo" generally refers to an event that takes place in a subject's body.

The term "in vitro" generally refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Compounds

The present disclosure provides compounds, salts thereof, and compositions and formulations thereof, for hair treatment. The compounds or salts thereof may have a structural formula (I), (II), (III), (IV), (V), (VI), (VII$_A$), (VII$_B$), or (VIII). The compounds or salts thereof may be selected from those forth in Tables 1-10, or any subset thereof. The compounds and salts thereof disclosed herein may be used in method(s) of the disclosure.

Compounds of Formula (VII$_B$) and Salts thereof

In certain aspects, disclosed herein is a compound having a structure of Formula (VII$_B$):

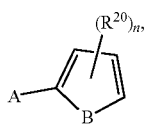

Formula (VII$_B$)

or a pharmaceutically or cosmetically acceptable salt thereof, wherein:
A is selected from a triazole, wherein the triazole is optionally substituted with one or more $R^{10}$;
B is selected from O, NH, S;
n is selected from 0, 1, 2, and 3;
each $R^{10}$ is independently selected at each occurrence from halogen, $C_{1-6}$ alkyl, $C_{2-6}$ alkenyl, and $C_{2-6}$ alkynyl, —$OR^{11}$, —$SR^{11}$, —$NO_2$, =O, =NH, —CN, —$C(O)R^{11}$, —$C(O)OR^{11}$, —$OC(O)R^{11}$, —$OC(O)N(R^{11})_2$, —$NR^{11}S(O)_2R^{11}$, —$C(O)N(R^{11})_2$, —$N(R^{11})C(O)R^{11}$, —$N(R^{11})C(O)N(R^{11})_2$, —$N(R^{11})C(O)OR^{11}$, —$S(O)_2(R^{11})$, —$S(O)_2N(R^{11})_2$, $C_{1-10}$ alkyl, $C_3$-$C_{12}$ carbocycle and 5- to 12-membered heterocycle;
each $R^{11}$ is independently selected at each occurrence from hydrogen; $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents selected from =O, and phenyl, wherein the phenyl is optionally substituted with one or more substituents independently selected from —$C(O)R^{12}$, and —$S(O)_2(R^{12})$;
each $R^{12}$ is independently selected at each occurrence from hydrogen, halogen, —$NHC_{1-10}$ alkyl, —$N(C_{1-10}$ alkyl)$_2$, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle;
each $R^{20}$ is independently selected from halogen, —OH, —CN, —$NO_2$, —$NH_2$, —$NHC_{1-10}$ alkyl, —$N(C_{1-10}$ alkyl)$_2$, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle.

In some embodiments, the compound of Formula (VII$_B$) is represented by

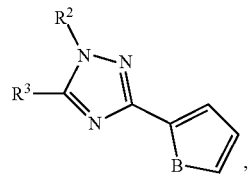

Formula (VII$_B$-A)

or a pharmaceutically or cosmetically acceptable salt thereof, wherein;
B is selected from oxygen and sulfur;
$R^2$ is —$S(O)_2(R^{11})$;
$R^3$ is —$SR^{11}$;
wherein each $R^{11}$ is selected from $C_{1-6}$ alkyl.

In some embodiments, B is oxygen. In some embodiments, $R^{11}$ is $C_1$alkyl.

In some embodiments, the compound of Formula (VII$_B$) is represented by

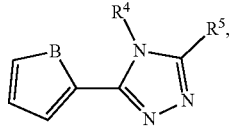

Formula (VII$_B$-B)

or a pharmaceutically or cosmetically acceptable salt thereof, wherein;

B is selected from oxygen and sulfur;
R$^4$ is C$_{1-6}$ alkyl;
R$^5$ is —SR$^{11}$; and
wherein R$^{11}$ is selected from C$_{1-6}$ alkyl, wherein C$_{1-6}$ alkyl is optionally substituted with one or more substituents selected from =O, and phenyl, wherein the phenyl is optionally substituted with one or more substituents independently selected from —S(O)$_2$(R$^{12}$), and wherein R$^{12}$ is a 5-membered heterocycle.

In some embodiments, B is oxygen. In some embodiments, R$^4$ is C$_2$alkyl. In some embodiments, R$^{12}$ is

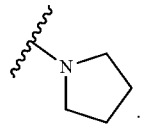

In some embodiments, the compound of Formula (VII$_B$) is represented by

Formula (VII$_B$-C)

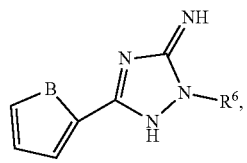

or a pharmaceutically or cosmetically acceptable salt thereof, wherein;
B is selected from oxygen and sulfur;
R$^6$ is —S(O)$_2$(R$^{11}$); and
wherein R$^{11}$ is selected from C$_{1-6}$ alkyl.

In some embodiments, B is oxygen. In some embodiments, R$^{11}$ is C$_2$ alkyl.

In some embodiments, the triazole is selected from

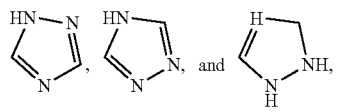

each of which is optionally substituted with one or more R$^{10}$.

In some embodiments, B is oxygen.

In some embodiments, R$^{10}$ is selected from C$_{1-6}$ alkyl, —SR$^{11}$, =NH, and —S(O)$_2$(R$^{11}$). In some embodiments, R$^{11}$ is selected from C$_{1-2}$ alkyl and

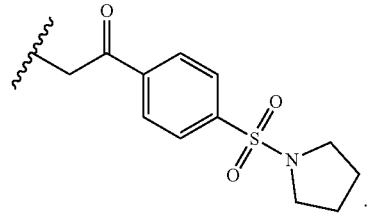 [SMILES: *CC(=O)c1ccc(S(=O)(=O)N2CCCC2)cc1]

In some embodiments, R$^{10}$ is C$_{1-6}$ alkyl. In some embodiments, R$^{10}$ is C$_2$ alkyl.

In some embodiments, R$^{10}$ is —SR$^{11}$. In some embodiments, R$^{11}$ is C$_1$ alkyl. In some embodiments, R$^{11}$ is

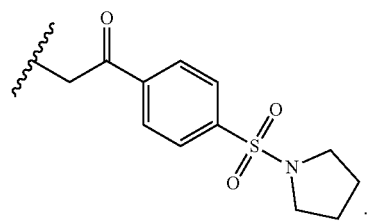 [SMILES: *CC(=O)c1ccc(S(=O)(=O)N2CCCC2)cc1]

In some embodiments, R$^{10}$ is =NH.

In some embodiments, R$^{10}$ is —S(O)$_2$(R$^{11}$). In some embodiments, R$^{11}$ is C$_2$ alkyl.

In some embodiments, n is 0. In some embodiments, R$^4$ is C$_2$ alkyl.

In some embodiments, a compound having structural Formula (VII$_B$) is selected from those set forth in Table 1, and salts thereof.

TABLE 1

Compounds of Formula (VII$_B$)

| ID # | Chemical Structure | Chemical Name | Molecular Weight |
|---|---|---|---|
| VII-2 | 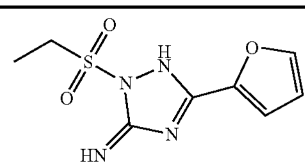 | 1H-1,2,4-Triazol-5-amine, 1-(ethylsulfonyl)-3-(2-furanyl)- | 242.260 |
| VII-3 | 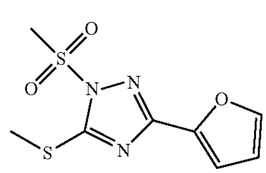 [SMILES: CSc1nc(-c2ccco2)nn1S(C)(=O)=O] | 1H-1,2,4-Triazole, 3-(2-furanyl)-1-(methylsulfonyl)-5-(methylthio)- | 259.312 |

TABLE 1-continued

Compounds of Formula (VII$_B$)

| ID # | Chemical Structure | Chemical Name | Molecular Weight |
|---|---|---|---|
| VII-4 | 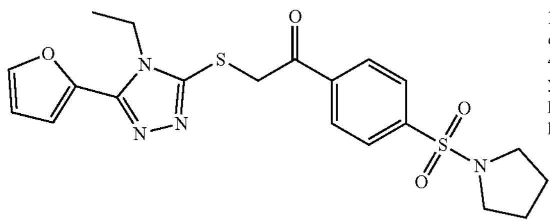 [SMILES: CCn1c(SCC(=O)c2ccc(S(=O)(=O)N3CCCC3)cc2)nnc1-c1ccco1] | Ethanone, 2-[[4-ethyl-5-(2-furanyl)-4H-1,2,4-triazol-3-yl]thio]-1-[4-(1-pyrrolidinylsulfonyl)phenyl]- | 446.554 |

Compounds of Formula (VII$_A$) and Salts Thereof

In certain aspects, disclosed herein is a compound having a structure of Formula (VII$_A$):

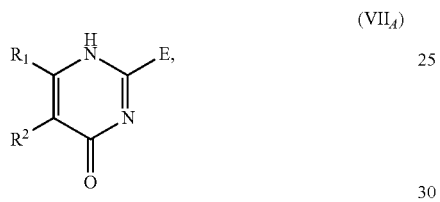

(VII$_A$)

or a pharmaceutically or cosmetically acceptable salt thereof, wherein:

E is selected from hydrogen, $C_5$-$C_8$ aryl, and heteroaryl;

$R^1$ is selected from hydrogen, $C_{1-6}$ alkyl, $C_{1-6}$ haloalkyl, —S—$C_{1-6}$ alkyl, —S—$C_{1-6}$ haloalkyl, —S(O)(O)$R^a$; wherein $R^a$ is selected from hydrogen, $C_{1-6}$ alkyl, and $C_{1-6}$ haloalkyl; and $R^2$ is selected from —C(O)OH, —C(O)O—$R^c$, and —C(O)O—$C_{1-6}$ haloalkyl.

In some embodiments, E is $C_5$-$C_8$ aryl. In some embodiments, E is phenyl.

In some embodiments, $R^1$ is S(O)(O)$R^a$. In some embodiments, $R^a$ is $C_1$alkyl. In some embodiments, $R^1$ is —S(O)(O)CH$_3$.

In some embodiments, $R^2$ is —C(O)O—$R^c$. In some embodiments, $R^2$ is —C(O)OCH$_3$.

In some embodiments, a compound having structural Formula (VII$_A$) is the compound shown in Table 2, or a salt thereof.

Compounds of Formula (VIII) and Salts Thereof

In certain aspects, disclosed herein is a compound having a structure of Formula (VIII):

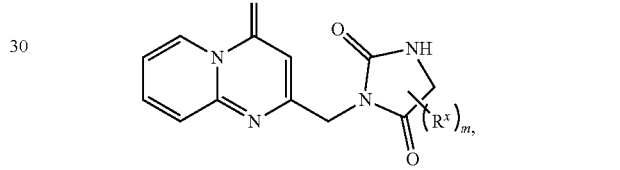

(VIII)

or a salt thereof, wherein:

m is 0, 1, or 2; and $R^x$ is each independently $C_{1-6}$ alkyl, $C_{5-8}$ aryl, $C_{1-6}$ haloalkyl, alkylaryl, or haloalkylaryl.

In some embodiments of a compound having structural Formula (VIII) (or a salt thereof), m is 2. In some embodiments, $R^x$ is each independently methyl or phenyl.

In some embodiments, a compound having structural Formula (VIII) is the compound shown in Table 3, or a salt thereof.

TABLE 2

Compound of Formula (VII$_A$)

| ID # | Chemical Structure | Chemical Name | Molecular Weight |
|---|---|---|---|
| VII-1 | 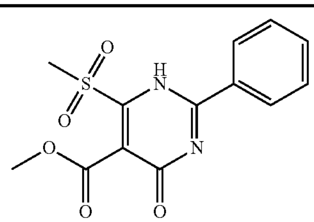 | 5-Pyrimidinecarboxylic acid, 1,4-dihydro-6-(methylsulfonyl)-4-oxo-2-phenyl-, methyl ester | 308.315 |

TABLE 3

Compound of Formula (VIII)

| ID # | Chemical Structure | Chemical Name | Molecular Weight |
|---|---|---|---|
| VII-25 | 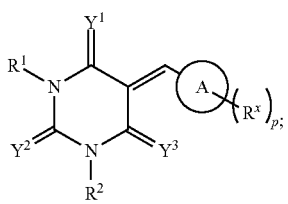 | 2,4-Imidazolidinedione, 5-methyl-3-[(4-oxo-4H-pyrido[1,2-a]pyrimidin-2-yl)methyl]-5-phenyl- | 348.362 |

Compounds of Formula (I) and Salts Thereof

In certain aspects, disclosed herein is a compound having a structure of Formula (I):

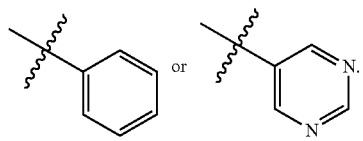 [SMILES: *c1ccccc1 ; *c1cncnc1]

(I)

or a salt thereof, wherein:
- $Y^1$ is O or S;
- $Y^2$ is O or S;
- $Y^3$ is O or S;
- $R^1$ is selected from H, alkyl, haloalkyl, alkenyl, haloalkenyl, aryl (e.g., phenyl), and aralkyl (e.g., benzyl), wherein the aryl or aralkyl is optionally substituted with one or more substituents independently selected from halogen, alkyl, alkoxy, and haloalkoxy;
- $R^2$ is selected from H, alkyl, alkenyl, haloalkyl, and haloalkenyl;
- A is aryl (e.g., phenyl) or heteroaryl (e.g., pyrimidinyl);
- p is 0, 1, 2, or 3; and
- $R^x$ is each independently selected from halogen, alkyl, haloalkyl, alkenyl, haloalkenyl, —OH, alkoxy, haloalkoxy, —O-alkylene-C(O)OH, nitro, —NH$_2$, alkylamino, dialkylamino, and haloalkylamino; or, alternatively, two $R^x$ together with the atoms to which they are attached to form (e.g., $C_4$-$C_6$) cycloalkyl or (e.g., 5- or 6-membered) heterocyclyl, wherein the cycloalkyl or heterocyclyl is optionally substituted with one or more substituents independently selected from halogen, alkyl, and haloalkyl.

In some embodiments of a compound having structural Formula (I) (or a salt thereof), $R^2$ is selected from (e.g., $C_{1-6}$, such as $C_{1-4}$) alkyl, (e.g., $C_{1-6}$, such as $C_{1-4}$) alkenyl, (e.g., $C_{1-6}$, such as $C_{1-4}$) haloalkyl, and (e.g., $C_{1-6}$, such as $C_{1-4}$) haloalkenyl. In some embodiments, $Y^1$ is S. In some embodiments, $Y^3$ is S. In some embodiments, A is

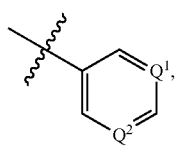

wherein $Q^1$ and $Q^2$ are each independently CH or N. In some embodiments, A is

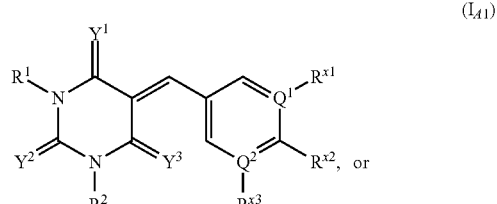

In some embodiments, the compound having a structural Formula (I) (or the salt thereof) has a structural Formula ($I_{A1}$) or ($I_{A2}$):

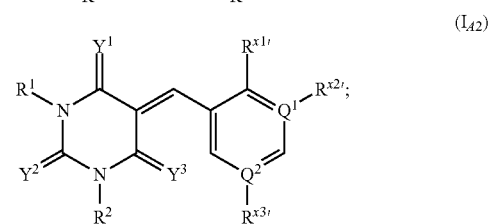

or a salt thereof, wherein:
- $R^{x1}$, $R^{x2}$, $R^{x3}$, $R^{x1'}$, $R^{x2'}$, and $R^{x3'}$ are each independently selected from halogen, (e.g., $C_{1-6}$, such as $C_{1-4}$) alkyl, (e.g., $C_{1-6}$, such as $C_{1-4}$) haloalkyl, (e.g., $C_{1-6}$, such as $C_{1-4}$) alkenyl, (e.g., $C_{1-6}$, such as $C_{1-4}$) haloalkenyl, —OH, (e.g., $C_{1-6}$, such as $C_{1-4}$) alkoxy, (e.g., $C_{1-6}$, such as $C_{1-4}$) haloalkoxy, —O-alkylene-C(O)OH, nitro, —NH$_2$, (e.g., $C_{1-6}$, such as $C_{1-4}$) alkylamino, (e.g., $C_{1-6}$, such as $C_{1-4}$) dialkylamino, and (e.g., $C_{1-6}$, such as $C_{1-4}$) haloalkylamino.

In some embodiments of a compound having structural Formula ($I_{A1}$) or ($I_{A2}$) (or a salt thereof), $R^2$ is selected from (e.g., $C_{1-6}$, such as $C_{1-4}$) alkyl, (e.g., $C_{1-6}$, such as $C_{1-4}$) alkenyl, (e.g., $C_{1-6}$, such as $C_{1-4}$) haloalkyl, and (e.g., $C_{1-6}$, such as $C_{1-4}$) haloalkenyl. In some embodiments, $Y^1$ is S. In some embodiments, $Y^3$ is S. In some embodiments, A is

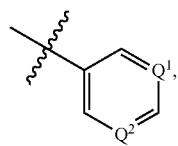

wherein Q¹ and Q² are each independently CH or N. In some embodiments, A is

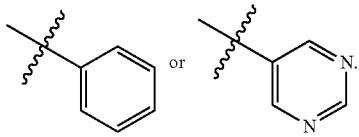 [SMILES: *c1ccccc1 ; *c1cncnc1]

In some embodiments, the compound having a structural Formula (I) (or the salt thereof) has a structural Formula ($I_{B1}$):

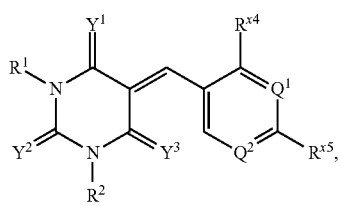

($I_{B1}$)

wherein:

$R^{x4}$ and $R^{x5}$ are each independently selected from halogen, (e.g., $C_{1-6}$, such as $C_{1-4}$) alkyl, (e.g., $C_{1-6}$, such as $C_{1-4}$) haloalkyl, (e.g., $C_{1-6}$, such as $C_{1-4}$) alkenyl, (e.g., $C_{1-6}$, such as $C_{1-4}$) haloalkenyl, —OH, (e.g., $C_{1-6}$, such as $C_{1-4}$) alkoxy, (e.g., $C_{1-6}$, such as $C_{1-4}$) haloalkoxy, —O-alkylene-C(O)OH, nitro, —NH₂, (e.g., $C_{1-6}$, such as $C_{1-4}$) alkylamino, (e.g., $C_{1-6}$, such as $C_{1-4}$) dialkylamino, and (e.g., $C_{1-6}$, such as $C_{1-4}$) haloalkylamino.

In some embodiments of a compound having structural Formula ($I_{B1}$) (or a salt thereof), $R^2$ is selected from (e.g., $C_{1-6}$, such as $C_{1-4}$) alkyl, (e.g., $C_{1-6}$, such as $C_{1-4}$) alkenyl, (e.g., $C_{1-6}$, such as $C_{1-4}$) haloalkyl, and (e.g., $C_{1-6}$, such as $C_{1-4}$) haloalkenyl. In some embodiments, $Y^1$ is S. In some embodiments, $Y^3$ is S. In some embodiments, A is

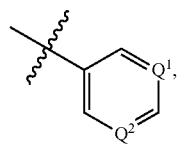

wherein Q¹ and Q² are each independently CH or N. In some embodiments, A is

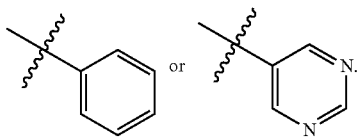 [SMILES: *c1ccccc1 ; *c1cncnc1]

In some embodiments, the compound having a structural Formula (I) (or the salt thereof) has a structural Formula ($I_{B2}$):

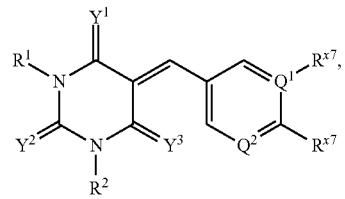

($I_{B2}$)

wherein:

$R^{x6}$ and $R^{x7}$ are each independently selected from halogen, (e.g., $C_{1-6}$, such as $C_{1-4}$) alkyl, (e.g., $C_{1-6}$, such as $C_{1-4}$) haloalkyl, (e.g., $C_{1-6}$, such as $C_{1-4}$) alkenyl, (e.g., $C_{1-6}$, such as $C_{1-4}$) haloalkenyl, —OH, (e.g., $C_{1-6}$, such as $C_{1-4}$) alkoxy, (e.g., $C_{1-6}$, such as $C_{1-4}$) haloalkoxy, —O-alkylene-C(O)OH, nitro, —NH₂, (e.g., $C_{1-6}$, such as $C_{1-4}$) alkylamino, (e.g., $C_{1-6}$, such as $C_{1-4}$) dialkylamino, and (e.g., $C_{1-6}$, such as $C_{1-4}$) haloalkylamino; or, alternatively, $R^{x6}$ and $R^{x7}$ together with the atoms to which they are attached to form cycloalkyl or heterocyclyl, wherein the cycloalkyl or heterocyclyl is optionally substituted with one or more substituents independently selected from halogen, (e.g., $C_{1-6}$, such as $C_{1-4}$) alkyl, and (e.g., $C_{1-6}$, such as $C_{1-4}$) haloalkyl.

In some embodiments of a compound having structural Formula ($I_{B2}$) (or a salt thereof), $R^2$ is selected from (e.g., $C_{1-6}$, such as $C_{1-4}$) alkyl, (e.g., $C_{1-6}$, such as $C_{1-4}$) alkenyl, (e.g., $C_{1-6}$, such as $C_{1-4}$) haloalkyl, and (e.g., $C_{1-6}$, such as $C_{1-4}$) haloalkenyl. In some embodiments, $Y^1$ is S. In some embodiments, $Y^3$ is S. In some embodiments, A is

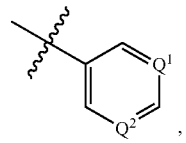

wherein Q¹ and Q² are each independently CH or N. In some embodiments, A is

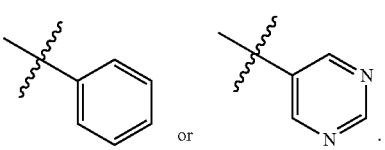 [SMILES: *c1ccccc1 ; *c1cncnc1]

In some embodiments, the compound having a structural Formula (I) (or the salt thereof) has a structural Formula ($I_{C1}$) or ($I_{C2}$):

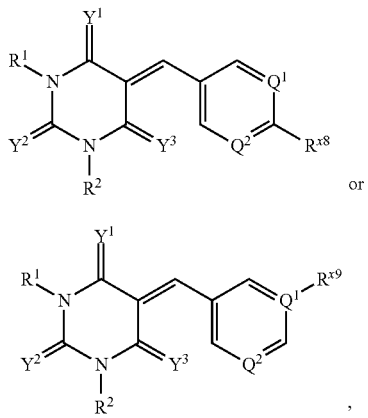

(I$_{C1}$)

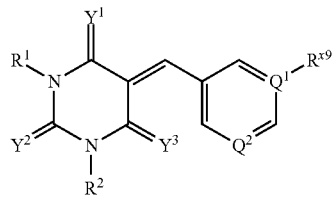

(I$_{C2}$)

wherein:

R$^{x8}$ and R$^{x9}$ are each independently selected from halogen, (e.g., C$_{1-6}$, such as C$_{1-4}$) alkyl, (e.g., C$_{1-6}$, such as C$_{1-4}$) haloalkyl, (e.g., C$_{1-6}$, such as C$_{1-4}$) alkenyl, (e.g., C$_{1-6}$, such as C$_{1-4}$) haloalkenyl, —OH, (e.g., C$_{1-6}$, such as C$_{1-4}$) alkoxy, (e.g., C$_{1-6}$, such as C$_{1-4}$) haloalkoxy, —O-alkylene-C(O)OH, nitro, —NH$_2$, (e.g., C$_{1-6}$, such as C$_{1-4}$) alkylamino, (e.g., C$_{1-6}$, such as C$_{1-4}$) dialkylamino, and (e.g., C$_{1-6}$, such as C$_{1-4}$) haloalkylamino.

In some embodiments of a compound having structural Formula (I$_{C1}$) or (I$_{C2}$) (or a salt thereof), R$^2$ is selected from (e.g., C$_{1-6}$, such as C$_{1-4}$) alkyl, (e.g., C$_{1-6}$, such as C$_{1-4}$) alkenyl, (e.g., C$_{1-6}$, such as C$_{1-4}$) haloalkyl, and (e.g., C$_{1-6}$, such as C$_{1-4}$) haloalkenyl. In some embodiments, Y$^1$ is S. In some embodiments, Y$^3$ is S. In some embodiments, A is

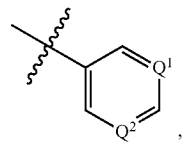

wherein Q$^1$ and Q$^2$ are each independently CH or N. In some embodiments, A is

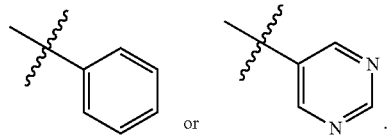 [SMILES: *c1ccccc1 ; *c1cncnc1]

In some embodiments, a compound having structural Formula (I) is selected from those set forth in Table 4, and salts thereof.

TABLE 4

Compounds of Formula (I)

| ID # | Chemical Structure | Chemical Name | Molecular Weight |
|---|---|---|---|
| I-1 | 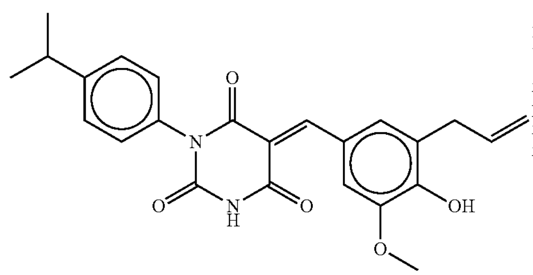 | 2,4,6(1H,3H,5H)-Pyrimidinetrione, 5-[4-hydroxy-3-methoxy-5-(2-propen-1-yl)phenyl]methylene]-1-[4-(1-methylethyl)phenyl]- | 420.465 |
| I-2 | 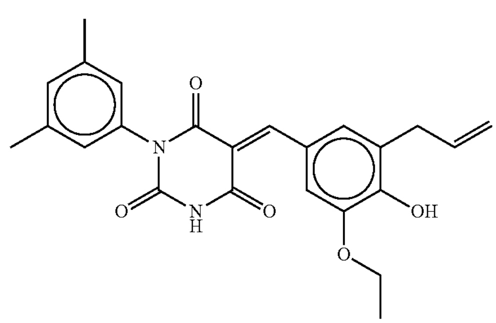 | 2,4,6(1H,3H,5H)-Pyrimidinetrione, 1-(3,5-dimethylphenyl)-5-[[3-ethoxy-4-hydroxy-5-(2-propen-1-yl)phenyl]methylene]- | 420.465 |

TABLE 4-continued

Compounds of Formula (I)

| ID # | Chemical Structure | Chemical Name | Molecular Weight |
| --- | --- | --- | --- |
| I-3 | 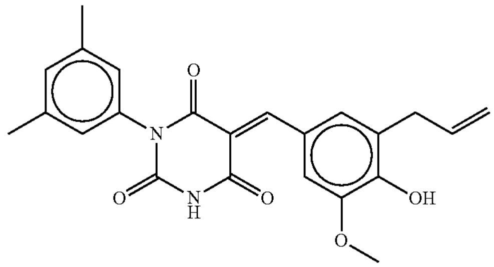 | 2,4,6(1H,3H,5H)-Pyrimidinetrione, 1-(3,5-dimethylphenyl)-5-[[4-hydroxy-3-methoxy-5-(2-propen-1-yl)phenyl]methylene]- | 406.438 |
| I-4 | 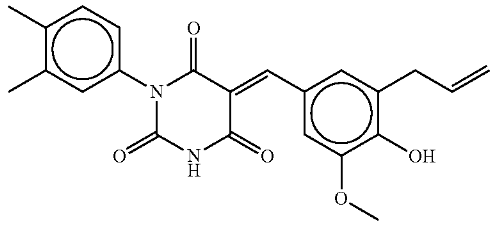 | 2,4,6(1H,3H,5H)-Pyrimidinetrione, 1-(3,4-dimethylphenyl)-5-[4-hydroxy-3-methoxy-5-(2-propen-1-yl)phenyl]methylene]- | 406.438 |
| I-5 | 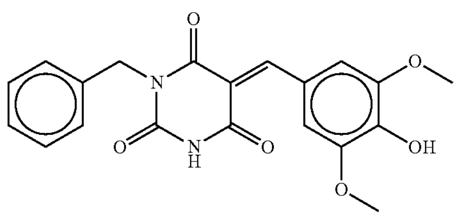 | 2,4,6(1H,3H,5H)-Pyrimidinetrione, 5-[(4-hydroxy-3,5-dimethoxyphenyl)methylene]-1-(phenylmethyl)- | 382.372 |
| I-6 | 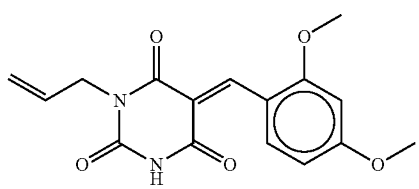 | 2,4,6(1H,3H,5H)-Pyrimidinetrione, 5-[(2,4-dimethoxyphenyl)methylene]-1-(2-propen-1-yl)- | 316.313 |
| I-7 | 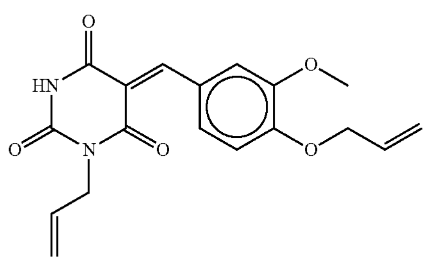 | 2,4,6(1H,3H,5H)-Pyrimidinetrione, 5-[3-methoxy-4-(2-propen-1-yloxy)phenyl]methylene]-1-(2-propen-1-yl)- | 342.351 |
| I-8 | 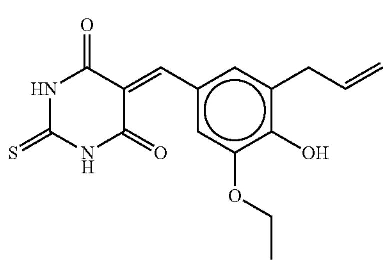 | 4,6(1H,5H)-Pyrimidinedione, 5-[3-ethoxy-4-hydroxy-5-(2-propen-1-yl)phenyl]methylene]dihydro-2-thioxo- | 332.381 |

TABLE 4-continued

Compounds of Formula (I)

| ID # | Chemical Structure | Chemical Name | Molecular Weight |
|---|---|---|---|
| I-9 | 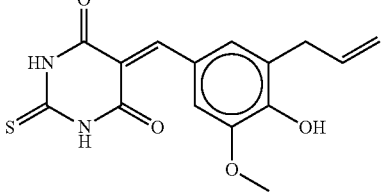 | 4,6(1H,5H)-Pyrimidinedione, dihydro-5-[[4-hydroxy-3-methoxy-5-(2-propen-1-yl)phenyl]methylene]-2-thioxo- | 318.354 |
| I-10 | 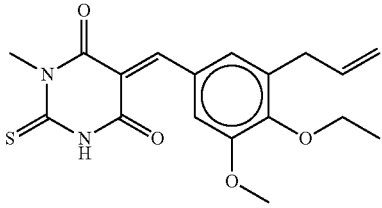 | 4,6(1H,5H)-Pyrimidinedione, 5-[4-ethoxy-3-methoxy-5-(2-propen-1-yl)phenyl]methylene]dihydro-1-methyl-2-thioxo- | 360.435 |
| I-11 | 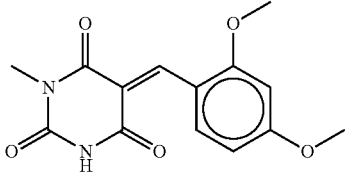 | 2,4,6(1H,3H,5H)-Pyrimidinetrione, 5-[(2,4-dimethoxyphenyl)methylene]-1-methyl-, (5E)- | 290.275 |
| I-12 | 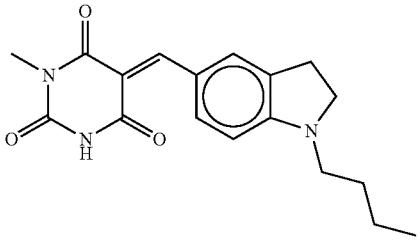 | 2,4,6(1H,3H,5H)-Pyrimidinetrione, 5-[(1-butyl-2,3-dihydro-1H-indol-5-yl)methylene]-1-methyl- | 327.384 |
| I-13 | 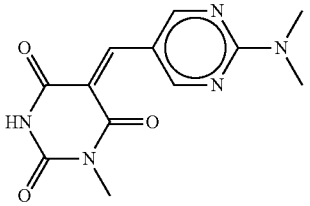 | 2,4,6(1H,3H,5H)-Pyrimidinetrione, 5-[[2-(dimethylamino)-5-pyrimidinyl]methylene]-1-methyl- | 275.268 |
| I-14 | 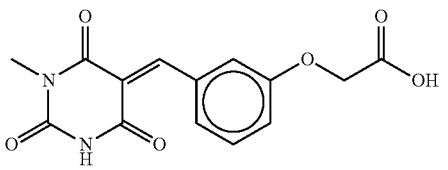 | Acetic acid, 2-[3-[(tetrahydro-1-methyl-2,4,6-trioxo-5(2H)-pyrimidinylidene)methyl phenoxy]- | 304.258 |
| I-15 | 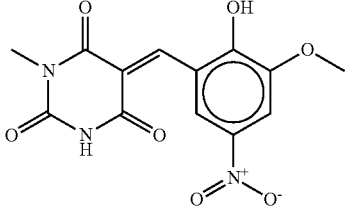 | 2,4,6(1H,3H,5H)-Pyrimidinetrione, 5-[(2-hydroxy-3-methoxy-5-nitrophenyl)methylene]-1-methyl- | 321.245 |

TABLE 4-continued

Compounds of Formula (I)

| ID # | Chemical Structure | Chemical Name | Molecular Weight |
|---|---|---|---|
| I-16 | 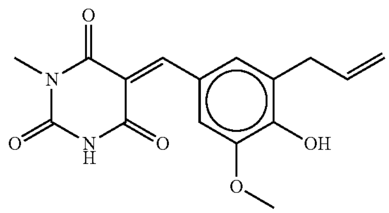 | 2,4,6(1H,3H,5H)-Pyrimidinetrione, 5-[4-hydroxy-3-methoxy-5-(2-propen-1-yl)phenyl]methylene]-1-methyl- | 316.313 |
| I-17 | 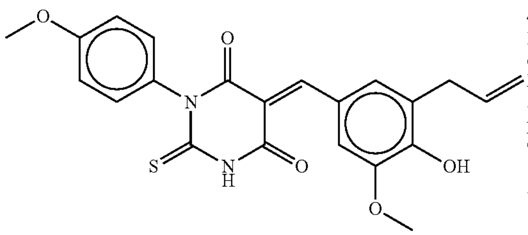 | 4,6(1H,5H)-Pyrimidinedione, dihydro-5-[4-hydroxy-3-methoxy-5-(2-propen-1-yl)phenyl]methylene]-1-Chemical Name (4-methoxyphenyl)-2-thioxo- | 424.478 |
| I-18 | 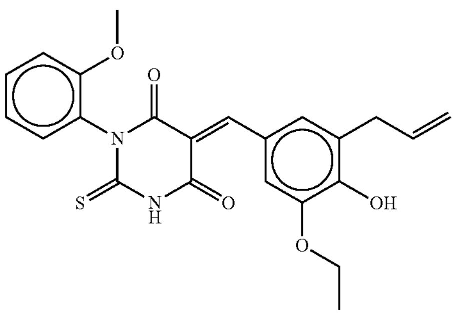 | 4,6(1H,5H)-Pyrimidinedione, 5-[3-ethoxy-4-hydroxy-5-(2-propen-1-yl)phenyl]methylene]dihydro-1-(2-methoxyphenyl)-2-thioxo- | 438.505 |

Compounds and Salts of Formula (II)

In certain aspects, disclosed herein is a compound represented by Formula (II):

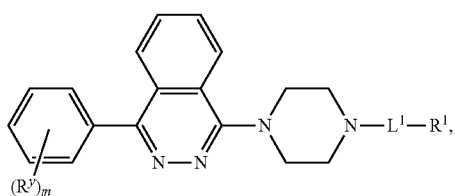

or a salt thereof, wherein:
$R^y$ is each independently alkyl or haloalkyl;
m is 0, 1, or 2;
$L^1$ is selected from bond, —O—, —S—, —N($R^{a1}$)—, —C(O)—, —C(O)-alkylene-, —C(O)-alkylene-O—, -alkylene-C(O)—, -alkylene-C(O)—O—, —C(O)O—, —OC(O)—, —C(O)N($R^{a2}$)—, —N($R^{a3}$)C(O)—, —N($R^{a4}$)C(O)N($R^{a5}$)—, —N($R^{a6}$)C(O)O—, —OC(O)N($R^{a7}$)—, —S(O)$_2$—, —OS(O)—, —S(O)O—, —S(O)—, —OS(O)$_2$—, —S(O)$_2$O—, —N($R^{a8}$)S(O)$_2$—, —S(O)$_2$N($R^{a9}$)—, —N($R^{a10}$)S(O)—, —S(O)N($R^{a11}$)—, —N($R^{a12}$)S(O)$_2$N($R^{a13}$)—, and —N($R^{a14}$)S(O)N($R^{a15}$)—; and
$R^1$ is selected from H, alkyl, haloalkyl, alkoxy, haloalkoxy, alkenyl, haloalkenyl, cycloalkyl, alkylcycloalkyl, halocycloalkyl, aryl (e.g., phenyl), alkylaryl, heteroaryl, —O-aryl, —O-alkylaryl, and —O-heteroaryl.

In some embodiments, the compound having a structural Formula (II) (or the salt thereof) has a structural Formula (IIA):

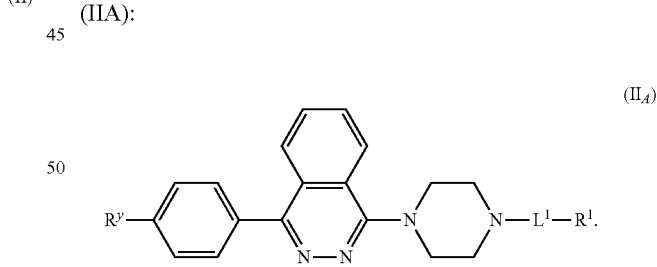

In certain embodiments, for a compound or salt of Formula (II) or (IIA), $R^y$ is $C_1$-$C_6$ (e.g., $C_1$-$C_4$) alkyl (e.g., methyl). In some embodiments, m is 1. In some embodiments, $L^1$ is selected from —C(O)—, —C(O)-alkylene-O—, and —S(O)$_2$—. In some embodiments. $R^1$ is selected from alkyl, cycloalkyl, aryl, alkylaryl, —O-aryl, and —O-alkylaryl.

In some embodiments, a compound having structural Formula (II) is selected from those set forth in Table 5, and salts thereof.

TABLE 5

Compounds of Formula (II)

| ID # | Chemical Structure | Chemical Name | Molecular Weight |
|---|---|---|---|
| II-1 | 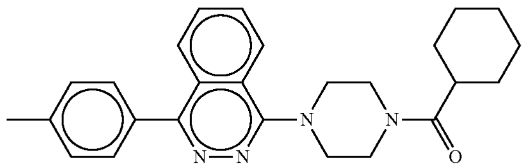 | Methanone, cyclohexyl[4-[4-(4-methylphenyl)-1-phthalazinyl]-1-piperazinyl]- | 414.553 |
| II-2 | 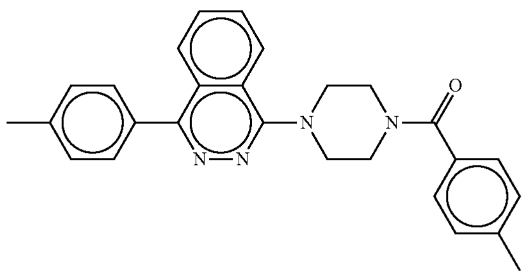 | Methanone, (4-methylphenyl)[4-[4-(4-methylphenyl)-1-phthalazinyl]-1-piperazinyl]- | 422.532 |
| II-3 | 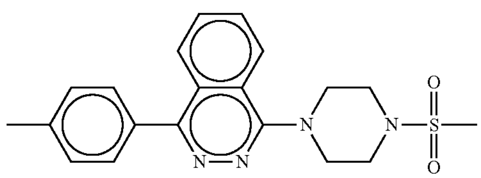 | Phthalazine, 1-(4-methylphenyl)-4-[4-(methylsulfonyl)-1-piperazinyl]- | 382.489 |
| II-4 | 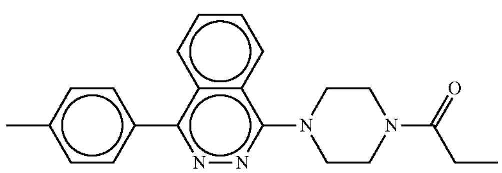 | 1-Propanone, 1-[4-[4-(4-methylphenyl)-1-phthalazinyl]-1-piperazinyl]- | 360.461 |
| II-5 | 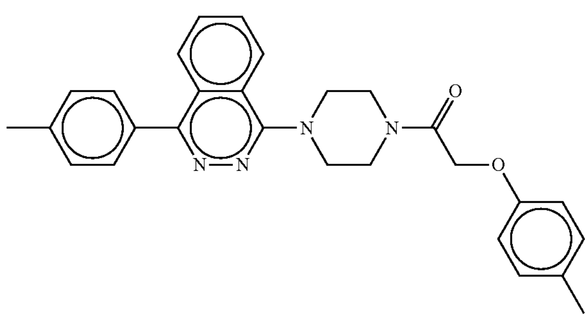 | Ethanone, 2-(4-methylphenoxy)-1-[4-[4-(4-methylphenyl)-1-phthalazinyl]-1-piperazinyl]- | 452.558 |
| II-6 | 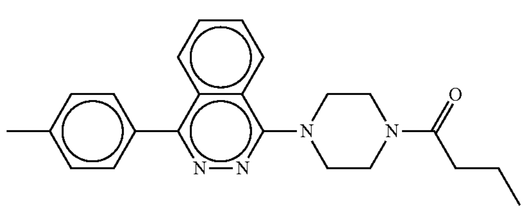 | 1-Butanone, 1-[4-[4-(4-methylphenyl)-1-phthalazinyl]-1-piperazinyl]- | 374.488 |

Compounds and Salts of Formula (III)

In certain aspects, disclosed herein is a compound represented by Formula (III):

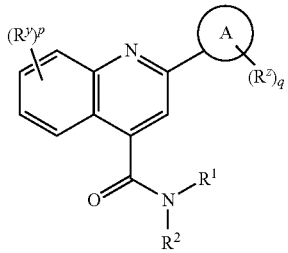

or a salt thereof, wherein:

A is aryl or heteroaryl;

p is 0, 1, or 2;

Ry is each independently alkyl or haloalkyl;

q is 0, 1, or 2;

Rz is each independently alkyl or haloalkyl; and $R^1$ and $R^2$ are each independently selected from H, optionally substituted aryl, —NH—C(O)—NH-cycloalkyl (e.g., adamantyl), —C(O)—NH-cycloalkyl, and —NH—C(O)-cycloalkyl; or, alternatively, $R^1$ and $R^2$ join together with the nitrogen atom to which they are attached to form N-heterocyclyl (e.g., piperazinyl) or —N=$R^c$, wherein $R^c$ is an optionally substituted aryl or optionally substituted heteroaryl.

In certain embodiments, for a compound or salt of Formula (III), $R^1$ and $R^2$ join together with the nitrogen atom to which they are attached to form

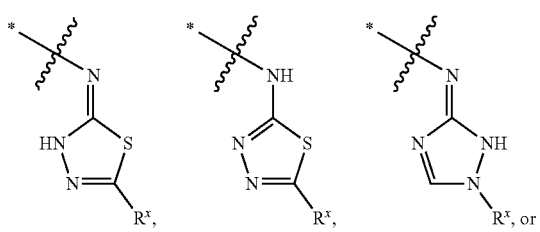

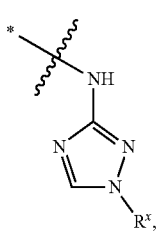

wherein $R^x$ is selected from alkyl, haloalkyl, -alkylene-OH, -alkylene-O-alkyl, -alkylene-aryl, and -alkylene-arylene-alkyl. In some embodiments, $R^1$ and $R^2$ join together with the nitrogen atom to which they are attached to form

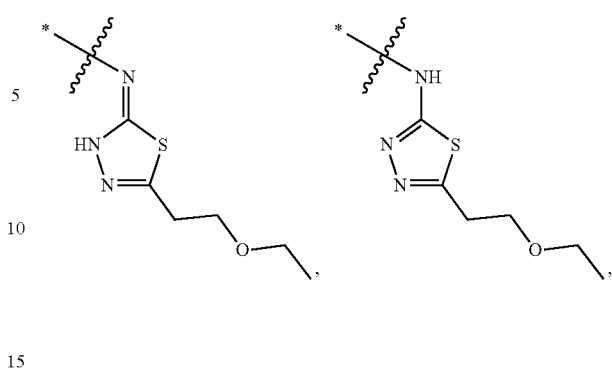

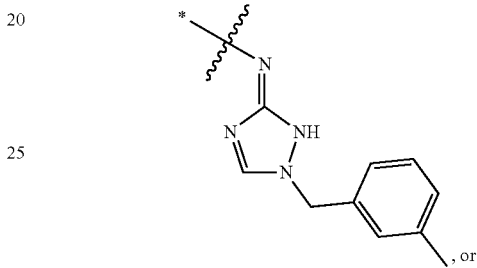

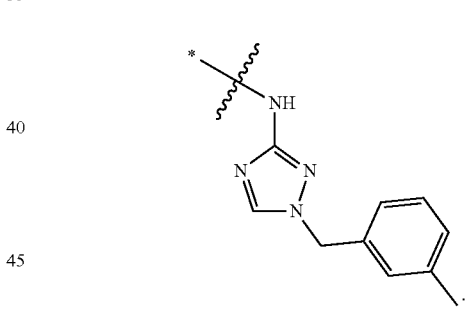

In some embodiments, $R^1$ and $R^2$ join together with the nitrogen atom to which they are attached to form an optionally substituted piperazinyl. In some embodiments, A is pyridinyl

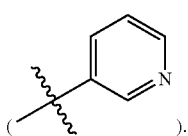

In some embodiments, a compound having structural Formula (III) is selected from those set forth in Table 6, and salts thereof.

TABLE 6

| Compounds of Formula (III) | | | |
|---|---|---|---|
| ID # | Chemical Structure | Chemical Name | Molecular Weight |
| III-1 | | Methanone, [4-(4-methoxyphenyl)-1-piperazinyl][2-(2-thienyl)-4-quinolinyl]- | 429.545 |
| III-2 | | 4-Quinolinecarboxamide, 6-methyl-N-[1-[(3-methylphenyl)methyl]-1H-1,2,4-triazol-3-yl]-2-(3-pyridinyl)- | 434.503 |
| III-3 | | 4-Quinolinecarboxamide, 2-(3,4-dimethylphenyl)-N-[4-[(3,5-dimethyl-1H-pyrazol-1-yl)methyl]phenyl]- | 460.581 |

TABLE 6-continued

Compounds of Formula (III)

| ID # | Chemical Structure | Chemical Name | Molecular Weight |
|---|---|---|---|
| III-4 | 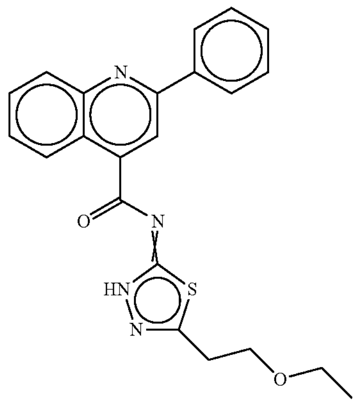 | 4-Quinolinecarboxamide, N-[5-(2-ethoxyethyl)-1,3,4-thiadiazol-2-yl]-2-phenyl- | 404.495 |
| III-5 | 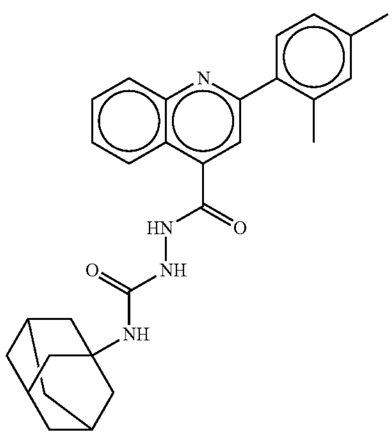 | 4-Quinolinecarboxylic acid, 2-(2,4-dimethylphenyl)-, 2-[(tricyclo[3.3.1.1$^{3,7}$]dec-1-ylamino)carbonyl]hydrazide | 468.601 |

Compounds and Salts of Formula (IV)

In certain aspects, disclosed herein is a compound represented by Formula (IV):

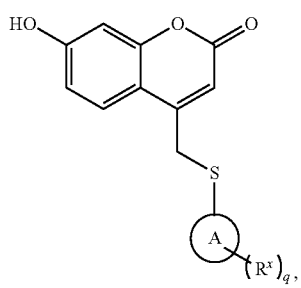

(IV)

or a salt thereof, wherein:

A is heteroaryl;

q is 0, 1, 2, or 3; and

R$^x$ is selected from alkyl, haloalkyl, alkoxyl, haloalkoxyl, —SH, alkylthio, aryl, and alkoxylaryl.

In some embodiments, a compound having structural Formula (IV) is selected from those set forth in Table 7, and salts thereof.

TABLE 7

Compounds of Formula (IV)

| ID # | Chemical Structure | Chemical Name | Molecular Weight |
|---|---|---|---|
| IV-1 | 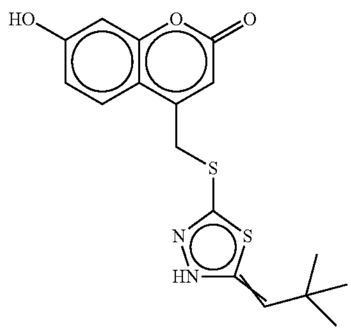 | 2H-1-Benzopyran-2-one, 4-[[[5-[(1,1-dimethylethyl)amino]-1,3,4-thiadiazol-2-yl]thio]methyl]-7-hydroxy- | 363.464 |
| IV-2 | 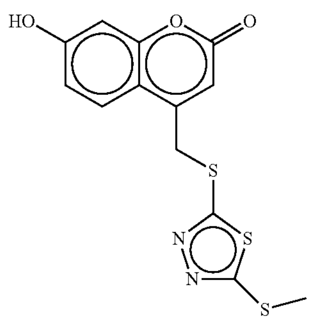 | 2H-1-Benzopyran-2-one, 7-hydroxy-4-[[[5-(methylthio)-1,3,4-thiadiazol-2-yl]thio]methyl]- | 338.435 |
| IV-3 | 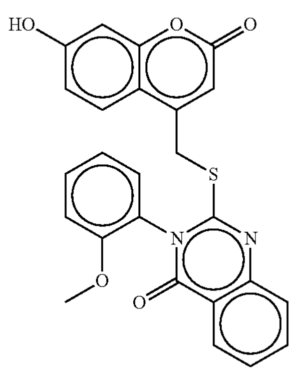 | 4(3H)-Quinazolinone, 2-[[(7-hydroxy-2-oxo-2H-1-benzopyran-4-yl)methyl]thio]-3-(2-methoxyphenyl)- | 458.495 |
| IV-4 | 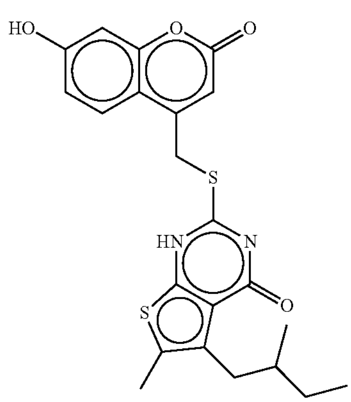 | Thieno[2,3-d]pyrimidin-4(1H)-one, 2-[[(7-hydroxy-2-oxo-2H-1-benzopyran-4-yl)methyl]thio]-6-methyl-5-(2-methylbutyl)- | 442.562 |

Compounds and Salts of Formula (V)

In certain aspects, disclosed herein is a compound represented by Formula (V):

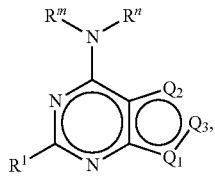

or a salt thereof, wherein:
R[1] is H or optionally substituted aryl;
R$^m$ and R$^n$ join together with the nitrogen atom to which they are attached to form N-heterocyclyl, wherein the N-heterocyclyl is optionally substituted with one or more substituents selected from alkyl, —S(O)H, —S(O)$_2$H, —S(O)-alkyl, and —S(O)$_2$-alkyl;

$Q_1$ is NR$^{a1}$, CR$^{b1}$R$^{b2}$, or S;
$Q_3$ is N or CR$^{b3}$; and
$Q_2$ is NR$^{a2}$ or CR$^{b4}$R$^{b5}$, wherein:
R$^{a1}$, R$^{a2}$, R$^{b1}$, R$^{b2}$, R$^{b3}$, R$^{b4}$, and R$^{b5}$ are each independently selected from H, optionally substituted aryl, optionally substituted alkylaryl, and optionally substituted arylalkyl.

In certain embodiments, for a compound or salt of Formula (V), $Q^1$ is CR$^{b1}$R$^{b2}$ or S. In some embodiments, $Q^3$ is CR$^{b3}$.

In some embodiments, a compound having structural Formula (V) is selected from those set forth in Table 8, and salts thereof.

TABLE 8

Compounds of Formula (V)

| ID # | Chemical Structure | Chemical Name | Molecular Weight |
|---|---|---|---|
| V-1 | 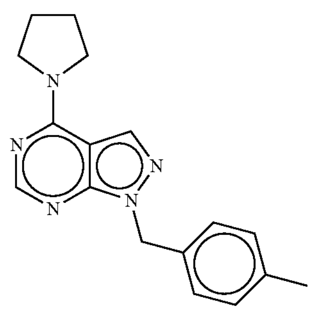 | 1H-Pyrazolo[3,4-d]pyrimidine, 1-[(4-methylphenyl)methyl]-4-(1-pyrrolidinyl)- | 293.374 |
| V-2 | 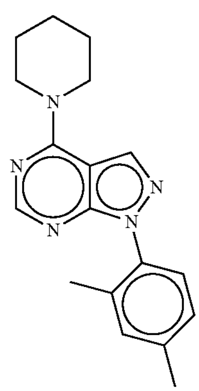 | 1H-Pyrazolo[3,4-d]pyrimidine, 1-(2,4-dimethylphenyl)-4-(1-piperidinyl)- | 307.401 |
| V-3 | 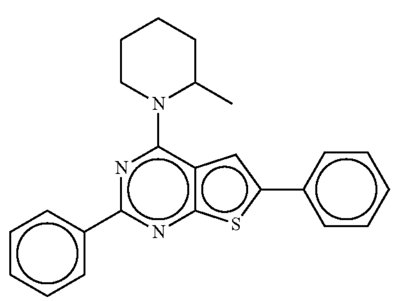 | Thieno[2,3-d]pyrimidine, 4-(2-methyl-1-piperidinyl)-2,6-diphenyl- | 385.536 |

TABLE 8-continued

Compounds of Formula (V)

| ID # | Chemical Structure | Chemical Name | Molecular Weight |
|------|-------------------|---------------|------------------|
| V-4 | 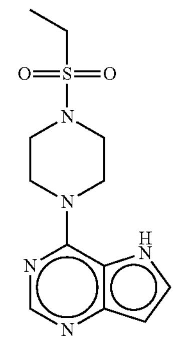 | 5H-Pyrrolo[3,2-d]pyrimidine, 4-[4-(ethylsulfonyl)-1-piperazinyl]- | 295.368 |

Compounds and Salts of Formula (VI)

In certain aspects, disclosed herein is a compound represented by Formula (VI):

(VI)

or a salt thereof, wherein:

$L^0$ is selected from —C(O)—, —O—, —S—, —C(O)O—, —OC(O)—, —S(O)—, —S(O)$_2$—, —NH—, and

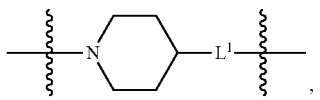

wherein $L^1$ is selected from —C(O)—, —O—, —S—, —C(O)O—, —OC(O)—, —S(O)—, —S(O)$_2$—, and —NH—;

p, q, and m are each independently 0, 1, or 2;

$R^x$, $R^y$, and $R^z$ are each independently selected from alkyl, haloalkyl, alkoxy, haloalkoxy, nitro, cyano, —OH, —C(O)OH, or -alkylene-C(O)OH;

A is aryl or heteroaryl;

$L^2$ is alkylene, —C(O)—, —O—, —S—, —C(O)O—, —OC(O)—, —S(O)—, —S(O)$_2$—, —N(H)S(O)$_2$—, —S(O)$_2$N(H)—, -alkylene-N(H)S(O)$_2$—, —S(O)$_2$N(H)-alkylene-, —NH—, —N═, and —CH═N—N═; and B is an optionally substituted aryl or optionally substituted heteroaryl.

In certain embodiments, for a compound or salt of Formula (VI), $L^0$ is

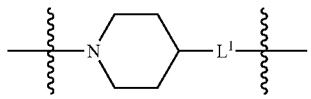

In some embodiments, A is phenyl or piperazinyl. In some embodiments, B is selected from

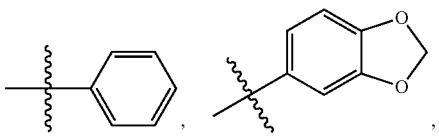

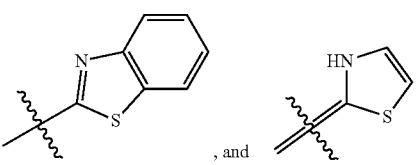

, and .

In some embodiments, $L^2$ is selected from alkylene, —S(O)$_2$N(H)-alkylene-, and —CH═N—N═. In some embodiments, p is 0. In some embodiments, p is 1. In some embodiments, p is 2. In some embodiments, q is 0. In some embodiments, m is 0. In some embodiments, m is 2. In some embodiments, $R^x$ is each independently cyano, alkyl, alkoxy, and nitro. In some embodiments, $R^z$ is each independently —OH, —C(O)OH, or -alkylene-C(O)OH.

In some embodiments, a compound having structural Formula (VI) is selected from those set forth in Table 9, and salts thereof.

TABLE 9

Compounds of Formula (VI)

| ID # | Chemical Structure | Chemical Name | Molecular Weight |
|---|---|---|---|
| VI-1 | 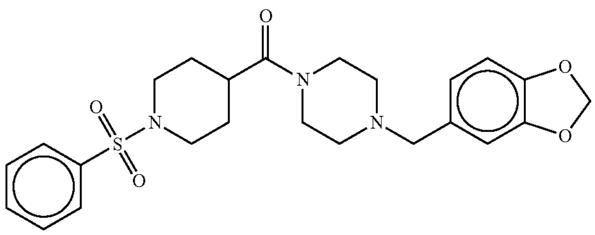 | Methanone, [4-(1,3-benzodioxol-5-ylmethyl)-1-piperazinyl][1-(phenylsulfonyl)-4-piperidinyl]- | 471.579 |
| VI-2 | 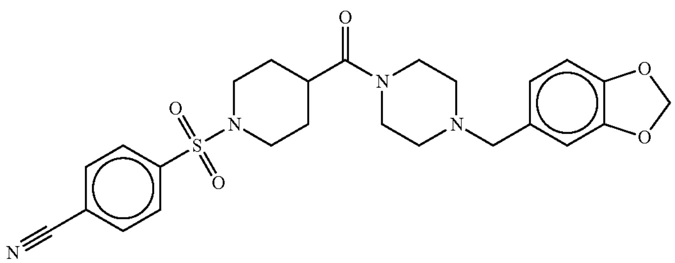 | Benzonitrile, 4-[[4-[[4-(1,3-benzodioxol-5-ylmethyl)-1-piperazinyl]carbonyl]-1-piperidinyl]sulfonyl]- | 496.589 |
| VI-3 | 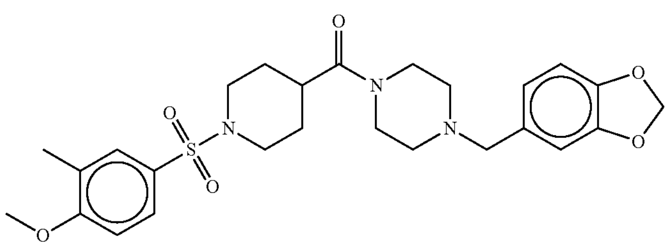 | Methanone, [4-(1,3-benzodioxol-5-ylmethyl)-1-piperazinyl][1-[(4-methoxy-3-methylphenyl)sulfonyl]-4-piperidinyl]- | 515.632 |
| VI-4 | 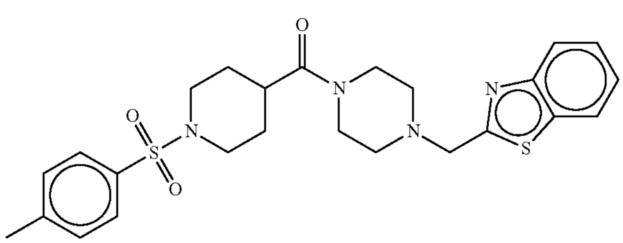 | Methanone, [4-(2-benzothiazolylmethyl)-1-piperazinyl][1-[(4-methylphenyl)sulfonyl]-4-piperidinyl]- | 498.674 |
| VI-5 | 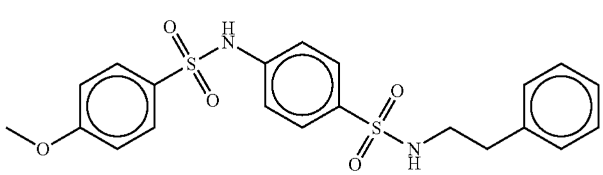 | Benzenesulfonamide, 4-methoxy-N-[4-[[[(2-phenylethyl)amino]sulfonyl]phenyl]- | 446.550 |
| VI-6 | 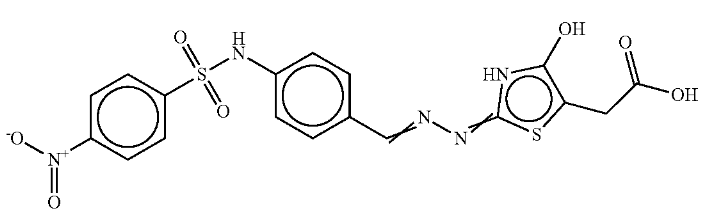 | 5-Thiazoleacetic acid, 4,5-dihydro-2-[2-[[4-[[(4-nitrophenyl)sulfonyl]oxy]phenyl]methylene]hydrazinyl]-4-oxo- | 478.464 |

Other Compounds and Salts Thereof

In some embodiments, a compound disclosed herein is selected from those set forth in Table 10, and salts thereof.

TABLE 10

Other compounds

| ID # | Chemical Structure | Chemical Name | Molecular Weight |
|---|---|---|---|
| VII-5 | 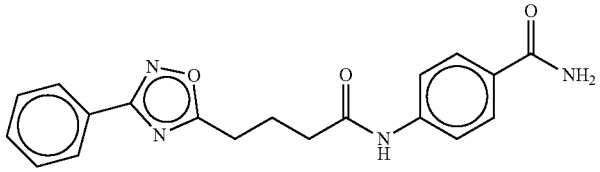 | 1,2,4-Oxadiazole-5-butanamide, N-[4-(aminocarbonyl)phenyl]-3-phenyl- | 350.378 |
| VII-6 | 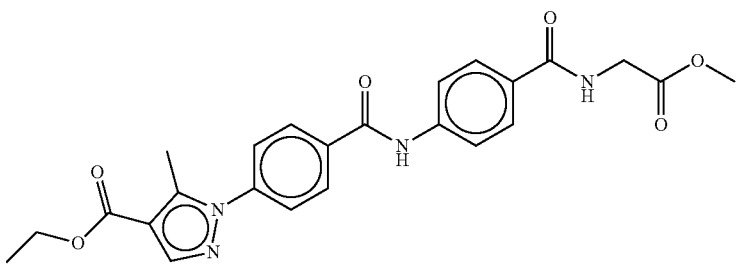 | 1H-Pyrazole-4-carboxylic acid, 1-[4-[[[4-[[(2-methoxy-2-oxoethyl)amino]carbonyl]phenyl]amino]carbonyl]phenyl]-5-methyl-, ethyl ester | 464.478 |
| VII-7 | 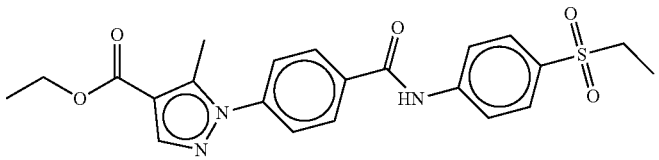 | 1H-Pyrazole-4-carboxylic acid, 1-[4-[[[4-(ethylsulfonyl)phenyl]amino]carbonyl]phenyl]-5-methyl-, ethyl ester | 441.509 |
| VII-8 | 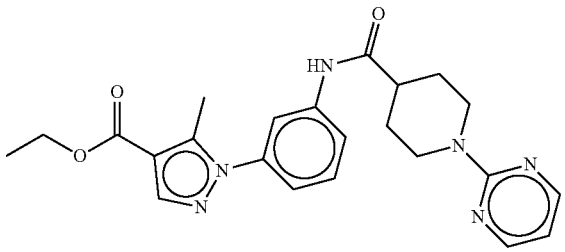 | 1H-Pyrazole-4-carboxylic acid, 5-methyl-1-[3-[[[1-(2-pyrimidinyl)-4-piperidinyl]carbonyl]amino]phenyl]-, ethyl ester | 434.500 |
| VII-9 | 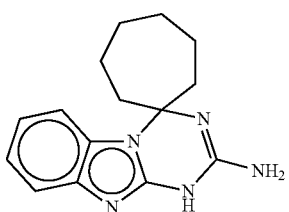 | Spiro[cycloheptane-1,4'(1'H)-[1,3,5]triazino[1,2-a]benzimidazol]-2'-amine | 269.352 |
| VII-10 | 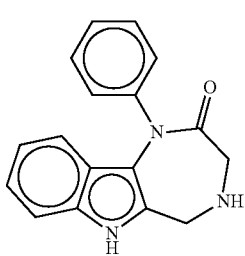 | 1,4-Diazepino[6,5-b]indol-2(1H)-one, 3,4,5,6-tetrahydro-1-phenyl- | 277.327 |

TABLE 10-continued

Other compounds

| ID # | Chemical Structure | Chemical Name | Molecular Weight |
|---|---|---|---|
| VII-11 | 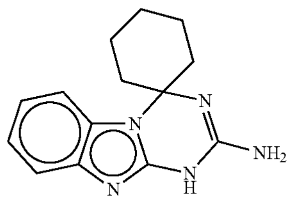 | Spiro[cyclohexane-1,4'(3'H)-[1,3,5]triazino[1,2-a]benzimidazol]-2'-amine | 255.325 |
| VII-12 | 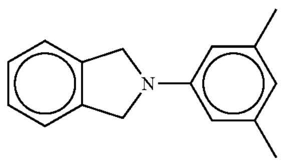 | 1H-Isoindole, 2-(3,5-dimethylphenyl)-2,3-dihydro- | 223.319 |
| VII-13 | 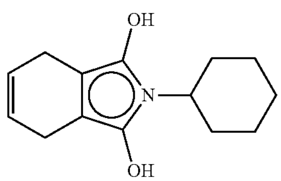 | 1H-Isoindole-1,3(2H)-dione, 2-cyclohexyl-3a,4,7,7a-tetrahydro- | 233.311 |
| VII-14 | 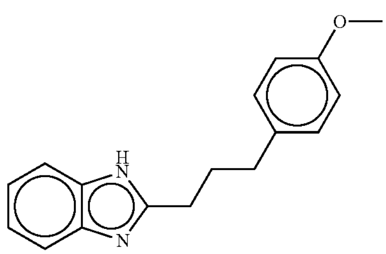 | 1H-Benzimidazole, 2-[3-(4-methoxyphenyl)propyl]- | 266.344 |
| VII-15 | 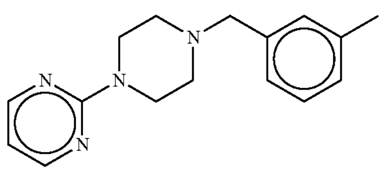 | Pyrimidine, 2-[4-[(3-methylphenyl)methyl]-1-piperazinyl]- | 268.364 |
| VII-16 | 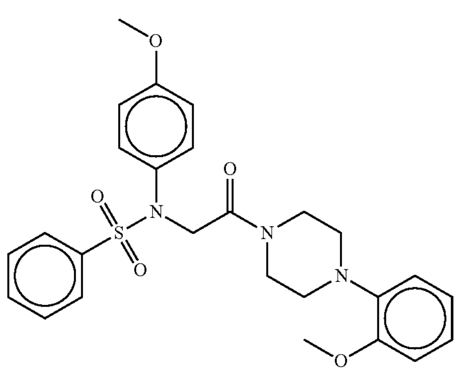 | Benzenesulfonamide, N-(4-methoxyphenyl)-N-[2-[4-(2-methoxyphenyl)-1-piperazinyl]-2-oxoethyl]- | 495.601 |

TABLE 10-continued

| | Other compounds | | |
|---|---|---|---|
| ID # | Chemical Structure | Chemical Name | Molecular Weight |
| VII-17 | | 2H-1,4-Benzothiazin-3(4H)-one, 2-[2-[4-(diphenylmethyl)-1-piperazinyl]-2-oxoethyl]- | 457.599 |
| VII-18 | | Piperazine, 1-(1-naphthalenylcarbonyl)-4-(2-thienylcarbonyl)- (9CI) | 350.443 |
| VII-19 | | Pregna-1,4-diene-3,20-dione, 21-(3-carboxy-1-oxopropoxy)-11,17-dihydroxy-, (11β)- | 460.523 |
| VII-20 | | 1,4-Benzenedicarboxamide, $N^1,N^4$-diethyl-$N^1$,$N^4$-bis(phenylmethyl)- | 400.522 |
| VII-21 | | 2(1H)-Phthalazineacetamide, N-[2-(1,2-dimethyl-1H-indol-3-yl)ethyl]-4-[4-methyl-3-(4-morpholinylsulfonyl)phenyl]-1-oxo- | 613.740 |

TABLE 10-continued

| | Other compounds | | |
|---|---|---|---|
| ID # | Chemical Structure | Chemical Name | Molecular Weight |
| VII-22 | 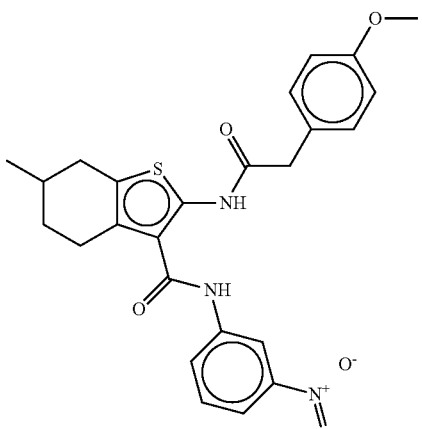 | Benzo[b]thiophene-3-carboxamide, 4,5,6,7-tetrahydro-2-[[2-(4-methoxyphenyl)acetyl]amino]-6-methyl-N-(3-nitrophenyl)- | 479.558 |
| VII-23 | 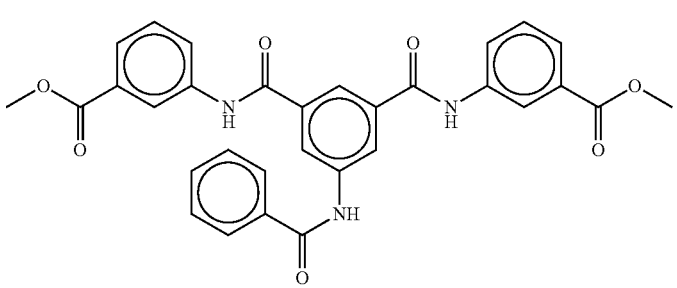 | Benzoic acid, 3,3'-[[5-(benzoylamino)-1,3-phenylene]bis(carbonylimino)]bis-, dimethyl ester (9CI) | 551.555 |
| VII-24 | 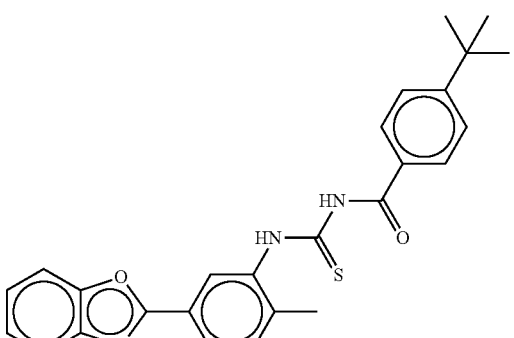 | Benzamide, 4-(1,1-dimethylethyl)-N-[[(2-methyl-5-oxazolo[4,5-b]pyridin-2-ylphenyl)amino]thioxomethyl]- | 444.560 |
| VII-26 | 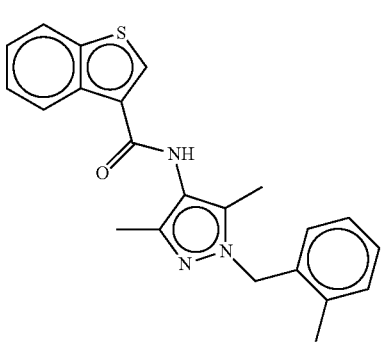 | Benzo[b]thiophene-3-carboxamide, N-[3,5-dimethyl-1-[(2-methylphenyl)methyl]-1H-pyrazol-4-yl]- | 375.497 |

In some embodiments, a compound disclosed herein is selected from those (or any subset thereof) set forth in any one or combination of Tables 1 through 10, and salts thereof.

For the synthesis methods of the compounds disclosed herein, see, e.g., WO2009031709 A1; *Journal fuer Praktische Chemie* (Leipzig), 323 (2), 3030310, 1981; *European Journal of Medicinal Chemistry*, 47, 138-142, 2012; *Pharmaceutical Chemistry Journal*, 41, 70-473, 2007; *A.M.A.J. Diseases Children*, 97, 66-71, 1959; WO2003072099 A1; *Chemiker-Zeitung*, 111, 159-166, 1987; *Journal of Heterocyclic Chemistry*, 25(3), 959-968, 1988; and *Russian Chemical Bulletin*, 52(6), 1386-1398, 2003, each of which is incorporated herein by reference.

Compounds of the present invention also include crystalline and amorphous forms of those compounds, pharmaceuically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley and Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*. 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Compositions

The disclosure provides compositions of compounds disclosed herein and salts thereof.

In certain aspects, the present disclosure provides a composition for treating hair loss or hair thinning comprising a compound having a structure of Formula (VII$_B$):

Formula (VII$_B$)

or a pharmaceutically or cosmetically acceptable salt thereof, wherein:

A is selected from a triazole, wherein the triazole is optionally substituted with one or more $R^{10}$;

B is selected from O, NH, S;

n is selected from 0, 1, 2, and 3;

each $R^{10}$ is independently selected at each occurrence from halogen, $C_{1-6}$ alkyl, $C_{2-6}$ alkenyl, and $C_{2-6}$ alkynyl, —$OR^{11}$, —$SR^{11}$, —$NO_2$, =O, =NH, —CN, —C(O)$R^{11}$, —C(O)O$R^{11}$, —OC(O)$R^{11}$, —OC(O)N($R^{11}$)$_2$, —N$R^{11}$S(O)$_2R^{11}$, —C(O)N($R^{11}$)$_2$, —N($R^{11}$)C(O)$R^{11}$, —N($R^{11}$)C(O)N($R^{11}$)$_2$, —N($R^{11}$)C(O)O$R^{11}$, —S(O)$_2$($R^{11}$), —S(O)$_2$N($R^{11}$)$_2$, $C_{1-10}$ alkyl, $C_3$-$C_{12}$ carbocycle and 5- to 12-membered heterocycle;

each $R^{11}$ is independently selected at each occurrence from hydrogen; $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents selected from =O, and phenyl, wherein the phenyl is optionally substituted with one or more substituents independently selected from —C(O)$R^{12}$, and —S(O)$_2$($R^{12}$);

each $R^{12}$ is independently selected at each occurrence from hydrogen, halogen, —NH$C_{1-10}$ alkyl, —N($C_{1-10}$ alkyl)$_2$, $C_{1-10}$ alkyl, —$C_{1-10}$ haloalkyl, —O—$C_{1-10}$ alkyl, $C_{2-10}$ alkenyl, $C_{2-10}$ alkynyl, $C_{32}$ carbocycle, and 3- to 12-membered heterocycle;

each $R^{20}$ is independently selected from halogen, —OH, —CN, —NO$_2$, —NH$_2$, —NH$C_{1-10}$ alkyl, —N($C_{1-10}$ alkyl)$_2$, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle, wherein a weight % of the compound in the composition has at least about 0.0001% to at most about 10% by weight relative to the total weight of the composition.

In another aspects, the present disclosure provides a composition for treating hair loss or hair thinning comprising a compound having a structure of Formula (VII$_B$):

Formula (VII$_B$)

or a pharmaceutically or cosmetically acceptable salt thereof, wherein:

A is selected from a triazole, wherein the triazole is optionally substituted with one or more $R^{10}$;

B is selected from O, NH, S;

n is selected from 0, 1, 2, and 3;

each $R^{10}$ is independently selected at each occurrence from halogen, $C_{1-6}$ alkyl, $C_{2-6}$ alkenyl, and $C_{2-6}$ alkynyl, —OR$^{11}$, —SR$^{11}$, —NO$_2$, =O, =NH, —CN, —C(O)R$^{11}$, —C(O)OR$^{11}$, —OC(O)R$^{11}$, —OC(O)N(R$^{11}$)$_2$, —NR$^{11}$S(O)$_2$R$^{11}$, —C(O)N(R$^{11}$)$_2$, —N(R$^{11}$)C(O)R$^{11}$, —N(R$^{11}$)C(O)N(R$^{11}$)$_2$, —N(R$^{11}$)C(O)OR$^{11}$, —S(O)$_2$(R$^{11}$), —S(O)$_2$N(R$^{11}$)$_2$, C$_{1-10}$ alkyl, C$_3$-C$_{12}$ carbocycle and 5- to 12-membered heterocycle;

each R$^{11}$ is independently selected at each occurrence from hydrogen; C$_{1-6}$ alkyl, C$_{2-6}$ alkenyl, C$_{2-6}$ alkynyl, C$_{3-12}$ carbocycle, and 3- to 12-membered heterocycle, each of which is optionally substituted with one or more substituents selected from =O, and phenyl, wherein the phenyl is optionally substituted with one or more substituents independently selected from —C(O)R$^{12}$, and —S(O)$_2$(R$^{12}$);

each R$^{12}$ is independently selected at each occurrence from hydrogen, halogen, —NHC$_{1-10}$ alkyl, —N(C$_{1-10}$ alkyl)$_2$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

each R$^{20}$ is independently selected from halogen, —OH, —CN, —NO$_2$, —NH$_2$, —NHC$_{1-10}$ alkyl, —N(C$_{1-10}$ alkyl)$_2$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle.

In some embodiments, the compound of Formula (VII$_B$) is represented by

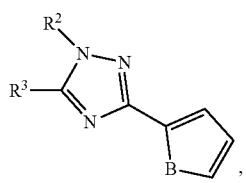

Formula (VII$_B$-A)

or a pharmaceutically or cosmetically acceptable salt thereof, wherein;
B is selected from oxygen and sulfur;
R$^2$ is —S(O)$_2$(R$^{11}$);
R$^3$ is —SR$^1$;
wherein each R$^{11}$ is selected from C$_{1-6}$ alkyl.

In some embodiments, B is oxygen. In some embodiments, R$^{11}$ is C$_1$alkyl.

In some embodiments, the compound of Formula (VII$_B$) is represented by

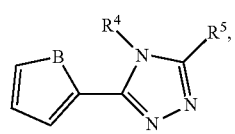

Formula (VII$_B$-B)

or a pharmaceutically or cosmetically acceptable salt thereof, wherein;
B is selected from oxygen and sulfur;
R$^4$ is C$_{1-6}$ alkyl;
R$^5$ is —SR$^{11}$; and
wherein R$^{11}$ is selected from C$_{1-6}$ alkyl, wherein C$_{1-6}$ alkyl is optionally substituted with one or more substituents selected from =O, and phenyl, wherein the phenyl is optionally substituted with one or more substituents independently selected from —S(O)$_2$(R$^{12}$), and wherein R$^{12}$ is a 5-membered heterocycle.

In some embodiments, B is oxygen. In some embodiments, R$^4$ is C$_2$ alkyl. In some embodiments, R$^{12}$ is

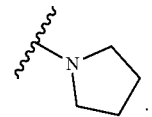 [SMILES: *N1CCCC1]

In some embodiments, the compound of Formula (VII$_B$) is represented by

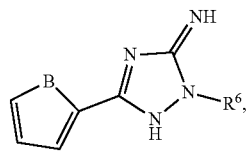

Formula (VII$_B$-C)

or a pharmaceutically or cosmetically acceptable salt thereof, wherein;
B is selected from oxygen and sulfur;
R$^6$ is —S(O)$_2$(R$^{11}$); and
wherein R$^{11}$ is selected from C$_{1-6}$ alkyl.

In some embodiments, B is oxygen. In some embodiments, R$^{11}$ is C$_2$ alkyl.

In some embodiments, the triazole is selected from

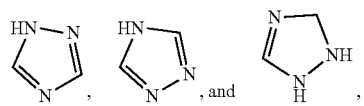

each of which is optionally substituted with one or more R$^{10}$.

In some embodiments, B is oxygen.

In some embodiments, R$^{10}$ is selected from C$_{1-6}$ alkyl, —SR$^{11}$, =NH, and —S(O)$_2$(R$^{11}$). In some embodiments, R$^{11}$ is selected from C$_{1-2}$ alkyl, and

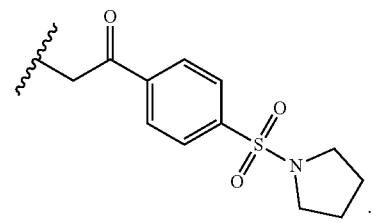 [SMILES: *CC(=O)c1ccc(S(=O)(=O)N2CCCC2)cc1]

In some embodiments, R$^{10}$ is C$_{1-6}$ alkyl. In some embodiments, R$^{10}$ is C$_2$ alkyl.

In some embodiments, R$^{10}$ is —SR$^{11}$. In some embodiments, R$^{11}$ is C$_1$alkyl. In some embodiments, R$^{11}$ is

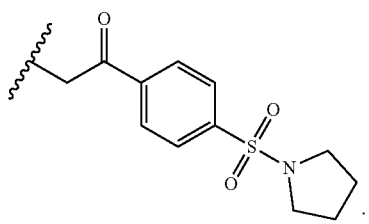

In some embodiments, $R^{10}$ is =NH.

In some embodiments, $R^{10}$ is —S(O)$_2$($R^{11}$). In some embodiments, $R^{11}$ is $C_2$ alkyl.

In some embodiments, n is 0. In some embodiments, $R^4$ is $C_2$ alkyl.

In some embodiments, a compound having structural Formula (VII$_B$) is selected from:

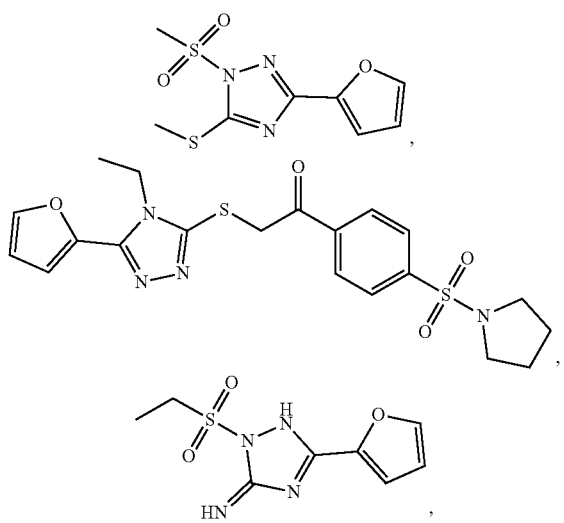

or a pharmaceutically or cosmetically acceptable salt thereof.

In some embodiments, the composition is for preventing or treating hair loss or hair thinning comprising a compound having a structure of Formula (VII$_B$). In some embodiments, a weight % of the compound in the composition ranges from about 0.005% to about 10.0% by weight relative to the total weight of the composition. In some embodiments, a weight % of the compound in the composition ranges from about 0.01% to about 5%. In some embodiments, a weight % of the compound in the composition ranges from about 0.01% to about 2.0%. In some embodiments, a weight % of the compound in the composition ranges from about 0.0001% to about 10% by weight relative to the total weight of the composition. In some embodiments, a weight % of the compound in the composition is at least about 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition is at most about 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition ranges from about 0.0001 to 10, 0.0005 to 9, 0.001 to 8, 0.005 to 7, 0.01 to 6, 0.02 to 5, 0.03 to 4, 0.04 to 3, 0.05 to 2, 0.06 to 1, 0.07 to 0.9, 0.08 to 0.8, 0.09 to 0.7, 0.1 to 0.6, 0.2 to 0.5, or 0.3 to 0.4% by weight relative to the total weight of the composition.

In certain aspects, the present disclosure also provides a composition for treating hair loss or hair thinning comprising a compound having a compound having a structure of Formula (VII$_A$):

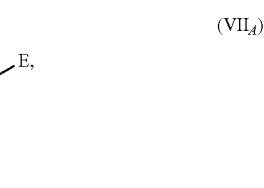

(VII$_A$)

or a pharmaceutically or cosmetically acceptable salt thereof, wherein:

E is selected from hydrogen, $C_5$-$C_8$ aryl, and heteroaryl;

$R^1$ is selected from hydrogen, $C_{1-6}$ alkyl, $C_{1-6}$ haloalkyl, —S—$C_{1-6}$ alkyl, —S—$C_{1-6}$ haloalkyl, —S(O)(O)$R^a$;

wherein $R^a$ is selected from hydrogen, $C_{1-6}$ alkyl, and $C_{1-6}$ haloalkyl; and $R^2$ is selected from —C(O)OH, —C(O)O—$R^c$, and —C(O)O—$C_{1-6}$ haloalkyl, wherein a weight % of the compound in the composition is at least about 0.0001% to at most about 10% by weight relative to the total weight of the composition.

In another aspects, the present disclosure provides a composition for treating hair loss or hair thinning comprising a compound having a compound having a structure of Formula (VII$_A$):

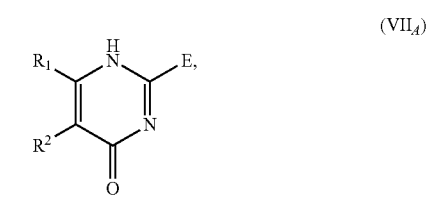

(VII$_A$)

or a pharmaceutically or cosmetically acceptable salt thereof, wherein:

E is selected from hydrogen, $C_5$-$C_8$ aryl, and heteroaryl;

$R^1$ is selected from hydrogen, $C_{1-6}$ alkyl, $C_{1-6}$ haloalkyl, —S—$C_{1-6}$ alkyl, —S—$C_{1-6}$ haloalkyl, —S(O)(O)$R^a$;

wherein $R^a$ is selected from hydrogen, $C_{1-6}$ alkyl, and $C_{1-6}$ haloalkyl; and $R^2$ is selected from —C(O)OH, —C(O)O—$R^c$, and —C(O)O—$C_{1-6}$ haloalkyl.

In some embodiments, E is $C_5$-$C_8$ aryl. In some embodiments, E is phenyl.

In some embodiments, $R^1$ is S(O)(O)$R^a$. In some embodiments, $R^a$ is $C_1$alkyl. In some embodiments, $R^1$ is —S(O)(O)CH$_3$.

In some embodiments, $R^2$ is —C(O)O—$R^c$. In some embodiments, $R^2$ is —C(O)OCH$_3$.

In some embodiments, a compound having structural Formula (VII$_A$) is

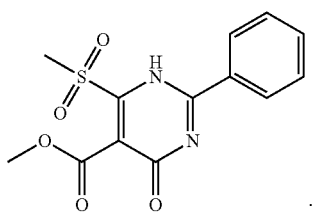 [SMILES: COC(=O)c1c(S(C)(=O)=O)[nH]c(-c2ccccc2)nc1=O]

In some embodiments, the composition is for preventing or treating hair loss or hair thinning comprising a compound having a structure of Formula (VII$_A$). In some embodiments, a weight % of the compound in the composition ranges from about 0.005% to about 10.0% by weight relative to the total weight of the composition. In some embodiments, a weight % of the compound in the composition ranges from about 0.01% to about 5%. In some embodiments, a weight % of the compound in the composition ranges from about 0.01% to about 2.0%. In some embodiments, a weight % of the compound in the composition ranges from about 0.0001% to about 10% by weight relative to the total weight of the composition. In some embodiments, a weight % of the compound in the composition is at least about 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition is at most about 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition ranges from about 0.0001 to 10, 0.0005 to 9, 0.001 to 8, 0.005 to 7, 0.01 to 6, 0.02 to 5, 0.03 to 4, 0.04 to 3, 0.05 to 2, 0.06 to 1, 0.07 to 0.9, 0.08 to 0.8, 0.09 to 0.7, 0.1 to 0.6, 0.2 to 0.5, or 0.3 to 0.4% by weight relative to the total weight of the composition.

The composition disclosed herein may further comprise at least one additive selected from, but are not limited to, the group consisting of water, preservatives, antioxidants, chelating agents, sunscreen agents, vitamins, dyes, hair coloring agents, surfactants, detergents, emulsifiers, opacifying agents, volatiles, propellants, liquid vehicles, carriers, salts, pH adjusting agents, neutralizing agents, buffers, hair conditioning agents, anti-static agents, anti-frizz agents, anti-dandruff agents, natural extracts, humectants, fragrances, perfumes, oils, emollients, lubricants, butters, penetrants, thickeners, viscosity modifiers, polymers, resins, hair fixatives, film formers, absorbents, and combinations thereof, in order to achieve a close approximation to commercially available product forms. The composition disclosed herein for treating hair may be formulated in any suitable physical form. For example, in some embodiments, the suitable physical forms include, but not limited to, toner, emulsion, cream, gel, shampoo, conditioner, soap, serum, spray, liquids with low to moderate viscosity, lotions, milks, mousses, oil, and the like. In some embodiments, the composition is formulated to be administered by misting, wiping, rubbing, wetting, dropping, or squirting.

In some embodiments, the composition is a pharmaceutical composition. The pharmaceutical composition may further comprise at least one additive selected from the group consisting of pharmaceutically acceptable carriers, excipients, adjuvants, diluents, and combinations thereof, in order to achieve a close approximation to commercially available product forms.

In some embodiments, the composition is a cosmetic composition. The cosmetic composition may further comprise at least one additive selected from the group consisting of cosmetically acceptable carriers, excipients, adjuvants, diluents, and combinations thereof, in order to achieve a close approximation to commercially available product forms. The composition may be formulated as a liquid solution. The cosmetic composition disclosed herein may be formulated in any suitable physical form. For example, in some embodiments, the suitable physical forms include, but not limited to, toner, emulsion, cream, gel, shampoo, conditioner, soap, serum, spray, liquids with low to moderate viscosity, lotions, milks, mousses, oil, and the like. In some embodiments, the composition may be used as a spray. In some embodiments, the composition may be used as a mist.

In some embodiments, the composition comprises a compound disclosed herein. In some embodiments, the composition may be used for a hair treatment. The treatment may include administration to an area of skin for hair growth on a subject. The area of skin may include all or part of a scalp, brow, eyelid, upper lip, chin, cheek, or other area. In some embodiments, the composition may be used for treatment of hair on a scalp. In some embodiments, the composition may be used for treatment of an eyelash. In some embodiments, the composition may be used for treatment of a beard. In some embodiments, the composition may be used for treatment of an eyebrow.

Non-limiting examples of the composition are shown in Table 11-Table 19. The composition may include any aspect or combination of aspects from any of these tables. A, B, C, D, and E in Table 11-Table 19 represent example ranges of percent weights of each ingredient. For instance, A refers to values less than about 0.05%, B refers to values equal to or larger than about 0.05% and less than about 1%, C represents values equal to or larger than about 1% and less than about 10%, D refers to values equal to or larger than about 10% and less than about 25%, and E represents values equal to or larger than about 25%. Based on these examples, a composition may include any aspect in Table 11-Table 19 in an amount shown therein.

TABLE 11

| Example of composition | |
|---|---|
| Ingredient | % Weight |
| Aqua/Eau/Water | E |
| Ethanol | D |
| Propylene Glycol | D |
| Glycerin | C |
| Propanediol | C |
| Caffeine | B |
| *Serenoa* Serrulata Extract | B |
| *Pyrus Malus* Extract | B |
| Phenoxyethanol | B |
| l-Arginine | B |
| l-Lysine | B |
| Inositol | B |
| *Aloe Barbadensis* Leaf Juice | A |
| Keratin Amino Acid | A |
| Compound disclosed herein | A |
| Ethylhexylglycerin | A |
| Pantothenic Acid | A |
| l-Methionine | A |
| Xanthan Gum | A |
| Niacin | A |
| n-Acetylcysteine | A |

TABLE 11-continued

Example of composition

| Ingredient | % Weight |
|---|---|
| Biotin | A |
| Thiamine HCl (Vitamin B1) | A |

TABLE 12

Example of composition

| Ingredient | % Weight |
|---|---|
| Water/Aqua/Eau | E |
| Propanediol | D |
| Alcohol Denat. | D |
| Glycerin | C |
| Dimethyl Isosorbide | C |
| Ethoxydiglycol | C |
| Polysorbate 20 | C |
| PEG-40 Castor Oil | C |
| Panthenol | B |
| Phenoxyethanol | B |
| *Malus Domestica* Fruit Cell Culture Extract (and) Xanthan Gum (and) Glycerin (and) Lecithin (and) Phenoxyethanol (and) Water (Aqua) | B |
| Isopentyldiol (and) *Trifolium Pratense* (Red Clover) Flower Extract | B |
| Thiamine HCl | B |
| Ethylhexylglycerin | B |
| Allantoin | B |
| Caffeine | B |
| Inositol | B |
| Dipotassium Glycyrrhizate | B |
| Tetrahydrodiferuloylmethane, Tetrahydrodemethoxydiferuloylmethane, Tetrahydrobisdemethoxydiferuloylmethane | B |
| *Serenoa* Serrulata Fruit Extract | B |
| *Panax Ginseng* Root Extract | B |
| Resveratrol | B |
| *Aloe Barbadensis* Leaf Juice | B |
| Sodium Phytate | B |
| Niacinamide | B |
| Raspberry Ketone | B |
| *Ganoderma Lucidum* Extract | B |
| Compound disclosed herein | A |
| *Larix Gmelinii* (Larch) Wood Extract | A |
| *Pyrus Malus* (Apple) Fruit Extract | A |
| *Camellia Sinensis* Leaf Extract | A |
| *Piper Nigrum* Fruit Extract | A |
| *Pinus Pinaster* Bark Extract | A |
| *Citrus Paradisi* (Grapefruit) Peel Extract | A |
| *Olea Europaea* (Olive) Leaf Extract | A |

TABLE 13

Example of composition

| Ingredient | % Weight |
|---|---|
| Water/Aqua/Eau | E |
| Propanediol | D |
| Alcohol Denat. | D |
| Dimethyl Isosorbide | D |
| Glycerin | C |
| Ethoxydiglycol | C |
| PEG-40 Castor Oil | C |
| Panthenol | B |
| Phenoxyethanol | B |
| Polysorbate 20 | B |
| *Malus Domestica* Fruit Cell Culture Extract (and) Xanthan Gum (and) Glycerin (and) Lecithin (and) Phenoxyethanol (and) Water (Aqua) | B |

TABLE 13-continued

Example of composition

| Ingredient | % Weight |
|---|---|
| Isopentyldiol (and) *Trifolium Pratense* (Red Clover) Flower Extract | B |
| Ethylhexylglycerin | B |
| Allantoin | B |
| Inositol | B |
| Dipotassium Glycyrrhizate | B |
| Disodium EDTA | B |
| *Serenoa* Serrulata Fruit Extract | B |
| Resveratrol | B |
| Tetrahydrodiferuloylmethane, Tetrahydrodemethoxydiferuloylmethane, Tetrahydrobisdemethoxydiferuloylmethane | B |
| *Aloe Barbadensis* Leaf Juice | B |
| *Panax Ginseng* Root Extract | A |
| Citric Acid | A |
| Compound disclosed herein | A |
| *Ganoderma Lucidum* Extract | A |
| *Piper Nigrum* Fruit Extract | A |
| *Pinus Pinaster* Bark Extract | A |
| *Olea Europaea* (Olive) Leaf Extract | A |

TABLE 14

Example of composition

| Ingredient | % Weight |
|---|---|
| Water/Aqua/Eau | E |
| Alcohol Denat. | D |
| Dimethyl Isosorbide | D |
| Glycerin | C |
| Propanediol | C |
| Polysorbate 20 | C |
| Ethoxydiglycol | C |
| PEG-40 Hydrogenated Castor Oil | C |
| d-Panthenol | B |
| Phenoxyethanol | B |
| Hydroxyethylcellulose | B |
| *Malus Domestica* Fruit Cell Culture Extract (and) Xanthan Gum (and) Glycerin (and) Lecithin (and) Phenoxyethanol (and) Water (Aqua) | B |
| Ethylhexylglycerin | B |
| Allantoin | B |
| Dipotassium Glycyrrhizate | B |
| *Pyrus Malus* Skin Extract | B |
| *Aloe Barbadensis* Leaf (Aloe Vera) Extract | B |
| Caffeine | B |
| Inositol | B |
| Resveratrol | B |
| Disodium EDTA | B |
| Compound disclosed herein | A |
| Citric Acid | A |
| *Citrus Paradisi* (Grapefruit) Peel Extract | A |
| *Olea Europaea* (Olive) Leaf Extract | A |

TABLE 15

Example of composition

| Ingredient | % Weight |
|---|---|
| Water/Aqua/Eau | E |
| Propanediol | D |
| Butylene Glycol | D |
| Dimethyl Isosorbide | C |
| Polysorbate 20 | C |
| Ethoxydiglycol | C |
| Glycerin | C |
| PEG-40 Castor Oil | C |
| *Pisum Sativum* (Pea) Sprout Extract (and) | C |

TABLE 15-continued

Example of composition

| Ingredient | % Weight |
| --- | --- |
| Phenoxyethanol (and) Sodium Benzoate (and) Water (Aqua) | |
| *Malus Domestica* Fruit Cell Culture Extract (and) Xanthan Gum (and) Glycerin (and) Lecithin (and) Phenoxyethanol (and) Water (Aqua) | C |
| PEG-8 Dimethicone | C |
| Phenoxyethanol | B |
| Hydroxyethylcellulose | B |
| Panthenol | B |
| Glycerin (and) Water (and) *Calendula Officinalis* Extract | B |
| Disodium EDTA | B |
| Dipotassium Glycyrrhizate | B |
| Ethylhexylglycerin | B |
| Citric Acid | B |
| Tetrahydrodiferuloylmethane, Tetrahydrodemethoxydiferuloylmethane, Tetrahydrobisdemethoxydiferuloylmethane | B |
| *Panax Ginseng* Root Extract | A |
| Compound disclosed herein | A |

TABLE 16

Example of composition

| Ingredient | % Weight |
| --- | --- |
| Water/Aqua/Eau | E |
| Alcohol Denat. | D |
| Butylene Glycol | C |
| Propanediol | C |
| Fructose (and) Glycerin (and) Water (and) *Sechium Edule* Fruit Extract | C |
| Glycerin (and) Water (and) *Hippophae Rhamnoides* Fruit Extract | C |
| *Pisum Sativum* (Pea) Sprout Extract (and) Phenoxyethanol (and) Sodium Benzoate (and) Water (Aqua) | C |
| Water (and) *Furcellaria Lumbricalis* Extract | C |
| Phenoxyethanol | B |
| Panthenol | B |
| Glycerin (and) Water (and) *Calendula Officinalis* Extract | B |
| Isopentyldiol (and) *Trifolium Pratense* (Red Clover) Flower Extract | B |
| Dipotassium Glycyrrhizate | B |
| Resveratrol | B |
| Ethylhexylglycerin | B |
| *Aloe Barbadensis* Leaf Juice | B |
| Citric Acid | B |
| *Panax Ginseng* Root Extract | A |
| Compound disclosed herein | A |

TABLE 17

Example of composition

| Ingredient | % Weight |
| --- | --- |
| Caprylic/Capric Triglycerides | E |
| Coco-Caprylate | D |
| Isodecyl Neopentanoate | D |
| Hydrogenated Vegetable Oil | C |
| *Punica Granatum* (Pomegranate) Seed Oil | C |
| Dimethyl Isosorbide | C |
| Squalane | C |
| Avocado Oil | C |
| *Argania Spinosa* (Argan) Kernel Oil | C |
| Apricot Kernel Oil | C |
| *Vitis Vinifera* (Grapeseed) Seed Oil | C |

TABLE 17-continued

Example of composition

| Ingredient | % Weight |
| --- | --- |
| Ethoxydiglycol | C |
| PEG-40 Hydrogenated Castor Oil | B |
| Sorbitan Laurate | B |
| Tocopherol | B |
| Compound disclosed herein | B |

TABLE 18

Example of composition

| Ingredient | % Weight |
| --- | --- |
| *Argania Spinosa* (Argan) Kernel Oil | E |
| Dimethyl Isosorbide | D |
| Octyldodecanol | C |
| *Ricinus Communis* (Castor) Seed Oil | C |
| Ethoxydiglycol | C |
| PEG-40 Hydrogenated Castor Oil | B |
| Polysorbate 20 | B |
| Tocopheryl Acetate | B |
| Compound disclosed herein | B |
| *Citrus Paradisi* (Grapefruit) Peel Extract | A |
| *Olea Europaea* (Olive) Leaf Extract | A |

TABLE 19

Example of composition

| Ingredient | % Weight |
| --- | --- |
| Caprylic/Capric Triglycerides | E |
| Coco-Caprylate | D |
| Dimethyl Isosorbide | D |
| *Punica Granatum* (Pomegranate) Seed Oil | C |
| *Cucurbita Pepo* (Pumpkin) Seed Oil | C |
| *Argania Spinosa* (Argan) Kernel Oil | C |
| *Borago Officinalis* (Borage) Seed Oil | C |
| Ethoxydiglycol | C |
| Octyldodecanol | C |
| PEG-40 Hydrogenated Castor Oil | B |
| Sorbitan Laurate | B |
| *Ricinus Communis* (Castor) Seed Oil | B |
| *Vitis Vinifera* (Grapeseed) Seed Oil | B |
| Tocopherol | B |
| *Brassica Oleracea Italica* (Broccoli) Seed Oil | B |
| Compound disclosed herein | B |
| *Pinus Pinaster* Bark Extract | A |
| *Olea Europaea* (Olive) Leaf Extract | A |

Disclosed herein, in some embodiments, are formulations that include an aspect or combination of aspects in any of Tables 11-19. The aspect or combination of aspects in any of Tables 11-19 may each comprise 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1%, or a range defined by any two of the aforementinoed percentages, of the composition. The percentage may be weight/weight or weight/volume. The aspect or combination of aspects in any of Tables 11-19 may each comprise about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1%, or a range defined by any two of the aforementinoed percentages, of the composition. The aspect or combination of aspects in any of Tables 11-19 may each comprise at least 0.001%, at least 0.002%, at least 0.003%, at least 0.004%, at least 0.005%, at least 0.006%, at least 0.007%, at least 0.008%, at least 0.009%, at least 0.01%, at least 0.02%, at least 0.03%, at least 0.04%, at least 0.05%, at least 0.06%, at least 0.07%, at least 0.08%, at least 0.09%, or at least 0.1% of the composition. The aspect or combination of aspects in any of Tables 11-19 may each comprise no greater than 0.001%, no greater than 0.002%, no greater than 0.003%, no greater than 0.004%, no greater than 0.005%, no greater than 0.006%, no greater than 0.007%, no greater than 0.008%, no greater than 0.009%, no greater than 0.01%, no greater than 0.02%, no greater than 0.03%, no greater than 0.04%, no greater than 0.05%, no greater than 0.06%, no greater than 0.07%, no greater than 0.08%, no greater than 0.09%, or no greater than 0.1% of the composition. The aspect or combination of aspects in any of Tables 11-19 may each comprise 0.1%, 0.2%, 0.3%, 0.4%, 0.5%, 0.6%, 0.7%, 0.8%, 0.9%, 1%, 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or a range defined by any two of the aforementinoed percentages, of the composition. The percentage may be weight/weight or weight/volume. The aspect or combination of aspects in any of Tables 11-19 may each comprise about 0.1%, about 0.2%, about 0.3%, about 0.4%, about 0.5%, about 0.6%, about 0.7%, about 0.8%, about 0.9%, about 1%, about 2.5%, about 5%, about 7.5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or a range defined by any two of the aforementinoed percentages, of the composition. The aspect or combination of aspects in any of Tables 11-19 may each comprise at least 0.1%, at least 0.2%, at least 0.3%, at least 0.4%, at least 0.5%, at least 0.6%, at least 0.7%, at least 0.8%, at least 0.9%, at least 1%, at least 2.5%, at least 5%, at least 7.5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, of the composition. The aspect or combination of aspects in any of Tables 11-19 may each comprise no greater than 0.1%, no greater than 0.2%, no greater than 0.3%, no greater than 0.4%, no greater than 0.5%, no greater than 0.6%, no greater than 0.7%, no greater than 0.8%, no greater than 0.9%, no greater than 1%, no greater than 2.5%, no greater than 5%, no greater than 7.5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, or no greater than 95%, of the composition.

Methods

Also provided herein include methods for hair treatment with the compound(s) or salt(s) disclosed herein.

In certain aspects, disclosed herein is a method for preventing or treating hair loss or hair thinning, the method comprising administering to a subject in need thereof a composition comprising a compound or salt described herein, or a composition described herein. The compound(s) or salt(s) thereof may have a structural Formula of (I), (II), (III), (IV), (V), (VI), (VII$_A$), (VII$_B$), or (VIII). The compound(s) or salt(s) thereof may be selected from those set forth in any one of Tables 1-10, or any subset thereof, or any combination thereof.

In some embodiments, the method comprises administering to a subject in need thereof a composition comprising a compound having a structure of Formula (VII$_B$) or a salt described herein, a composition, or a formulation described herein. The compound(s) or salt(s) thereof may have a structural Formula of (VII$_B$):

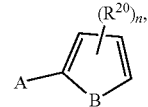

Formula (VII$_B$)

or a pharmaceutically or cosmetically acceptable salt thereof, wherein:
A is selected from a triazole, wherein the triazole is optionally substituted with one or more $R^{10}$;
B is selected from O, NH, S;
n is selected from 0, 1, 2, and 3;
each $R^{10}$ is independently selected at each occurrence from halogen, $C_{1-6}$ alkyl, $C_{2-6}$ alkenyl, and $C_{2-6}$ alkynyl, $-OR^{11}$, $-SR^{11}$, $-NO_2$, $=O$, $=NH$, $-CN$, $-C(O)R^{11}$, $-C(O)OR^{11}$, $-OC(O)R^{11}$, $-OC(O)N(R^{11})_2$, $-NR^{11}S(O)_2R^{11}$, $-C(O)N(R^{11})_2$, $-N(R^{11})C(O)R^{11}$, $-N(R^{11})C(O)N(R^{11})_2$, $-N(R^{11})C(O)OR^{11}$, $-S(O)_2(R^{11})$, $-S(O)_2N(R^{11})_2$, $C_{1-10}$ alkyl, $C_3$-$C_{12}$ carbocycle and 5- to 12-membered heterocycle;
each $R^{11}$ is independently selected at each occurrence from hydrogen; $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents selected from $=O$, and phenyl, wherein the phenyl is optionally substituted with one or more substituents independently selected from $-C(O)R^{12}$, and $-S(O)_2(R^{12})$;
each $R^{12}$ is independently selected at each occurrence from hydrogen, halogen, $-NHC_{1-10}$ alkyl, $-N(C_{1-10}$ alkyl$)_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle;
each $R^{20}$ is independently selected from halogen, $-OH$, $-CN$, $-NO_2$, $-NH_2$, $-NHC_{1-10}$ alkyl, $-N(C_{1-10}$ alkyl$)_2$, $C_{1-10}$ alkyl, $-C_{1-10}$ haloalkyl, $-O-C_{1-10}$ alkyl, $C_{2-10}$ alkenyl, $C_{2-10}$ alkynyl, $C_{3-12}$ carbocycle, and 3- to 12-membered heterocycle,
wherein a weight % of the compound in the composition has at least about 0.0001% to at most about 10% by weight relative to the total weight of the composition.

In some embodiments, the compound of Formula (VII$_B$) is represented by

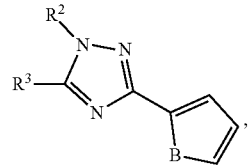

Formula (VII$_B$-A)

or a pharmaceutically or cosmetically acceptable salt thereof, wherein;
B is selected from oxygen and sulfur;
$R^2$ is —S(O)$_2$(R$^{11}$);
$R^3$ is —SR$^{11}$;
wherein each R$^{11}$ is selected from C$_{1-6}$ alkyl.

In some embodiments, B is oxygen. In some embodiments, R$^{11}$ is C$_1$alkyl.

In some embodiments, the compound of Formula (VII$_B$) is represented by

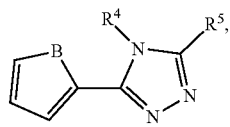

Formula (VII$_B$-B)

or a pharmaceutically or cosmetically acceptable salt thereof, wherein;
B is selected from oxygen and sulfur;
$R^4$ is C$_{1-6}$ alkyl;
$R^5$ is —SR$^{11}$; and
wherein R$^{11}$ is selected from C$_{1-6}$ alkyl, wherein C$_{1-6}$ alkyl is optionally substituted with one or more substituents selected from =O, and phenyl, wherein the phenyl is optionally substituted with one or more substituents independently selected from —S(O)$_2$(R$^{12}$), and wherein R$^{12}$ is a 5-membered heterocycle.

In some embodiments, B is oxygen. In some embodiments, R$^4$ is C$_2$alkyl. In some embodiments, R$^{12}$ is

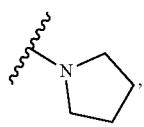

In some embodiments, the compound of Formula (VII$_B$) is represented by

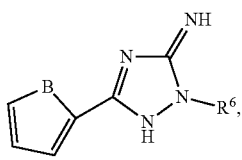

Formula (VII$_B$-C)

or a pharmaceutically or cosmetically acceptable salt thereof, wherein;
B is selected from oxygen and sulfur;
$R^6$ is —S(O)$_2$(R$^{11}$); and
wherein R$^{11}$ is selected from C$_{1-6}$ alkyl.

In some embodiments, B is oxygen. In some embodiments, R$^{11}$ is C$_2$alkyl.

In some embodiments, the triazole is selected from

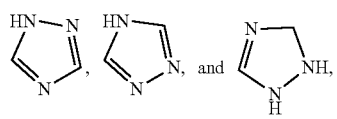

each of which is optionally substituted with one or more R$^{10}$.

In some embodiments, B is oxygen.
In some embodiments, R$^{10}$ is selected from C$_{1-6}$ alkyl, —SR$^{11}$, =NH, and —S(O)$_2$(R$^{11}$). In some embodiments, R$^{11}$ is selected from C$_{1-2}$ alkyl, and

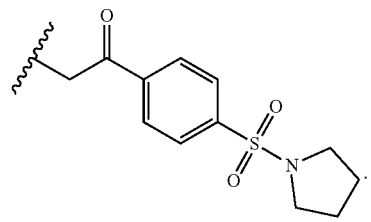 [SMILES: *CC(=O)c1ccc(S(=O)(=O)N2CCCC2)cc1]

In some embodiments, R$^{10}$ is C$_{1-6}$ alkyl. In some embodiments, R$^{10}$ is C$_2$alkyl.
In some embodiments, R$^{10}$ is —SR$^{11}$. In some embodiments, R$^{11}$ is C$_1$alkyl. In some embodiments, R$^{11}$ is

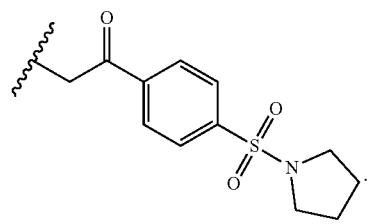 [SMILES: *CC(=O)c1ccc(S(=O)(=O)N2CCCC2)cc1]

In some embodiments, R$^{10}$ is =NH.
In some embodiments, R$^{10}$ is —S(O)$_2$(R$^{11}$). In some embodiments, R$^{11}$ is C$_2$alkyl.
In some embodiments, n is 0. In some embodiments, R$^4$ is C$_2$ alkyl.
In some embodiments, a compound having structural Formula (VII$_B$) is selected from:

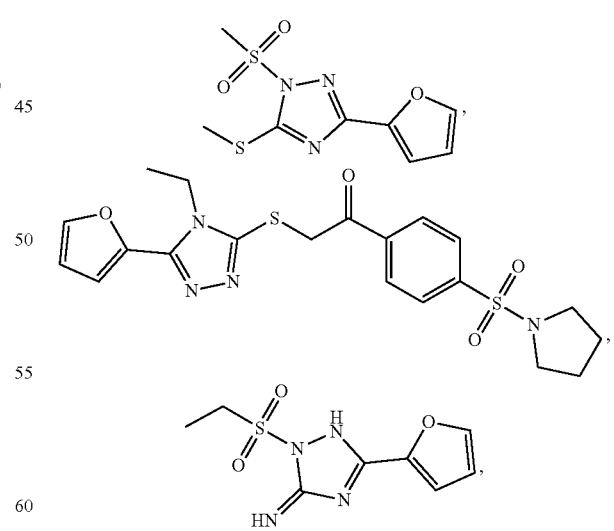

or a pharmaceutically or cosmetically acceptable salt thereof.

In some embodiments, the method comprises administering to a subject in need thereof a composition comprising a compound having a structure of Formula (VII$_A$) or a salt described herein, a composition, or a formulation described herein. The compound(s) or salt(s) thereof may have a structural Formula of (VII$_A$):

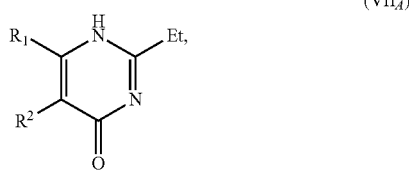

or a pharmaceutically or cosmetically acceptable salt thereof, wherein:
E is selected from hydrogen, $C_5$-$C_8$ aryl, and heteroaryl;
$R^1$ is selected from hydrogen, $C_{1-6}$ alkyl, $C_{1-6}$ haloalkyl, —S—$C_{1-6}$ alkyl, —S—$C_{1-6}$ haloalkyl, —S(O)(O)$R^a$;
wherein $R^a$ is selected from hydrogen, $C_{1-6}$ alkyl, and $C_{1-6}$ haloalkyl; and $R^2$ is selected from —C(O)OH, —C(O)O—$R^c$, and —C(O)O—$C_{1-6}$ haloalkyl,
wherein a weight % of the compound in the composition is at least about 0.0001% to at most about 10% by weight relative to the total weight of the composition.

In some embodiments, E is $C_5$-$C_8$ aryl. In some embodiments, E is phenyl.

In some embodiments, $R^1$ is S(O)(O)$R^a$. In some embodiments, $R^a$ is $C_1$alkyl. In some embodiments, $R^1$ is —S(O)(O)$CH_3$.

In some embodiments, $R^2$ is —C(O)O—$R^c$. In some embodiments, $R^2$ is —C(O)OCH$_3$. In some embodiments, a compound having structural Formula (VII$_A$) is

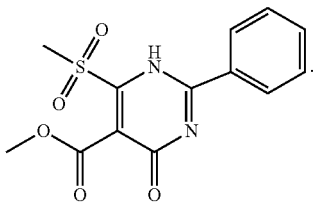 [SMILES: COC(=O)c1c(S(C)(=O)=O)[nH]c(-c2ccccc2)nc1=O]

In some embodiments, a weight % of the compound in the composition ranges from about 0.0001% to about 10% by weight relative to the total weight of the composition. In some embodiments, a weight % of the compound in the composition is at least about 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition is at most about 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition ranges from about 0.0001 to 10, 0.0005 to 9, 0.001 to 8, 0.005 to 7, 0.01 to 6, 0.02 to 5, 0.03 to 4, 0.04 to 3, 0.05 to 2, 0.06 to 1, 0.07 to 0.9, 0.08 to 0.8, 0.09 to 0.7, 0.1 to 0.6, 0.2 to 0.5, or 0.3 to 0.4% by weight relative to the total weight of the composition.

A diagnosis of hair loss or hair thinning may or may not have been made. In some embodiments of any method described herein, the subject may have been diagnosed with hair loss or hair thinning. In some embodiments of any method described herein, the subject may not have been diagnosed with hair loss or hair thinning. In some embodiments, the method promotes hair growth, hair restoration or hair thickening of said subject. In some embodiments, the method increases hair density or hair growth rate of said subject. In some embodiments, the hair loss is selected from androgenic alopecia, alopecia areata, androgenetic alopecia, gynecologic alopecia, postpartum alopecia, seborrheic alopecia, non-rigid alopecia, senile alopecia, chemotherapy-induced alopecia, radiation-induced alopecia, male-pattern baldness, female-pattern baldness, cicatricial alopecia, alopecia areata telogen effluvium, traction alopecia, and anagen effluvium. In some embodiments, the hair is scalp hair, eyelash hair, eyebrow hair, or facial hair.

In some embodiments, the composition is a pharmaceutical composition. In some embodiments, the pharmaceutical composition further comprises at least one additive selected from the group consisting of pharmaceutically acceptable carriers, excipients, adjuvants, and diluents.

In some embodiments, the pharmaceutical composition is administered one to three times a day. In some embodiments, the pharmaceutical composition is administered once a day. In some embodiments, the pharmaceutical composition is administered two times a day. In some embodiments, the pharmaceutical composition is administered three times a day. In some embodiments, the pharmaceutical composition is administered every other day. In some embodiments, the pharmaceutical composition is administered for at least two consecutive days. In some embodiments, the pharmaceutical composition is administered for at least three consecutive days. In some embodiments, the pharmaceutical composition is administered for at least four consecutive days. In some embodiments, the pharmaceutical composition is administered for at least five consecutive days. In some embodiments, the pharmaceutical composition is administered for at least seven consecutive days.

In some embodiments, the pharmaceutical composition is administered at least for about 2 days, 3 days, 5 days, 7 days, 10 days, 15 days, 20 days, 30 days, 50 days, 60 days, 80 days, 90 days, 5 months, 6 months, 7 months, 8 months, 9 months, 10 months, 11 months, a year, 2 years, or 3 years. In some embodiments, the pharmaceutical composition is administered at most for about 2 days, 3 days, 5 days, 7 days, 10 days, 15 days, 20 days, 30 days, 50 days, 60 days, 80 days, 90 days, 5 months, 6 months, 7 months, 8 months, 9 months, 10 months, 11 months, a year, 2 years, or 3 years. In some embodiments, the pharmaceutical composition is administered from about 2 days to 3 years, 3 days to 2 years, 5 days to a year, 7 days to 11 months, 10 days to 10 months, 15 days to 9 months, 20 days to 8 months, 30 days to 7 months, 50 days to 6 months, 60 days to 5 months, 80 days to 4 months, or 90 days to 3 years.

In some embodiments, the composition is a cosmetic composition. In some embodiments, the cosmetic composition further comprises at least one additive selected from the group consisting of cosmetically acceptable carriers, excipients, adjuvants, and diluents. In some embodiments, the cosmetic composition is formulated as toner, emulsion, cream, gel, shampoo, soap, serum, spray, or oil.

In some embodiments, the hair loss is selected from androgenic alopecia, alopecia areata, androgenetic alopecia, gynecologic alopecia, postpartum alopecia, seborrheic alopecia, non-rigid alopecia, senile alopecia, chemotherapy-induced alopecia, radiation-induced alopecia, male-pattern baldness, female-pattern baldness, cicatricial alopecia, alopecia areata telogen effluvium, traction alopecia, anagen effluvium, and combinations thereof. In some embodiments, the method promotes hair strength, hair growth, hair restoration, hair thickening, or combinations thereof of the subject. In some embodiments, the method increases hair density, hair growth rate, or combination thereof of the subject. In some embodiments, the hair is scalp hair, eyelash hair, eyebrow hair, or facial hair.

Disclosed herein, in some embodiments, are methods of treating hair loss or hair thinning. The administration may decrease a measurement such as a hair loss or hair thinning measurement relative to a baseline measurement. The measurement may include a hair shedding measurement. The administration may decrease a level of hair shedding relative to a level of baseline hair shedding. The measurement may include a hair loss measurement. The administration may decrease hair loss relative to a baseline hair loss. The measurement may include a number, amount, percentage, or degree. The measurement may include a rate, such as a number or amount over time. In some embodiments, the decrease in the measurement is by at least 1%, at least 2.5%, at least 5%, at least 7.5%, or at least 10%, relative to the baseline measurement.

Disclosed herein, in some embodiments, are methods of treating hair loss or hair thinning. The administration may increase a measurement relative to a baseline measurement. The measurement may include a hair growth measurement. The administration may increase a level of hair growth relative to a level of baseline hair growth, thickness. The measurement may include a hair proliferation measurement. The administration may increase hair proliferation relative to a baseline hair proliferation. The measurement may include a hair thickness measurement. The administration may increase hair thickness relative to a baseline hair thickness. The measurement may include a hair fullness measurement. The administration may increase hair fullness relative to a baseline hair fullness. The measurement may include a hair strength measurement. The administration may increase hair strength relative to a baseline hair strength. The measurement may include a number, amount, percentage, or degree. The measurement may include a hair follicle measurement. The measurement may include a number of hairs. The measurement may include a number of cells. The measurement may include a measure of gene activation, such as activation of a gene involved in hair growth or hair cell. The measurement may be in an area of skin. For example, the measurement may include a number of hairs per an area of skin (e.g. per square inch or per square centimeter). The measurement may include a rate, such as a number or amount over time. In some embodiments, the increase in the measurement is by at least 1%, at least 2.5%, at least 5%, at least 7.5%, or at least 10%, relative to the baseline measurement.

Kits

This disclosure also provides a kit comprising the composition disclosed herein. In some embodiments, the kit further comprises an applicator. In some embodiments, the kit further comprises written instructions for using the composition in a hair treatment.

EXAMPLES

The invention now being generally described, it will be more readily understood by reference to the following examples which are included merely for purposes of illustration of certain aspects and embodiments of the present invention, and are not intended to limit the invention in any way.

Example 1: Assay of Human Follicle Dermal Papilla Cells (hFDPC) Proliferation

The ability of a compound or salt of the present disclosure to increase proliferation of human hair follicle dermal papilla cells (hFDPC) was tested using a cell viability assay, such as the Promega CellTiter-Glo® Luminescent Cell Viability Assay, MTT cell proliferation assay (ATCC® 30-1010K) or cell counting. Table 20 shows the results. In Table 8, A represents less than 20% of increased proliferation of hFDPCs, B represents 20-40%, and C represents larger than 40% of increased proliferation of hFDPCs. For this assay, hFDPCs were cultured on tissue culture-treated plastic and supplemented with 6-bromoindirubin-39-Oxime (BIO), recombinant bone morphogenetic protein-2 (BMP-2), and basic fibroblast growth factor (FGFβ), whose combination was previously found to preserve in situ dermal papilla gene signatures. A result using compound VII-3 is shown in FIG. 1.

TABLE 20

Evaluation of small molecules based on hFDPC proliferation

| ID # | Percent Increase Proliferation of hFDPCs (%) |
|---|---|
| I-1 | A |
| I-2 | B |
| I-3 | A |
| I-4 | A |
| I-5 | B |
| I-6 | A |
| I-7 | A |
| I-8 | B |
| I-9 | B |
| I-10 | A |
| I-11 | A |
| I-12 | B |
| I-13 | A |
| I-14 | A |
| I-15 | B |
| I-16 | A |
| I-17 | C |
| I-18 | B |
| II-1 | A |
| II-2 | B |
| II-3 | B |
| II-4 | B |
| II-5 | B |
| II-6 | B |
| III-1 | A |
| III-2 | A |
| III-3 | B |
| III-4 | B |
| III-5 | A |
| IV-1 | B |
| IV-2 | A |
| IV-3 | B |
| IV-4 | A |
| V-1 | A |
| V-2 | A |
| V-3 | B |
| V-4 | A |
| VI-1 | A |
| VI-2 | B |
| VI-3 | B |
| VI-4 | A |
| VI-5 | A |
| VI-6 | A |
| VII-1 | C |
| VII-2 | A |
| VII-3 | B |
| VII-4 | A |
| VII-5 | A |
| VII-6 | A |
| VII-7 | B |

TABLE 20-continued

Evaluation of small molecules based on hFDPC proliferation

| ID # | Percent Increase Proliferation of hFDPCs (%) |
|---|---|
| VII-8 | A |
| VII-9 | B |
| VII-10 | B |
| VII-11 | A |
| VII-12 | A |
| VII-13 | A |
| VII-14 | A |
| VII-15 | A |
| VII-16 | A |
| VII-17 | A |
| VII-18 | A |
| VII-19 | A |
| VII-20 | A |
| VII-21 | A |
| VII-22 | A |
| VII-23 | B |
| VII-24 | A |
| VII-25 | B |
| VII-26 | A |

A represents less than 20% of increased proliferation of hFDPCs, B represents 20-40%, and C represents larger than 40% of increased proliferation of hFDPCs.

Example 2: Assay on Keratinocytes

Human adult epidermal keratinocytes were cultured on poly-L-lysine treated plates and the ability of a compound or salt of the present disclosure to impact proliferation was measured using a cell viability assay, such as Promega CellTiter-Glo® Luminescent Cell Viability Assay, MTT cell proliferation assay (ATCC® 30-1010K) or cell counting after 48 hr. The compound or salt was added at different concentrations spanning at least a 2-log range.

Example 3: Assay on Fibroblasts

The ability of a compound or salt of the present disclosure to impact proliferation of human adult dermal fibroblasts was tested using a cell viability assay, such as Promega CellTiter-Glo® Luminescent Cell Viability Assay, MTT cell proliferation assay (ATCC® 30-1010K) or cell counting after 48 hr. The compound or salt was added at different concentrations spanning at least a 2-log range.

Example 4: Assay on Endothelial Cells

The ability of a compound or salt of the present disclosure to impact proliferation of human adult dermal microvascular endothelial cells was tested using a cell viability assay, such as Promega CellTiter-Glo® Luminescent Cell Viability Assay, MTT cell proliferation assay (ATCC® 30-1010K) or cell counting after 48 hr. The compound or salt was added at different concentrations spanning at least a 2-log range.

Example 5: In Silico Safety/Toxicology Studies

The in silico safety/toxicology profiles of compounds were determined by screening chemical structures against a series of computational models. These include the Pred-hERG 4.2 cardiotoxicity model and the NeuroDeRisk IL Profiler neurotoxicity model, as well as reproductive and developmental toxicity, carcinogenicity (genotoxic and non-genotoxic), skin sensitization, DNA mutation, and chromosomal aberration models from QSAR Toolbox.

Example 6: Safety/Toxicology Studies

The safety/toxicology profiles of a compound or salt of the present disclosure was evaluated via a series of in vitro genotoxicity assays, including the SOS-chromotest to determine bacterial genotoxicity, and the TK.6 micronucleus assay to determine chromosomal damage and forward mutations. Standard reactive oxygen species (ROS) and caspase 3/7 assay were conducted to determine general cellular toxicity. Moreover, a series of sensitization tests were conducted to predict any potential skin sensitivity. These include the direct peptide reactivity assay to evaluate haptenization, the KeratinoSens reporter assay to determine potential sensitivity via the activation of a cytoprotective pathway, and an immunological assay using human immature monocyte-derived dendritic cells to evaluate any potential immunogenicity.

Future studies will include mechanism-oriented studies, including metabolism and transport studies focusing on the ability of a compound or salt of the present disclosure to induce or inhibit cytochrome P450, passive/active transport using the caco-2 cell line and compound efflux using the MDR-MDCK cell line, all well-established assays. Additional safety and toxicity studies include functional cardiotoxicity and neurotoxicity in human iPSC-derived cardiomyocytes and neurons, respectively. Finally, a repeated insult patch test will be performed using a compound or salt of the present disclosure on 200 human subjects to predict induced allergic contact dermatitis and associated responses.

Example 7: Efficacy Studies

The functional profile of a compound or salt of the present disclosure continues to be investigated in a number of 3D cellular and ex vivo models, and ultimately clinical trials. Additionally, transcriptomic and proteomic analyses will be conducted on relevant genes and proteins with well-established functional roles such as VEGF or beta-catenin on cells exposed to a compound or salt of the present disclosure. The "two-cell assemblage" (TCA) 3D co-culture model, which involves coating human outer root sheath cells (hORS) on top of a dense spheroid of human follicle papilla cells, will continue to be used. The hFDPCs support the polar outgrowth of the hORS, resembling a hair-like bulb-in-a-dish. Additionally, a compound or salt of the present disclosure will be treated on excised live human skin (containing hair) grafts from cosmetic surgeries and evaluate the targeted activation of follicle papilla cells in histology studies. Finally, a clinical efficacy trial will be performed with 30 human subjects with hair loss or hair thinning to determine effectiveness of a compound or salt of the present disclosure to promote hair growth. Additional trials with more subjects and spanning wider age groups and demographics may follow.

Example 8: Mechanistic Analysis

Using the transcriptomics data, a series of mechanistic computational analyses will be performed to identify possible mechanisms of action. These may include DE analyses followed by GO term and pathway enrichment to characterize the biological imprint of the example chemicals. In addition, pseudo-time and cell-cycle analyses will be performed to probe the developmental effects of these chemicals on target cells. The extracted insight in further investigations and models will be validated.

Figure 2A:
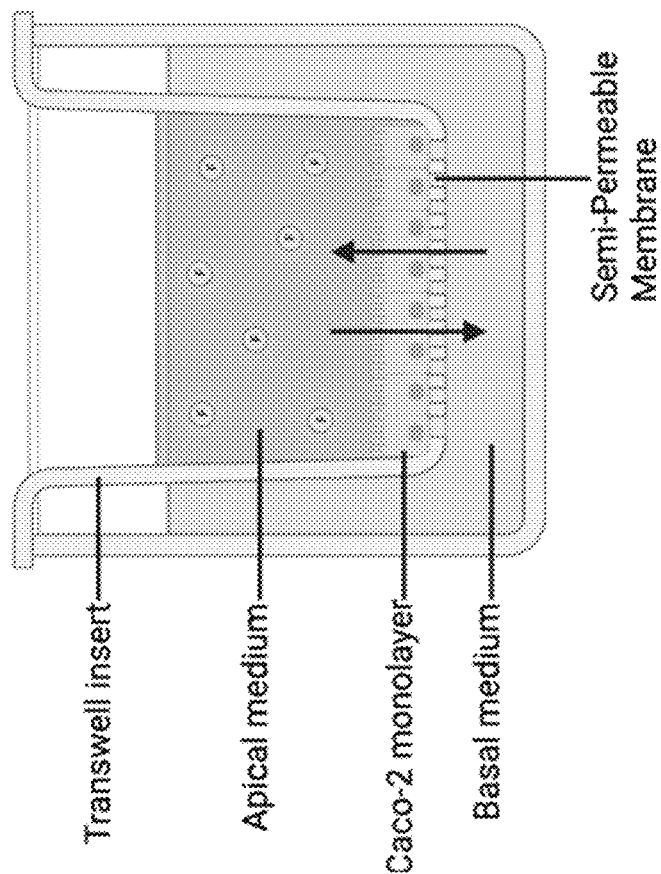
FIG. 2A shows schematic representation of a model system, in accordance with one or more embodiments of the present disclosure. Caco-2 cells were cultured on transwells and cultured until a monolayer formed, mimicking the intestinal cell barrier. The cultures were treated with compound VII-3 or vehicle control (0.1% v/v DMSO) on the apical side for 24 hr and cultured in media containing a fluorescent dye (Lucifer yellow, labeled "F").
Figure 2B:
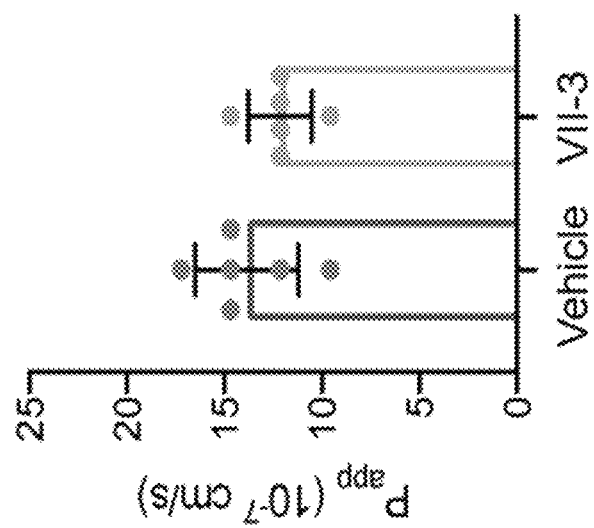
FIG. 2B shows apparent permeability of a Caco-2 monolayer dosed with DMSO and compound VII-3, in accordance with one or more embodiments of the present disclosure. No difference in apparent permeability was observed. Data represents mean±s.d. and representative of at least 2 experimental replicates.

Example 9: An Example Compound does not Disrupt Intestinal Cell Barrier Integrity in a Caco-2 Monolayer System This example shows the measurement of the rate of flux of a compound across polarized Caco-2 cell monolayers and the data generated can be used to predict in vivo absorption of compounds. FIG. 2A is a schematic representation of a model system. Caco-2 cells were cultured on transwells and cultured until a monolayer formed, mimicking the intestinal cell barrier. The cultures were treated with an example compound (VII-3) or vehicle control (0.1% v/v DMSO) on the apical side for 24 hr and cultured in media containing a fluorescent dye (Lucifer yellow, labeled "F"). FIG. 2B shows apparent permeability of a Caco-2 monolayer dosed with DMSO and a representative compound. There was no observed difference in apparent permeability. Data represents mean±s.d. and representative of at least 2 experimental replicates.

Example 10: Example Compounds Exhibit No Genotoxic Transformation Potential

TK.6 lymphoblasts are a well-studied cell line commonly used for gene mutation analyses. They are heterozygous for the thymidine kinase gene (TK) and enable the detection of forward mutations and chromosomal damage, which manifests as micronuclei and are detectable via flow cytometry.

Figure 3A:
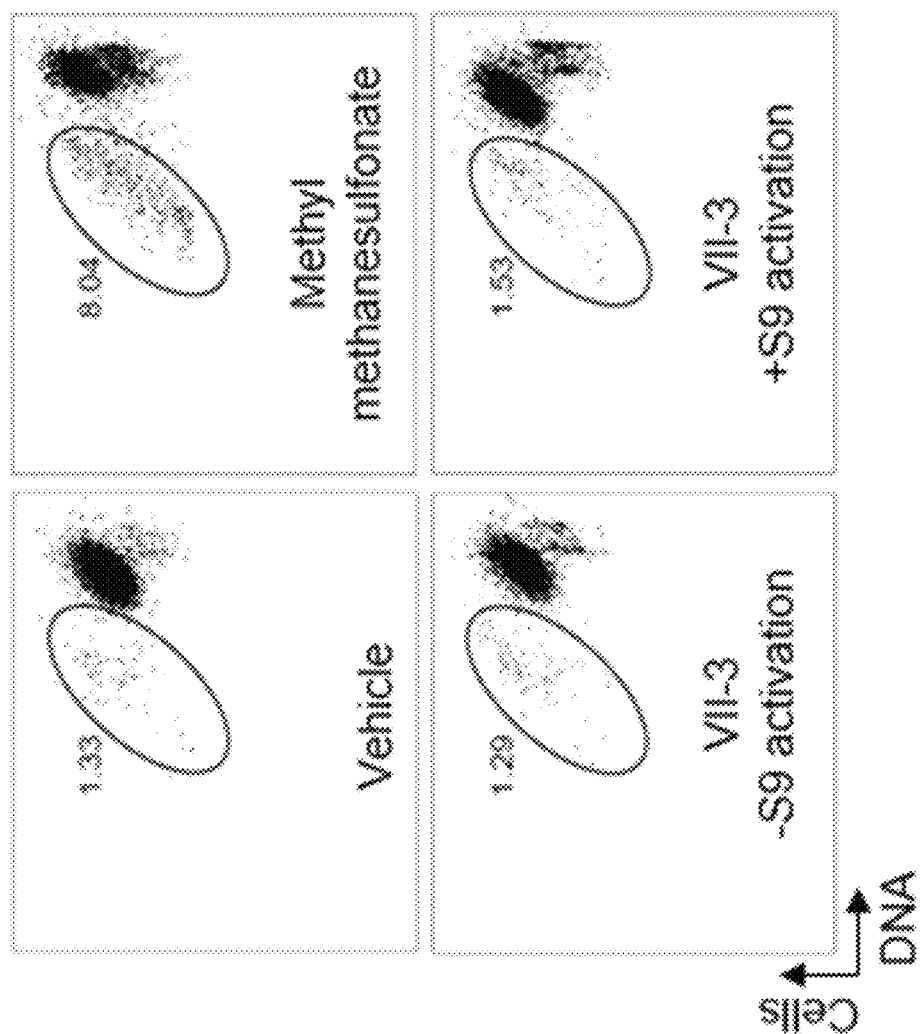
FIG. 3A shows representative plots of TK.6 cells treated with compound VII-3, with or without S9 metabolic activation, in accordance with one or more embodiments of the present disclosure. Methyl methanesulfonate, a known genotoxic, alkylating agent was used as a positive control for micronuclei detection.

TK.6 cells were dosed with the example compounds or a vehicle control (0.1% v/v DMSO) and cultured with or without S9 metabolic activation for 24 hr. FIG. 3A shows representative plots of TK.6 cells treated with an example compound (VII-3), with or without S9 metabolic activation. Methyl methanesulfonate, a known genotoxic, alkylating agent was used as a positive control for micronuclei detection. By comparison of the plots, the representative compound did not exhibit genotoxic effect.

Figure 3B:
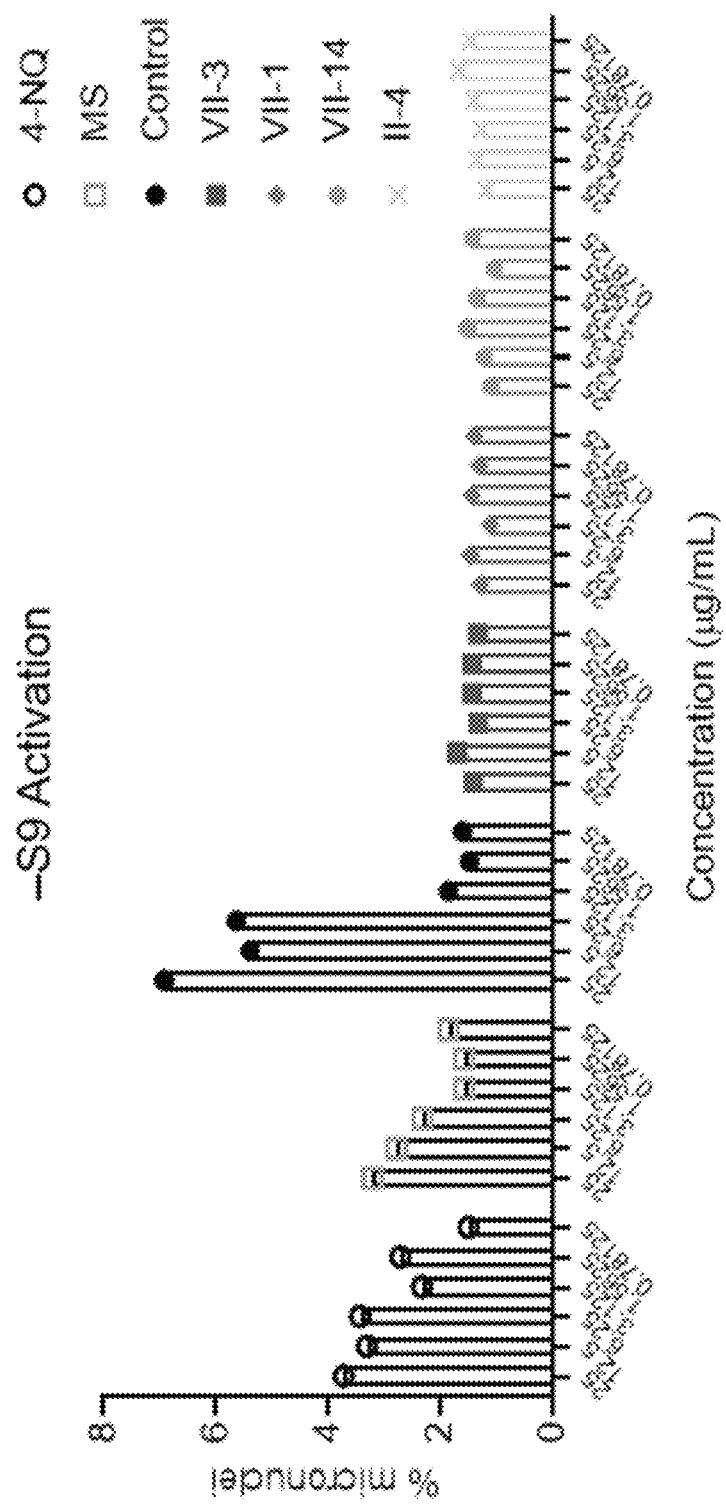
FIG. 3B and FIG. 3C show quantification of TK.6 micronuclei assay following treatment with various example compounds across a concentration range, in accordance with one or more embodiments of the present disclosure.
Figure 3C:
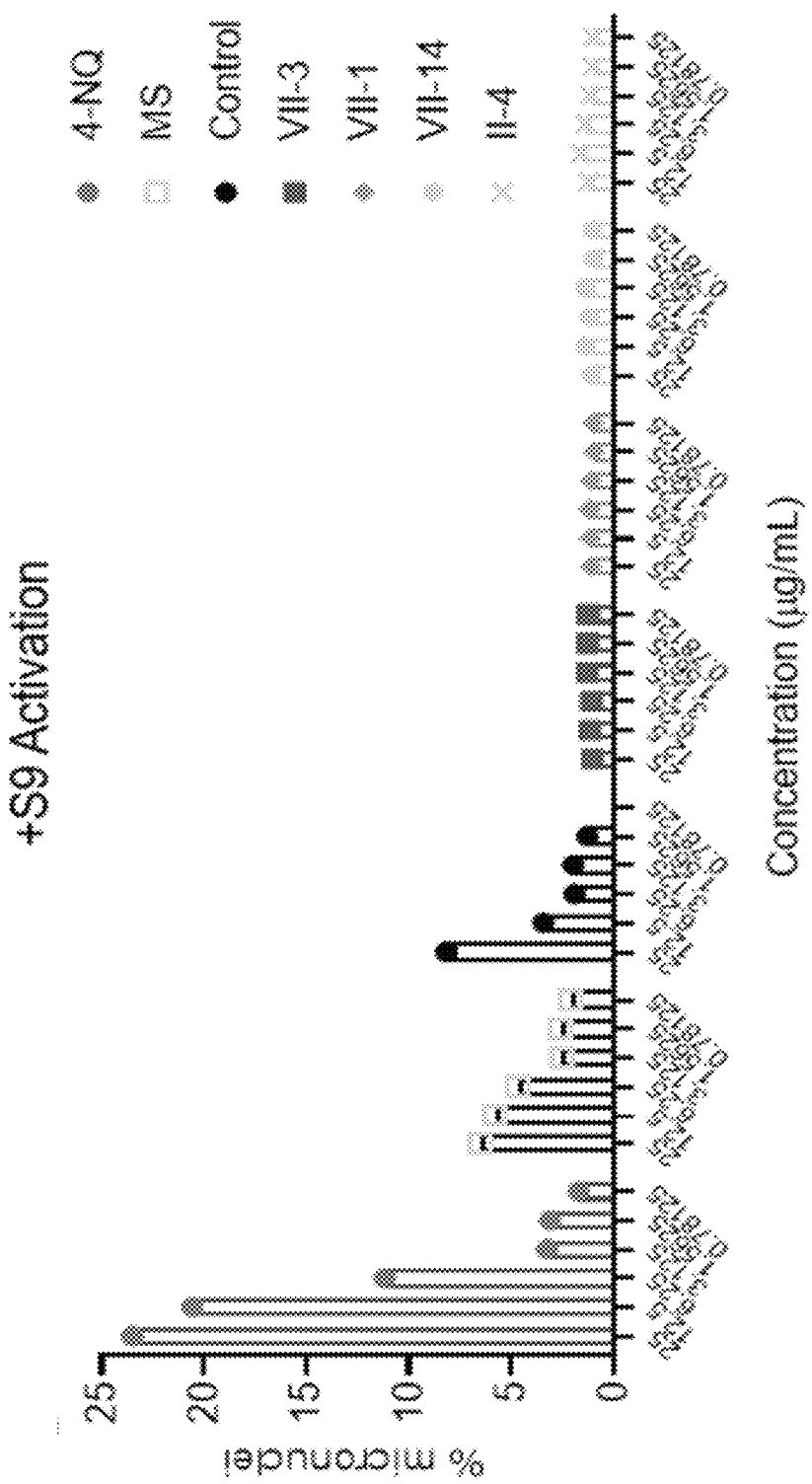

The micronucleus assay was also performed to determine if the compounds are genotoxic by evaluating the presence of micronuclei. FIG. 3B shows quantification of TK.6 micronuclei assay following treatment with various example compounds across a concentration range without S9 metabolic activation. FIG. 3C shows quantification of TK.6 micronuclei assay following treatment with various example compounds across a concentration range with S9 metabolic activation. In combination. FIGS. 3B and 3C show that the example compounds VII-3, VII-1, VII-14, and II-4 do not promote any micronuclei formation, thus demonstrating no genotoxic transformation potential, in the absence or presence of S9 metabolic activation. I-17 elicited genotoxicity at >3.125 µg/mL.

Figure 3D:
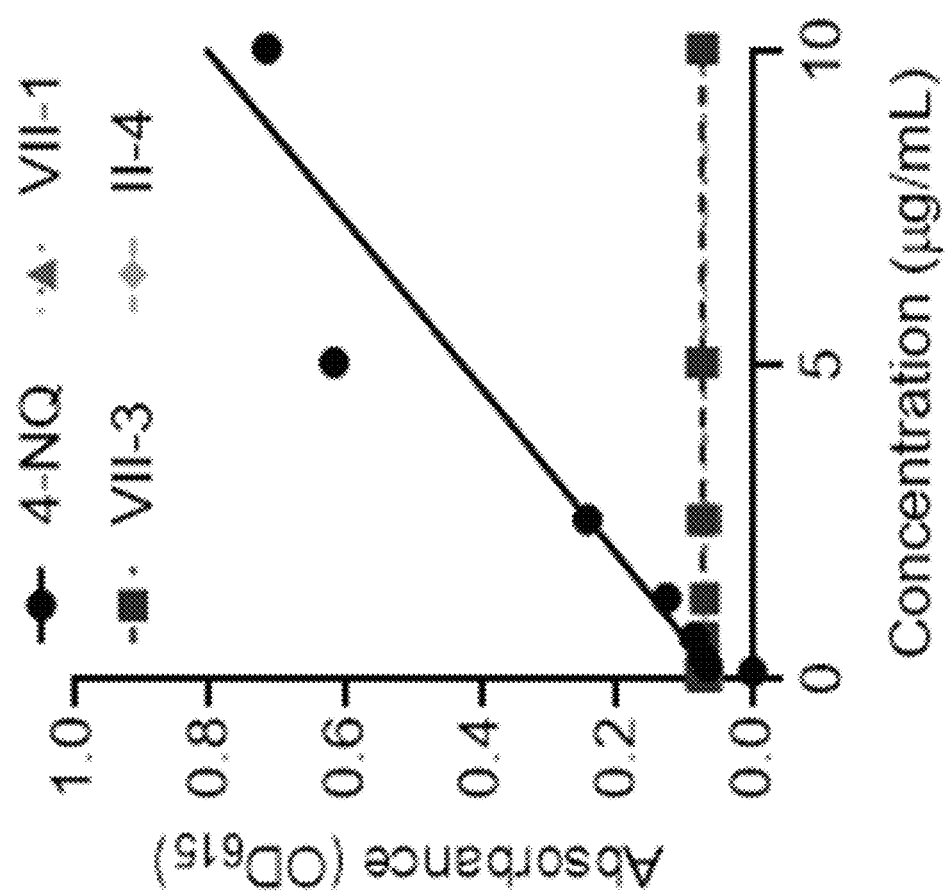
FIG. 3D shows normalized β-galactosidase activity (as quantified via absorbance) from the SOS chromotest using a known genotoxin (4-NQ; 4-nitroquinoline-1-oxide) and example compounds at varying concentrations, in accordance with one or more embodiments of the present disclosure. The SOS chromotest is a well-established bacteria-based test for genotoxicity.

FIG. 3D shows normalized β-galactosidase activity (as quantified via absorbance) from the SOS chromotest using a known genotoxin (4-NQ; 4-nitroquinoline-1-oxide) and representative compounds at varying concentrations. The SOS chromotest is a well-established bacteria-based test for genotoxicity. Similar to the results of the micronucleus assay, compounds VII-3, VII-1, and II-4 did not exhibit any genotoxic effects.

Figure 3E:
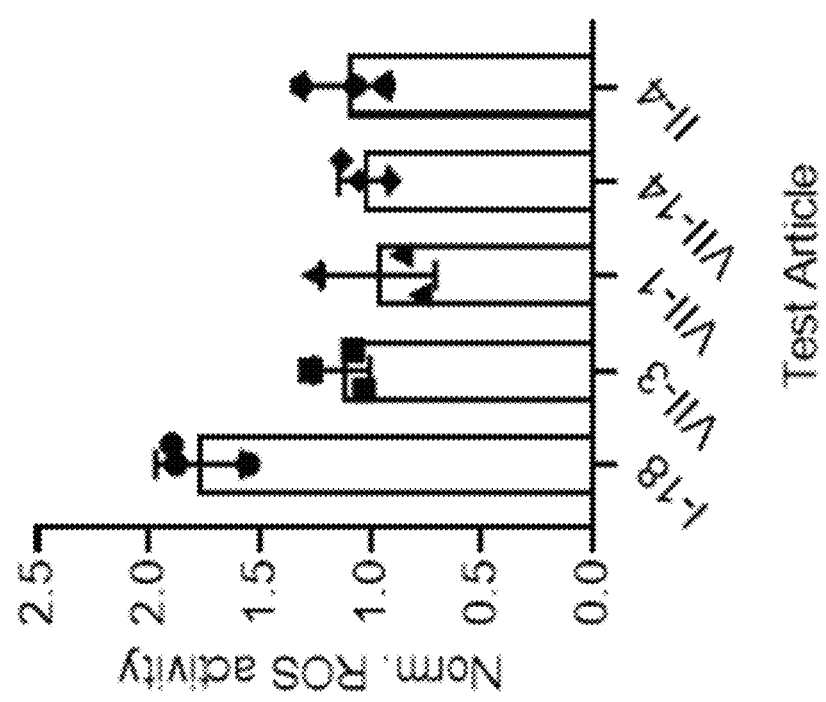
FIG. 3E shows normalized reactive oxygen species (ROS) activity in follicle dermal papilla cells treated with 5 μg/mL example compounds relative to vehicle control (0.1% v/v DMSO) after 24 hr.

Normalized reactive oxygen species (ROS) activity in follicle dermal papilla cells were analyzed after treatment with 5 µg/mL example compounds relative to vehicle control (0.1% v/v DMSO) after 24 hr. The increase in ROS levels is harmful to cell homeostasis, structures, and functions and results in oxidative stress. As shown in FIG. 3E, the ROS level of I-18 was higher than other compounds.

Figure 3F:
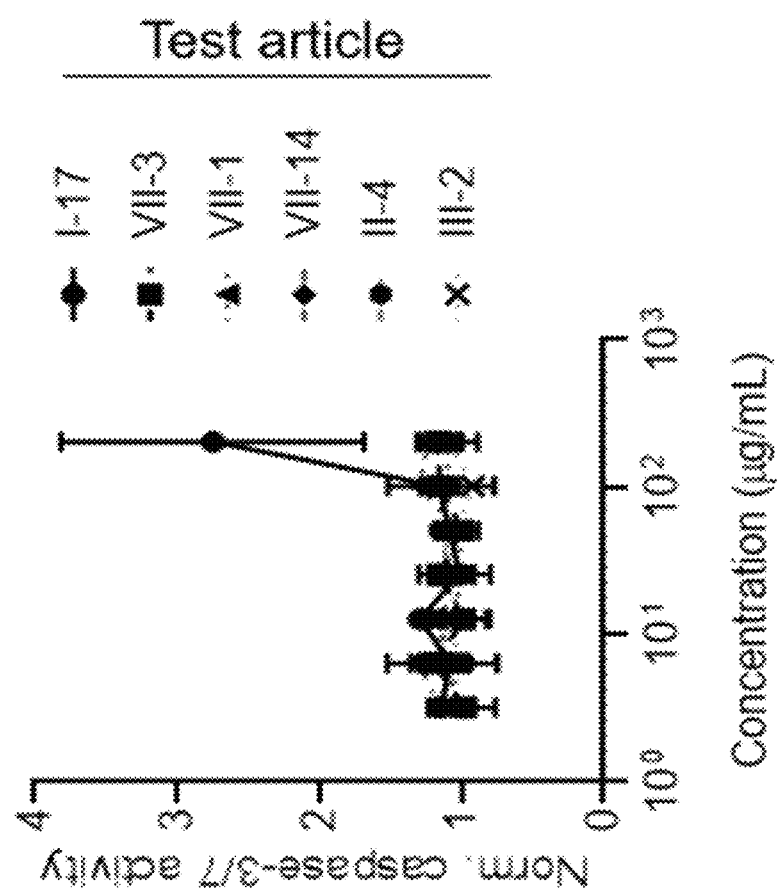
FIG. 3F shows normalized caspase 3/7 activity in HepG2 cells, an immortalized liver cell line commonly used to study apoptosis induced by small molecules. Cells were treated with either the example compounds or vehicle control containing correspondingly % v/v-matched amounts of DMSO spanning a >2-log concentration range. Data represents mean±s.d. and representative of at least 2 experimental replicates.

HepG2 cells are an immortalized liver cell line commonly used to study apoptosis induced by small molecules. Normalized caspase 3/7 activity in HepG2 was measured as shown in FIG. 3F. Cells were treated with either the example compounds or vehicle control containing correspondingly % v/v-matched amounts of DMSO spanning a >2-log concentration range. Data represents mean±s.d. and representative of at least 2 experimental replicates. Aside from compound I-17, which resulted in significant caspase-3/7 activation at the highest concentration, compounds VII-3, VII-1, VII-14, and II-4 did not exhibit any caspase activation across a 2-log concentration range.

Figure 4A:
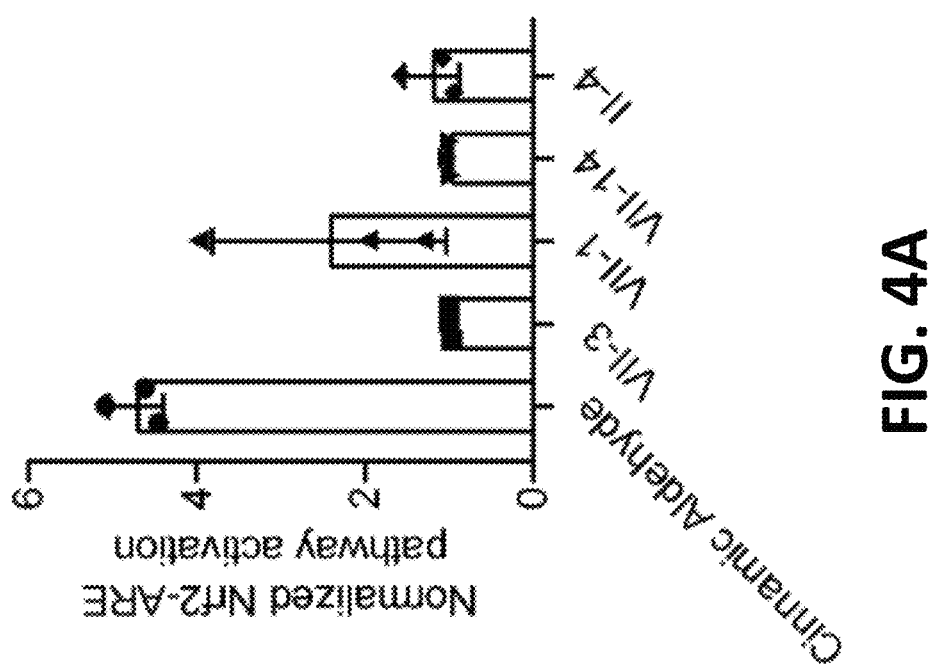
FIG. 4A shows normalized ARE-luciferase activity using a known sensitizing compound (cinnamic aldehyde) and example compounds, in accordance with one or more embodiments of the present disclosure.

Example 11: Example Compounds do not Exhibit any Skin Sensitizing Potential or Immunogenicity The Nrf2-ARE pathway is a master regulator of cytoprotective responses to oxidative stress, and is an early indicator of skin sensitization. Nrf2 (nuclear factor erythroid 2-related factor) is a transcription factor that binds to antioxidant responsive elements (ARE). By fusing ARE to the light-producing luciferase gene, a KeratinoSens Nrf2-ARE reporter assay was performed whereby luciferase signal is directly correlated to Nrf2-ARE pathway activation. Normalized ARE-luciferase activity was measured using a known sensitizing compound (cinnamic aldehyde) and example compounds. Compound VII-1 exhibited sensitizing potential (FIG. 4A).

Figure 4C:
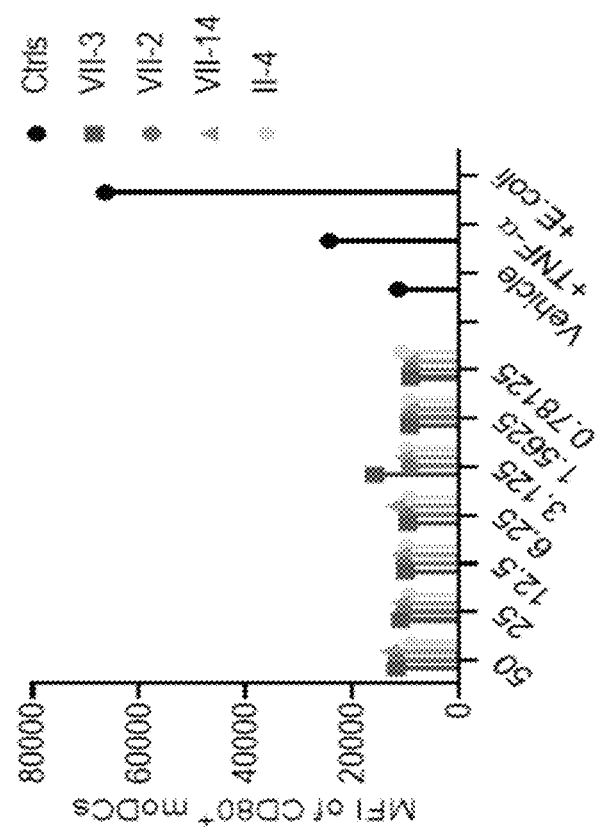
FIG. 4B-4E show in vitro dendritic cell sensitization test, in accordance with one or more embodiments of the present disclosure. Dendritic cell activation is widely-associated with downstream immunogenicity. CD14+ cells from human donor peripheral mononuclear cells were harvested and differentiated them into immature monocyte-derived DCs using granulocyte-macrophage colony-stimulating factor (GM-CSF) and interleukin-4 (IL-4), then treated with the example compounds. Killed E. Coli and TNF-α were used as positive controls.
Figure 4B:
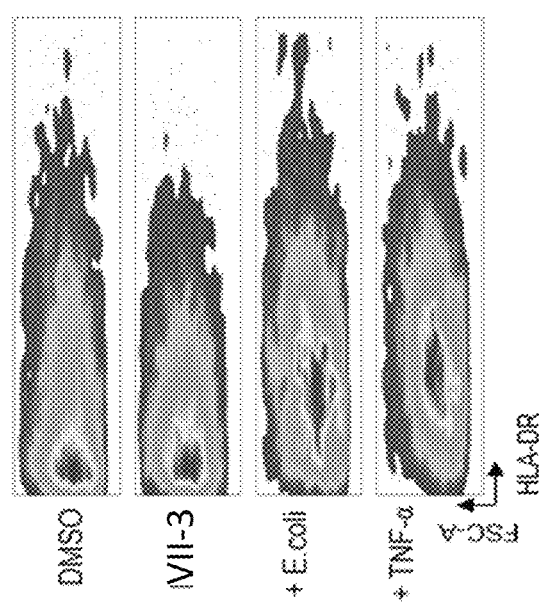
Figure 4E:
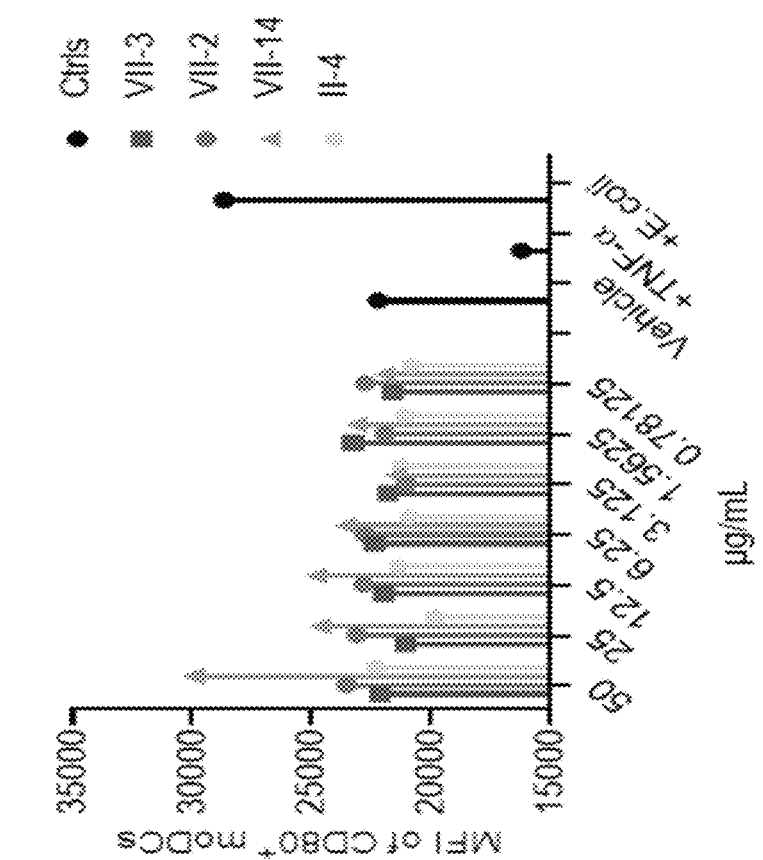
Figure 4D:
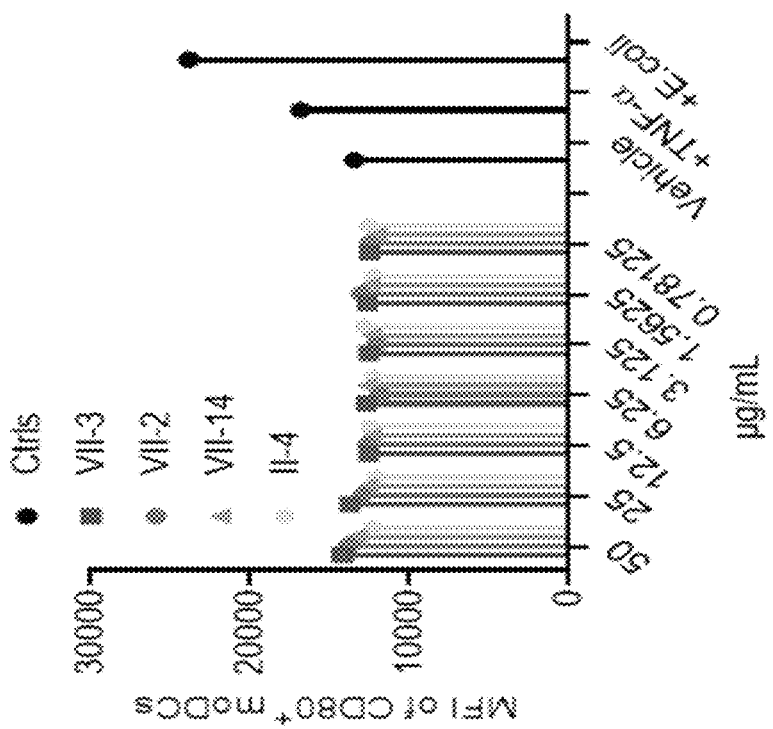

To evaluate skin sensitizing potential or immunogenicity, in vitro dendritic cell sensitization test was also performed. Dendritic cell activation is widely-associated with downstream immunogenicity. CD14+ cells from human donor peripheral mononuclear cells were harvested and differentiated them into immature monocyte-derived DCs using granulocyte-macrophage colony-stimulating factor (GM-CSF) and interleukin-4 (IL-4), then treated with the example compounds. Killed *E. Coli* and TNF-α were used as positive controls. FIG. 4B shows representative plots showing change in HLA-DR expression. FIGS. 4C, 4D, and 4E show expression of CD80, PDL-1, and CD141, respectively, as quantified via mean fluorescence intensity (MFI) following dosing with various example compounds. Data represents mean±s.d. and representative of at least 2 experimental replicates, example compounds did not exhibit any skin sensitizing potential or immunogenicity

Example 12: Example Compounds do not Elicit Caspase-3 Activation in Skin Tissues Ex Vivo Leftover hair-containing skin tissue from cosmetic surgeries was biopsy-punched and prepared as ready-to-use skin models (Genoskin). The samples were preserved and cultured for ex vivo testing with vehicle control (distilled water) or example compounds for 24 hrs, then processed for two-photon microscopy.

Figure 5A:
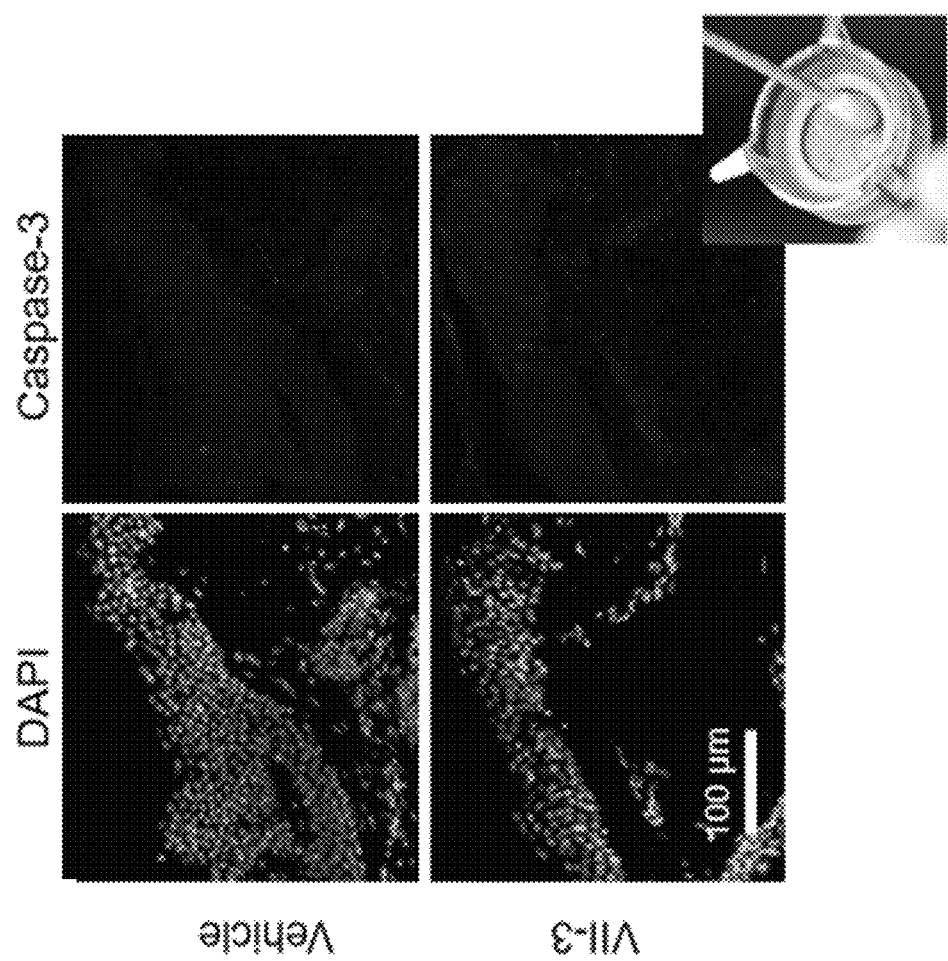
FIG. 5A shows representative images of ex vivo epithelial samples of epidermal tissue surrounding hair follicles 24 hr following treatment. Samples were stained for Caspase-3 (red) and with DAPI (cyan). Inset shows representative image of ex vivo skin model.

FIG. 5A are representative images of ex vivo epithelial samples of epidermal tissue surrounding hair follicles 24 hr following treatment. Samples were stained for Caspase-3 and with DAPI. Inset shows representative image of ex vivo skin model.

Figure 5B:
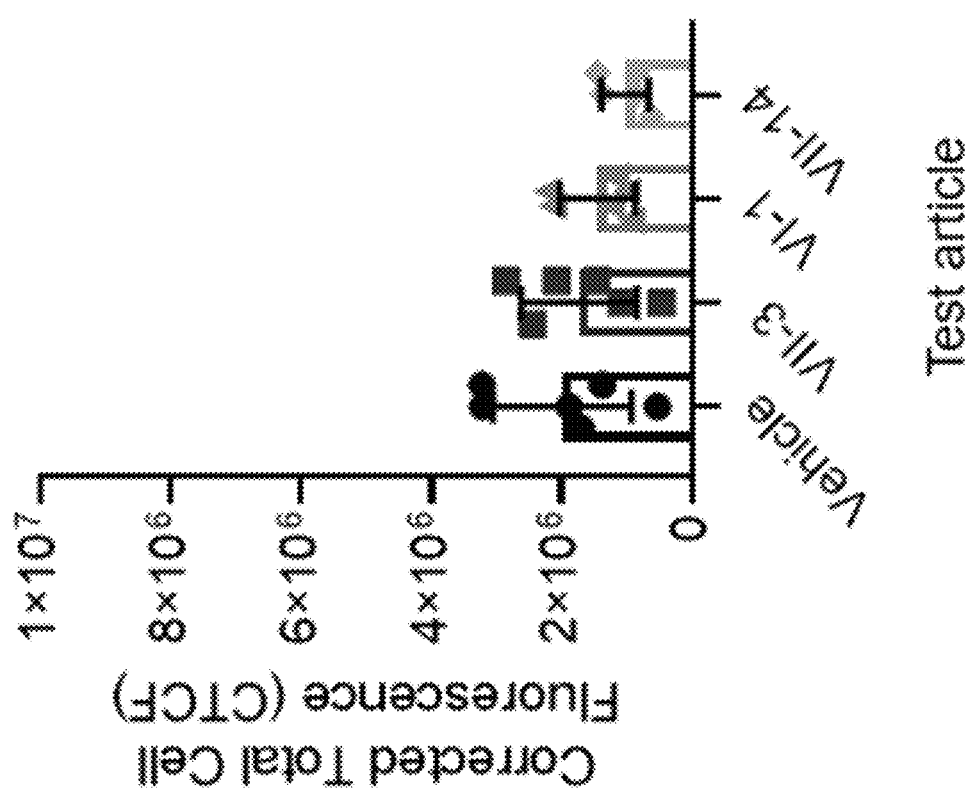
FIG. 5B shows average corrected fluorescence of cells stained for caspase-3. Images and data are representative of tissues derived from n=2 donors.

Average corrected fluorescence of cells stained for caspase-3 were measured for samples treated with various representative compounds. Images and data are representative of tissues derived from n=2 donors. As shown in FIG. 5B, example compounds did not elicit Caspase-3 activation in skin tissues ex vivo.

Example 13: Clinical Repeat Insult Patch Test

The clinical test was performed by Eurofins|CRL, Inc. The test followed established, standardized procedures for clinical testing designed to ensure the well-being of clinical study subjects and the generation of reliable study data. A total of 239 male and female subjects, ranging in age from 18 to 70 years were selected for study participation. The objective of the study was to determine the potential of the test material containing 0.02% v/v of the example compound in eliciting dermal irritation and/or induce sensitization following repeated patch applications.

TABLE 21

Clinical repeat insult patch test

| Subjects Completed | Sex | Patch type | Adverse reactions |
| --- | --- | --- | --- |
| 218/239 (20 subjects lost during follow-up, 1 subject excluded due to unrelated event) | 58 M and 160 F | Occlusive | 0/218 (0%) 1 subject exhibited erythema, papules, pustules and post-inflammatory hyperpigmentation consistent with acne due to an unrelated event and was excluded from the study |

Example 14: Clinical Consumer Perception Study

The clinical test was performed by Eurofins|CRL, Inc. The test followed established, standardized procedures for clinical testing designed to ensure the well-being of clinical study subjects and the generation of reliable study data. Subjects were female and ranged in age from 27-65 years. Subjects used a simple, water-based formula containing an example compound, VII-3 (at 0.02% v/v) every 2 days in the morning or night on dry or towel-dried hair. Approximately 2 mL was applied directly to the hairline. No randomization was required for the study and subjects were blinded to the name of the test material.

TABLE 22

Clinical consumer perception study using compound VII-3

| | | | | Questions | | |
| --- | --- | --- | --- | --- | --- | --- |
| | | Study | | Subjects who saw improvements in | Subjects with tight hairstyles | Subjects who saw increased |
| Subjects Completed | Adverse effects | Analysis | Blinding | their hair's appearance | who noticed less shedding | hair growth and thickness |
| 32/35 (3 subjects lost during follow-up) | 0/32 (0%) | 6 weeks (digital photography) | Subjects were blinded to the name of the test material | 31/32 (97%) | 28/32 (87%) | 26/32 (82%) |

Example 15: Subjects' Hair in Clinical Consumer Perception Study

Figure 6:
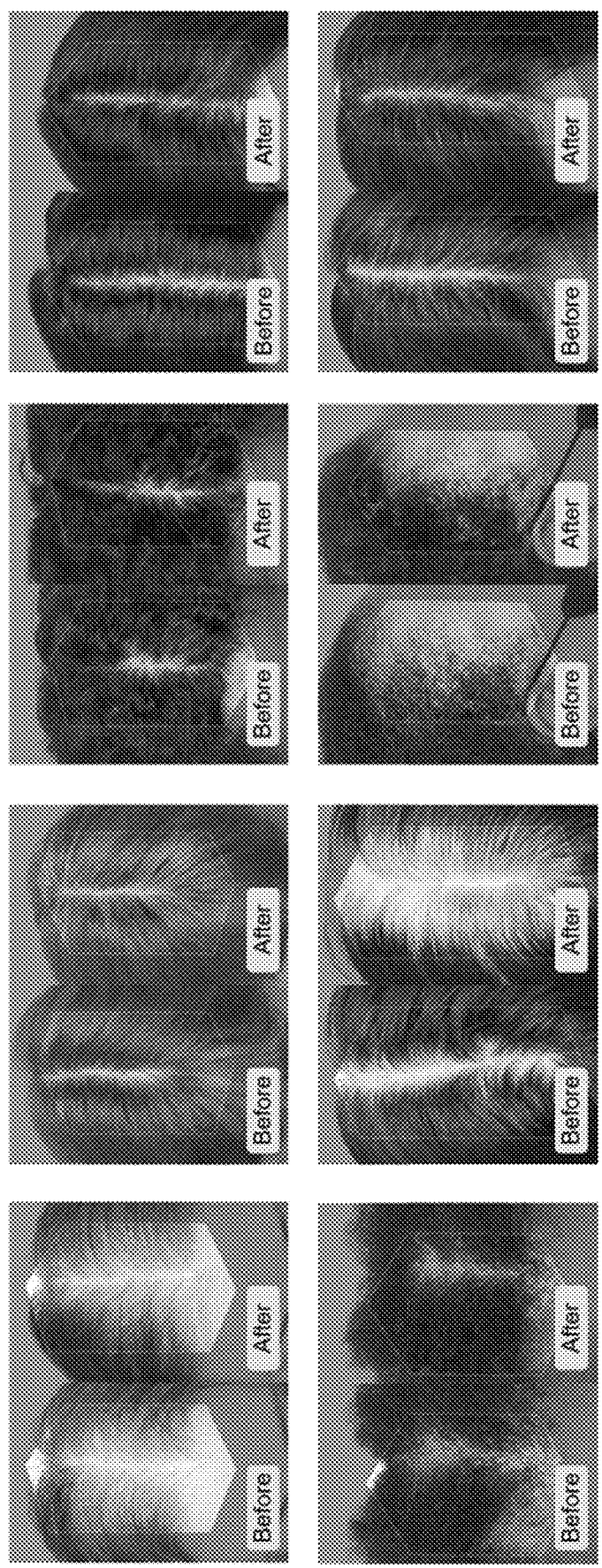
FIG. 6 shows example photographs of subjects' hair in clinical consumer perception study. Photographs were taken after 6 weeks. Subjects were female and ranged in age from 27-65 years. Subjects used a simple, water-based formula containing an example compound (at 0.02% v/v) every 2 days in the morning or night on dry or towel-dried hair. Approximately 2 mL was applied directly to the hairline. No randomization was required for the study and subjects were blinded to the name of the test material.

Photographs of subjects' hair were taken 6 weeks after the treatment with the representative compounds (FIG. 6). Subjects were female and ranged in age from 27-65 years. Subjects used a simple, water-based formula containing an example compound VII-3 (at 0.02% v/v) every 2 days in the morning or night on dry or towel-dried hair. Approximately 2 mL was applied directly to the hairline. No randomization was required for the study and subjects were blinded to the name of the test material. FIG. 6. highlights specific regions of the included participants' scalps, juxtaposing pictures taken before and after the study. Based on clinical surveys, 97% of women reported an improvement in their hair's appearance while 82% reported increased hair growth and thickness.

TABLE 23

Subject demographics of clinical consumer perception study using compound VII-3

| Subject Number | Age | Gender |
| --- | --- | --- |
| 1 | 51 | Female |
| 2 | 46 | Female |
| 3 | 56 | Female |
| 4 | 58 | Female |
| 5 | 48 | Female |
| 6 | 55 | Female |
| 7 | 51 | Female |
| 8 | 54 | Female |
| 9 | 57 | Female |
| 10 | 52 | Female |
| 11 | 37 | Female |
| 12 | 35 | Female |
| 13 | 65 | Female |
| 14 | 59 | Female |
| 15 | 31 | Female |
| 16 | 54 | Female |
| 17 | 27 | Female |
| 18 | 63 | Female |
| 19 | 61 | Female |
| 20 | 64 | Female |
| 21 | 56 | Female |
| 22 | 64 | Female |
| 23 | 35 | Female |
| 24 | 61 | Female |
| 25 | 27 | Female |
| 26 | 56 | Female |
| 27 | 64 | Female |
| 28 | 56 | Female |

TABLE 23-continued

Subject demographics of clinical consumer perception study using compound VII-3

| Subject Number | Age | Gender |
|---|---|---|
| 29 | 55 | Female |
| 30 | 59 | Female |
| 31 | 35 | Female |
| 32 | 61 | Female |
| 33 | 59 | Female |
| 34 | 45 | Female |
| 35 | 47 | Female |

After the conclusion of the study, subjects completed a Consumer perception questionnaire. Table 24 includes percentages of each response for the corresponding prompt in the questionnaire. The specific response choice is specified within the parentheses below the percentage.

TABLE 24

Subject responses of clinical consumer perception study using compound VII-3

| Prompt | Responses | | | | |
|---|---|---|---|---|---|
| Because of the treatment I have received since the start of the study, the appearance of my hair is: | 18.8% (Thicker) | 21.9% (Stronger) | 56.3% (Fuller) | 3.1% (Thinner) | 0% (Weaker) |
| Since the beginning of the study, I have noticed a decrease of the number of hairs lost in the shower. | 18.8% (Strongly Agree) | 53.1% (Agree) | 6.3% (Disagree) | 0% (Strongly Disagree) | 21.9% (I haven't noticed a change) |
| Since the start of the study, I can see more hair in the areas where the serum was applied. | 12.5% (Strongly Agree) | 53.1% (Agree) | 3.1% (Disagree) | 0% (Strongly Disagree) | 31.3% (I haven't noticed a change) |
| Since the start of the study, how effective do you think the treatment has been in increasing your hair growth/thickness? | 9.4% (Very effective) | 71.9% (Somewhat effective) | 18.8% (Not very effective) | 0% (Not effective at all) | |
| Since the start of the study, how effective do you think the treatment has been in slowing down your hair loss? | 28.1% (Very effective) | 53.1% (Somewhat effective) | 15.6% (Not very effective) | 3.1% (Not effective at all) | |

Figures 7A, 7B:
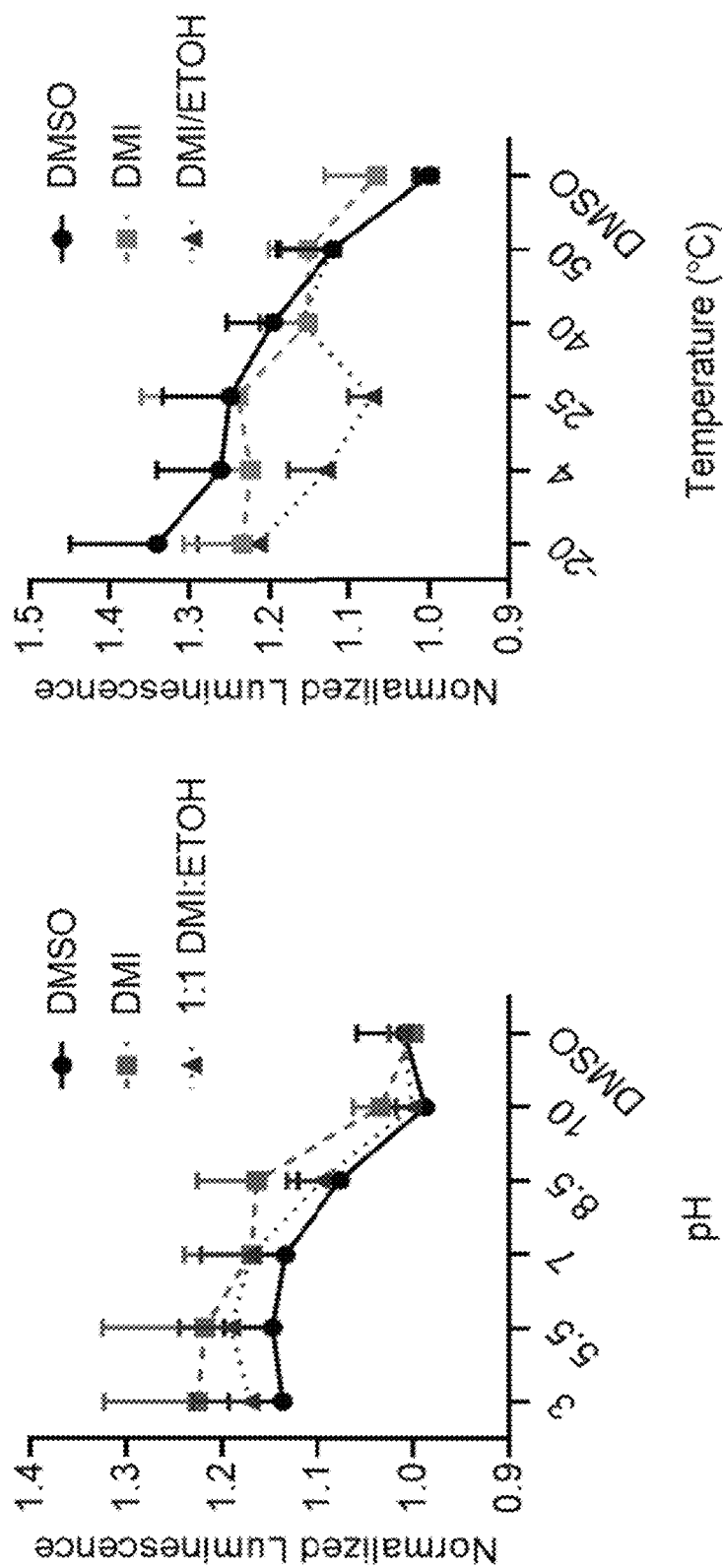
FIGS. 7A and 7B show normalized proliferation follicle papilla cell proliferation after 48 hr following treatment with the example compound (VII-3) pre-treated across a range of pH conditions (FIG. 7A) and temperature conditions (FIG. 7B). Data represents mean±s.d. and representative of n=2 donors.

Example 16: A Compound Disclosed Herein is Functionally Stable Across Physiologically-Relevant PH and Temperature Ranges Compound VII-3 was prepared in various solvents (DMSO; dimethyl sulfoxide, DMI; dimethyl isosorbide, or a 1:1 mixture of dimethyl isosorbide and ethanol), the diluted in pH-adjusted water and left at varying temperatures for 7 days. Human follicle papilla cells were dosed at 5 µg/mL with the example compound and further supplemented with 6-bromoindirubin-39-Oxime (BIO), recombinant bone morphogenetic protein-2 (BMP-2), and basic fibroblast growth factor (FGFβ), whose combination was previously found to preserve in vivo dermal papilla gene signatures. Normalized proliferation follicle papilla cell proliferation was analyzed after 48 hr following the treatment with the example compound pre-treated across a range of pH conditions (FIG. 7A) and temperature conditions (FIG. 7B). Data represents mean±s.d. and representative of n=2 donors. The resulting data showed that the example compound is functionally stable across physiologically-relevant pH and temperature ranges.

Example 17: Synthesis Method of Compound VII-3

Synthesis of compound, VII-3 was carried out following Scheme 1 given below:

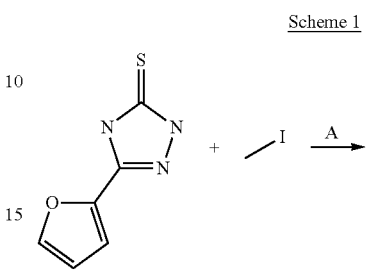

Scheme 1

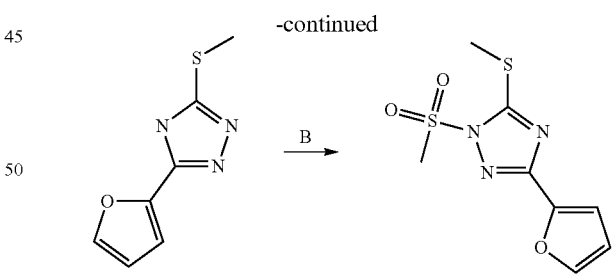

-continued

The synthesis could be performed in two different ways. As the first method, to a water solution of EtOH (100 ml of water and 100 ml of EtOH), NaOH was added during 20 min at room temperature. 3-(furan-2-yl)-1H-1,2,4-triazole-5 (4H)-thione (20 g, 0.1 mol) was added by portions at room temperature with stirring. The mixture was stirred at room temperature for 1 h. MeI was added by drop at room temperature for 25 min and stirred the mixture for 12 h. The solution was evaporated to half the volume under reduced pressure (50° C., 20 mm), precipitate was filtered off, washed with water (3×100 ml) and dried. Final yield of the target compound was 68%.

The compound was also synthesized by the second method as follows. 3-(furan-2-yl)-5-(methylthio)-4H-1,2,4-triazole (18 g) was mixed with dry THF (125 ml) and NEt3 was added by drop at 5° C. To a water solution of EtOH (100 ml of water and 100 ml of EtOH) NaOH was added during 20 min at room temperature. The mixture was cooled to 5° C. and MeSO$_2$Cl was added by drop, stirred for 1 h at 10° C. and 12 h at room temperature. 500 ml of water was added and stirred for 1 h. The precipitate was filtered, washed with water (3×80 ml), and dried. The product was purified by column chromatography (eluent MTBE/CH$_2$Cl$_2$ 50/50). Solvent was evaporated. Final yield of the target compound was 72%.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition for treating hair loss or hair thinning comprising (i) a compound having a structure of Formula (VII$_B$-A):

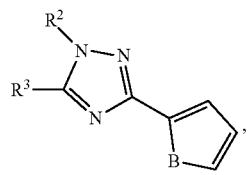

Formula (VII$_B$-A)

or a pharmaceutically or cosmetically acceptable salt thereof, wherein;
B is selected from oxygen and sulfur;
R$^2$ is -S(O)$_2$(R$^{11}$); and
R$^3$ is -SR$^{11}$;
wherein each R$^{11}$ is selected from C$_{1-6}$ alkyl, and
(ii) dimethyl isosorbide;
wherein a weight % of the compound in the composition is at least about 0.0001% to at most about 10% by weight relative to a total weight of the composition.

2. The composition of claim 1, wherein B is oxygen.

3. The composition of claim 1, wherein the weight % of the compound in the composition ranges from about 0.001% to about 2.0%.

4. The composition of claim 1, wherein the composition is a pharmaceutical composition or a cosmetic composition.

5. The composition of claim 1, wherein the hair loss is selected from androgenic alopecia, alopecia areata, androgenetic alopecia, gynecologic alopecia, postpartum alopecia, seborrheic alopecia, non-rigid alopecia, senile alopecia, chemotherapy-induced alopecia, radiation-induced alopecia, male-pattern baldness, female-pattern baldness, cicatricial alopecia, alopecia areata telogen effluvium, traction alopecia, anagen effluvium, and combinations thereof.

6. The composition of claim 1, wherein the hair comprises scalp hair, eyelash hair, eyebrow hair, facial hair, or combinations thereof.

7. The composition of claim 1, wherein the composition further comprises at least one additive selected from the group consisting of a pharmaceutically or cosmetically acceptable carrier, excipient, adjuvant, and diluent.

8. The composition of claim 1, wherein the composition is formulated as a toner, emulsion, cream, gel, shampoo, soap, serum, spray, or oil.

9. The composition of claim 1, further comprising one or more ingredients selected from the group consisting of: Biotin, Caffeine, Camellia Sinensis Leaf Extract, Citrus Paradisi Peel Extract, Dipotassium Glycyrrhizate, Ganoderma Lucidum Extract, Inositol, Panax Ginseng Root Extract, Pinus Pinaster Bark Extract, Piper Nigrum Fruit Extract, Pyrus Malus Fruit Extract, Resveratrol, Serenoa Serrulata Fruit Extract, Trifolium Pratense Flower Extract, Aqua/Eau/Water, Ethanol, polyethylene glycol (PEG)-40 Castor Oil, Butylene Glycol, Glycerin, Niacin, Ethoxydiglycol, and PEG-40 Hydrogenated Castor Oil.

10. The composition of claim 1, wherein the weight % of the compound in the composition is 0.005% to 0.2%.

11. The composition of claim 1, wherein the compound of Formula (VII$_B$-A) comprises

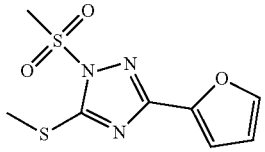 [SMILES: CSc1nc(-c2ccco2)nn1S(C)(=O)=O]

or a pharmaceutically or cosmetically acceptable salt thereof.

12. A method for treating hair loss or hair thinning, the method comprising administering to a subject in need thereof the composition of claim 1.

* * * * *

UNITED STATES PATENT AND TRADEMARK OFFICE
CERTIFICATE OF CORRECTION

| | |
|---|---|
| PATENT NO. | : 12,251,459 B2 |
| APPLICATION NO. | : 18/092517 |
| DATED | : March 18, 2025 |
| INVENTOR(S) | : Avinash Boppana et al. |

It is certified that error appears in the above-identified patent and that said Letters Patent is hereby corrected as shown below:

On the Title Page

Item (73): Remove the name "Seung Hyeon Ko" from Assignees.

Signed and Sealed this
Twentieth Day of May, 2025

Coke Morgan Stewart
*Acting Director of the United States Patent and Trademark Office*